US012780873B2

(12) United States Patent
Del Valle et al.

(10) Patent No.: US 12,780,873 B2

(45) **Date of Patent: *Nov. 3, 2026**

(54) MODIFIED PEPTIDES FOR THE INHIBITION OF ABNORMAL TAU ACCUMULATION

(71) Applicant: University of Notre Dame du Lac, South Bend, IN (US)

(72) Inventors: Juan Del Valle, South Bend, IN (US); Kamlesh Makwana, South Bend, IN (US); Matthew Sarnowski, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 578 days.

This patent is subject to a terminal disclaimer.

(21) Appl. No.: 18/263,190

(22) PCT Filed: Apr. 25, 2022

(86) PCT No.: PCT/US2022/026110

§ 371 (c)(1),
(2) Date: Jul. 27, 2023

(87) PCT Pub. No.: WO2022/232007

PCT Pub. Date: Nov. 3, 2022

(65) Prior Publication Data

US 2024/0116984 A1 Apr. 11, 2024

Related U.S. Application Data

(60) Provisional application No. 63/179,350, filed on Apr. 25, 2021.

(51) Int. Cl.

*C07K 7/00* (2006.01)
*C07K 7/06* (2006.01)
*A61K 38/00* (2006.01)

(52) U.S. Cl.

CPC ................ *C07K 7/06* (2013.01); *A61K 38/00* (2013.01)

(58) Field of Classification Search

CPC ....... C07K 7/06; C07K 14/4711; A61K 38/00
See application file for complete search history.

(56) References Cited

U.S. PATENT DOCUMENTS

| | | | |
|---|---|---|---|
| 5,861,257 | A | 1/1999 | Vandermeeren et al. |
| 6,200,768 | B1 | 3/2001 | Mandelkow et al. |
| 6,376,205 | B1 | 4/2002 | Wischik et al. |
| 6,417,185 | B1 | 7/2002 | Goff et al. |
| 6,579,691 | B1 | 6/2003 | Mandelkow et al. |
| 6,743,771 | B2 | 6/2004 | Douglas et al. |
| 6,812,339 | B1 | 11/2004 | Venter et al. |
| 7,135,610 | B2 | 11/2006 | Takashima |
| 7,446,180 | B2 | 11/2008 | Novak |
| 7,449,190 | B2 | 11/2008 | Nabel et al. |
| 7,608,682 | B2 | 10/2009 | Davydov et al. |
| 7,834,237 | B2 | 11/2010 | Wischik et al. |
| 7,842,467 | B1 | 11/2010 | Heidbrink et al. |
| 7,964,556 | B1 | 6/2011 | Kobayashi et al. |
| 8,017,746 | B2 | 9/2011 | Miyawaki et al. |
| 8,506,933 | B2 | 8/2013 | Nayak |
| 8,586,006 | B2 | 11/2013 | Hood et al. |
| 8,697,076 | B2 | 4/2014 | Binder et al. |
| 8,729,225 | B2 | 5/2014 | Reed et al. |
| 8,835,137 | B2 | 9/2014 | Roberts et al. |
| 8,926,974 | B2 | 1/2015 | Griswold-prenner et al. |
| 8,940,945 | B2 | 1/2015 | Dickey et al. |
| 8,993,263 | B2 | 3/2015 | Reed |
| 9,040,521 | B2 | 5/2015 | Gan |
| 9,073,990 | B2 | 7/2015 | Paas et al. |
| 9,180,203 | B2 | 11/2015 | Cui et al. |
| 9,200,068 | B2 | 12/2015 | Ashe et al. |
| 9,254,311 | B2 | 2/2016 | Bancel et al. |
| 9,464,122 | B2 | 10/2016 | Moe et al. |
| 9,485,972 | B2 | 11/2016 | Kontsekovà |
| 9,506,051 | B2 | 11/2016 | Moe et al. |
| 9,527,894 | B2 | 12/2016 | Robitzki et al. |
| 9,562,091 | B2 | 2/2017 | Grueninger et al. |
| 9,738,709 | B2 | 8/2017 | Kuret et al. |
| 9,828,421 | B2 | 11/2017 | Novák et al. |
| 9,834,596 | B2 | 12/2017 | Holtzman et al. |
| 9,878,004 | B2 | 1/2018 | Williams et al. |
| 10,112,990 | B2 | 10/2018 | Adolfsson et al. |
| 10,167,482 | B2 | 1/2019 | Coffin |

(Continued)

FOREIGN PATENT DOCUMENTS

WO 2019233883 A1 12/2019

OTHER PUBLICATIONS

Tillett et al. "N-Amino peptide scanning reveals inhibitors of Aß42 aggregation," RSC Adv., A Apr. 8, 2020 (Apr. 8, 2020), vol. 10 , Iss. 24, pp. 14331-14336.*

Arakhamia, T., et al. Posttranslational Modifications Mediate the Structural Diversity of Tauopathy Strains. Cell (2020), 180, 633-644.e12.

Berriman, J., et al. Tau filaments from human brain and from in vitro assembly of recombinant protein show cross-beta structure. Proc. Natl. Acad. Sci. U S A (2003), 100, 9034-9038.

Braak, H., et al. Staging of Alzheimer disease-associated neurofibrillary pathology using paraffin sections and immunocytochemistry. Acta Neuropathol. (2006), 112, 389-404.

Brunden, K. R., et al. Advances in tau-focused drug discovery for Alzheimer's disease and related tauopathies. Nat. Rev. Drug Discov. (2009), 8, 783-793.

(Continued)

*Primary Examiner* — Jeanette M Lieb

(74) *Attorney, Agent, or Firm* — Michael Best & Friedrich LLP

(57) ABSTRACT

Described herein are N-amino peptides (NAPs) that inhibit disease-associated tau aggregation and prevent fibril formation. The NAPs are derived from the R2 and R3 domains of tau (VQIINK and VQIVYK, respectively) wherein the amide moiety is N-aminated. N-amination of the R2 and R3 domains of tau results in formation of soluble mimics of ordered β-strands that are aggregation resistant and can assemble into layered parallel β-sheets.

28 Claims, 16 Drawing Sheets

Specification includes a Sequence Listing.

(56) References Cited

U.S. PATENT DOCUMENTS

| | | | | |
|---|---|---|---|---|
| 10,287,343 | B2 | 5/2019 | Knight et al. | |
| 10,301,379 | B2 | 5/2019 | Wadia et al. | |
| 10,358,485 | B2 | 7/2019 | Roberts et al. | |
| 10,507,226 | B1 | 12/2019 | Del Valle | |
| 10,556,950 | B2 | 2/2020 | Eguchi et al. | |
| 10,570,408 | B2 | 2/2020 | Deng et al. | |
| 10,590,191 | B2 | 3/2020 | Fagret et al. | |
| 10,668,147 | B2 | 6/2020 | Stein et al. | |
| 10,766,953 | B2 | 9/2020 | Mercken et al. | |
| 10,830,775 | B2 | 11/2020 | Bateman et al. | |
| 2011/0144029 | A1 * | 6/2011 | D'Mello | A61P 25/28 514/17.7 |

OTHER PUBLICATIONS

Brunello, C. A., et al. Mechanisms of secretion and spreading of pathological tau protein. Cell Mol. Life Sci. (2020), 77, 1721-1744.

Chemerovski-Glikman et al., "Inhibition of the aggregation and toxicity of the minimal amyloidogenic fragment of Tau by its pro-substituted analogues," Chemistry Jul. 18, 2017; 23(40): 9618-9624.

Chiti, F., et al. Rationalization of the effects of mutations on peptide andprotein aggregation rates. Nature (2003), 424, 805-808.

Congdon, E. E., et al. Nucleation-dependent tau filament formation: the importance of dimerization and an estimation of elementary rate constants. J. Biol. Chem. (2008), 283, 13806-13816.

Congdon, E. E., et al. Tau-targeting therapies for Alzheimer disease. Nat. Rev. Neurol. (2018), 14, 399-415.

Crowther, R. A., et al. The microtubule binding repeats of tau protein assemble into filaments like those found in Alzheimer's disease. FEBS Lett. (1992), 309, 199-202.

Dammers, C., et al. Selection and Characterization of Tau Binding D-Enantiomeric Peptides with Potential for Therapy of Alzheimer Disease. PLoS One (2016), 11, e0167432.

Devos, A., et al. Synthesis of acyl halides under very mild conditions. J. Chem. Soc. Chem. Comm. (1979), 1180-1181.

Drubin, D. G., et al. Nerve growth factor-induced neurite outgrowth in PC12 cells involves the coordinate induction of microtubule assembly and assembly-promoting factors. J. Cell Biol. (1985), 101, 1799-1807.

Evans, L. D., et al. Extracellular Monomeric and Aggregated Tau Efficiently Enter Human Neurons through Overlapping but Distinct Pathways. Cell Rep. (2018), 22, 3612-3624.

Fitzpatrick, A. W. P., et al. Cryo-EM structures of tau filaments from Alzheimer's disease. Nature (2017), 547, 185-190.

Frenkel-Pinter et al., "Selective inhibition of aggregation and toxicity of a tau-derived peptide using its glycosylated analogues," Chemistry Apr. 18, 2016; 22(17): 5945-52.

Frolov, A. I., et al. Prediction of Cosolvent Effect on Solvation Free Energies and Solubilities of Organic Compounds in Supercritical Carbon Dioxide Based on Fully Atomistic Molecular Simulations. J. Phys. Chem. B (2014), 118, 11769-11780.

Frost, B., et al. Propagation of tau misfolding from the outside to the inside of a cell. J. Biol. Chem. (2009), 284, 12845-12852.

Gallardo, R., et al. Amyloid structures: much more than just a cross-β fold. Curr. Opin. Struct. Biol. (2020), 60, 7-16.

Gibbons, G. S., et al. Mechanisms of Cell-to-Cell Transmission of Pathological Tau A Review. JAMA Neurol. (2019), 76, 101-108.

Goate, A., et al. Segregation of a missense mutation in the amyloid precursor protein gene with familial Alzheimer's disease. Nature (1991), 349, 704-706.

Goedert, M., et al. Multiple isoforms of human microtubule-associated protein tau: sequences and localization in neurofibrillary tangles of Alzheimer's disease. Neuron (1989), 3, 519-526.

Goedert, M., et al. Propagation of Tau Aggregates and Neurodegeneration. Annu. Rev. Neurosci. (2017), 40, 189-210.

Goedert, M., et al. Tau proteins of Alzheimer paired helical filaments: abnormal phosphorylation of all six brain isoforms. Neuron (1992), 8, 159-168.

Gordon, D. J., et al. Inhibition of beta-amyloid(40) fibrillogenesis and disassembly of beta-amyloid(40) fibrils by short beta-amyloid congeners containing N-methyl amino acids at alternate residues. Biochemistry (2001), 40, 8237-8245.

Goyal, D., et al. Rationally Designed Peptides and Peptidomimetics as Inhibitors of Amyloid-β (Aβ) Aggregation: Potential Therapeutics of Alzheimer's Disease. ACS Comb. Sci. (2017), 19, 55-80.

Grundke-Iqbal, I., et al. Abnormal phosphorylation of the microtubule-associated protein tau (tau) in Alzheimer cytoskeletal pathology. Proc. Natl. Acad. Sci. U S A (1986), 83, 4913-4917.

Hess, B., et al. GROMACS 4: Algorithms for Highly Efficient, Load-Balanced, and Scalable Molecular Simulation. J. Chem. Theory Comput. (2008), 4, 435-447.

Holmes, B. B., et al. Proteopathic tau seeding predicts tauopathy in vivo. Proc. Natl. Acad. Sci. U S A (2014), 111, E4376.

Hughes, E., et al. Inhibition of toxicity in the beta-amyloid peptide fragment beta -(25-35) using N-methylated derivatives: a general strategy to prevent amyloid formation. J. Biol. Chem. (2000), 275, 25109-25115.

Hutton, M., et al. Association of missense and 5'-splice-site mutations in tau with the inherited dementia FTDP-17. Nature (1998), 393, 702-705.

Iadanza, M. G., et al. A new era for understanding amyloid structures and disease. Nat. Rev. Mol. Cell Biol. (2018), 19, 755-773.

International Preliminary Report on Patentability for Application No. PCT/US2022/026110 dated Oct. 24, 2023 (6 pages).

International Search Report and Written Opinion for Application No. PCT/US2022/026110 dated Sep. 14, 2022 (14 pages).

Jorgensen, W. L., et al. Comparison of simple potential functions for simulating liquid water. J. Chem. Phys. (1983), 79, 926-935.

Kaminski, G. A., et al. Evaluation and Reparametrization of the OPLS-AA Force Field for Proteins via Comparison with Accurate Quantum Chemical Calculations on Peptides. J. Phys. Chem. B (2001), 105, 6474-6487.

Kang, C. W., et al. Solid-phase synthesis of tetrahydropyridazinedione-constrained peptides. Org. Lett. (2014), 16, 5434-5437.

Kang, C. W., et al. β-Strand mimics based on tetrahydropyridazinedione (tpd) peptide stitching. Chem. Commun. (2015), 51, 16259-16262.

Kfoury, N., et al. Trans-cellular propagation of Tau aggregation by fibrillar species. J. Biol. Chem. (2012), 287, 19440-19451.

Knowles, T. P. J., et al. The amyloid state and its association with protein misfolding diseases. Nat. Rev. Mol. Cell Biol. (2014), 15, 384-396.

Laxio Arenas, J., et al. Peptides and peptidomimetics as inhibitors of protein-protein interactions involving β-sheet secondary structures. Curr. Opin. Chem. Biol. (2019), 52, 157-167.

Lee, G., et al. The microtubule binding domain of tau protein. Neuron (1989), 2, 1615-1624.

Lee, VMY, et al. "Neurodegenerative tauopathies." Annual review of neuroscience 24.1 (2001): 1121-1159.

Lengyel, G. A., et al. Comparison of backbone modification in protein β-sheets by α→γ residue replacement and β-residue methylation. Org. Biomol. Chem. (2014), 12, 5375-5381.

Li, D., et al. Hierarchical chemical determination of amyloid polymorphs in neurodegenerative disease. Nat. Chem. Biol. (2021), 17, 237-245.

Li, W., et al. "Inhibition of tau fibrillization by oleocanthal via reaction with the amino groups of tau." Journal of neurochemistry 110.4 (2009): 1339-1351.

Loughlin, W. A., et al. Update 1 of: Beta-Strand Mimetics. Chem. Rev. (2010), 110, PR32-PR69.

Maeda, S., et al. Increased levels of granular tau oligomers: an early sign of brain aging and Alzheimer's disease. Neurosci. Res. (2006), 54, 197-201.

Makwana, K. M., et al. "N-amination converts amyloidogenic tau peptides into soluble antagonists of cellular seeding." ACS chemical neuroscience 12.20 (Oct. 20, 2021): 3928-3938.

Mchugh, S. M., et al. Mapping the sequence-structure relationships of simple cyclic hexapeptides. Phys. Chem. Chem. Phys. (2017), 19, 3315-3324.

European Patent Office. Extended European Search Report for Application No. 22796472.3, dated Feb. 17, 2025 (9 pages).

(56) References Cited

OTHER PUBLICATIONS

Makwana, K. M., et al. "From Aggregation to Inhibition: N-Amination Converts Amyloidogenic Tau Peptides into Soluble Antagonists of Cellular Seeding." (2021), URL:https://chemrxiv.org/engage/api-gateway/chemrxiv/assets/orp/resource/item/60c757e0567dfe66bfec6753/original/from-aggregation-to-inhibition-n-amination-converts-amyloidogenic-tau-peptides-into-soluble-antagonists-of-cellular-seeding.pdf (9 pages).
Mirbaha, H., et al. Inert and seed-competent tau monomers suggest structural origins of aggregation. eLife (2018), 7, e36584.
Morris, M., et al. Tau post-translational modifications in wild-type and human amyloid precursor protein transgenic mice. Nat. Neurosci. (2015), 18, 1183-1189.
Neve, R. L., et al. Identification of cDNA clones for the human microtubule-associated protein tau and chromosomal localization of the genes for tau and microtubule-associated protein 2. Brain Res. (1986), 387, 271-280.
Rathman, B. M., et al. Synthesis and biological evaluation of backbone-aminated analogues of gramicidin S. Bioorg. Med. Chem. Lett. (2020), 30, 127283.
Rathman, B. M., et al. Synthesis and conformation of backbone N-aminated peptides, in Methods Enzymol., vol. 656 (Ed.: E. J. Petersson), Academic Press, (2021), pp. 271-294.
Rodriguez, A., et al. Clustering by fast search and find of density peaks. Science (2014), 344, 1492-1496.
Sanders, D. W., et al. Distinct tau prion strains propagate in cells and mice and define different tauopathies. Neuron (2014), 82, 1271-1288.
Sarnowski, M. P., et al. Peptide N-Amination Supports β-Sheet Conformations. Angew. Chem. Int. Ed. (2017), 56, 2083-2086.
Sarnowski, M. P., et al. Synthesis and beta-sheet propensity of constrained N-amino peptides. Bioorg. Med. Chem. (2018), 26, 1162-1166.
Sawaya, M. R., et al. Atomic structures of amyloid cross-β spines reveal varied steric zippers. Nature (2007), 447, 453-457.
Seidler, P. M., et al. "Structure-based inhibitors of tau aggregation." Nature chemistry 10.2 (2018): 170-176.
Seidler, P. M., et al. Structure-based inhibitors halt prion-like seeding by Alzheimer's disease-and tauopathy-derived brain tissue samples. J. Biol. Chem. (2019), 294, 16451-16464.
Sievers, S. A., et al.. Structure-based design of non-natural amino-acid inhibitors of amyloid fibril formation. Nature (2011), 475, 96-100.
Spillantini, M. G., et al. Tau pathology and neurodegeneration. Lancet Neurol. (2013), 12, 609-622.
Stöhr, J., et al. A 31-residue peptide induces aggregation of tau's microtubule-binding region in cells. Nat. Chem. (2017), 9, 874-881.
Tillett, K. C. et al. "N-Amino peptide scanning reveals inhibitors of Aβ 42 aggregation." RSC advances 10.24 (2020): 14331-14336.
Von Bergen, M., et al. Assembly of tau protein into Alzheimer paired helical filaments depends on a local sequence motif ((306)VQIVYK(311)) forming beta structure. Proc. Natl. Acad. Sci. U S A (2000), 97, 5129-5134.
Von Bergen, M., et al. Mutations of tau protein in frontotemporal dementia promote aggregation of paired helical filaments by enhancing local beta-structure. J. Biol. Chem. (2001), 276, 48165-48174.
Wang, C. K., et al. Inhibition of tau aggregation using a naturally-occurring cyclic peptide scaffold. Eur. J. Med. Chem. (2016), 109, 342-349.
Watkins, A. M., et al. Anatomy of beta-strands at protein-protein interfaces. ACS Chem. Biol. (2014), 9, 1747-1754.
Weingarten, M. D., et al. A protein factor essential for microtubule assembly. Proc. Natl. Acad. Sci. U S A (1975), 72, 1858-1862.
Wischik, C. M., et al. Isolation of a fragment of tau derived from the core of the paired helical filament of Alzheimer disease. Proc. Natl. Acad. Sci. U S A (1988), 85, 4506-4510.
Wischik, C. M., et al. Structural characterization of the core of the paired helical filament of Alzheimer disease. Proc. Natl. Acad. Sci. U S A (1988), 85, 4884-4888.
Wood, J. G., et al. Neurofibrillary tangles of Alzheimer disease share antigenic determinants with the axonal microtubule-associated protein tau (tau). Proc. Natl. Acad. Sci. U S A (1986), 83, 4040-4043.
Yamada, K., et al. In Vivo Microdialysis Reveals Age-Dependent Decrease of Brain Interstitial Fluid Tau Levels in P301S Human Tau Transgenic Mice. J. Neurosci. (2011), 31, 13110.
Zhang, X., et al. Selection of a d-Enantiomeric Peptide Specifically Binding to PHF6 for Inhibiting Tau Aggregation in Transgenic Mice. ACS Chem. Neurosci. (2020), 11, 4240-4253.
Zheng, J., et al. Macrocyclic β-Sheet Peptides That Inhibit the Aggregation of a Tau-Protein-Derived Hexapeptide. J. Am. Chem. Soc. (2011), 133, 3144-3157.

* cited by examiner

FIG. 2A

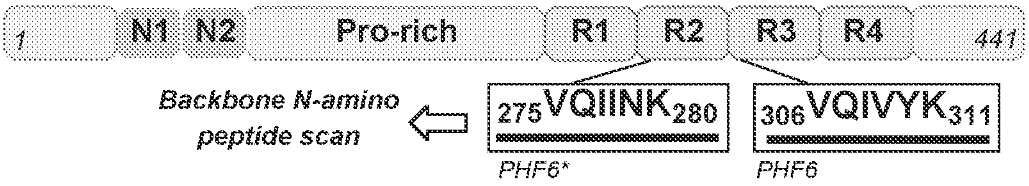

FIG. 2B

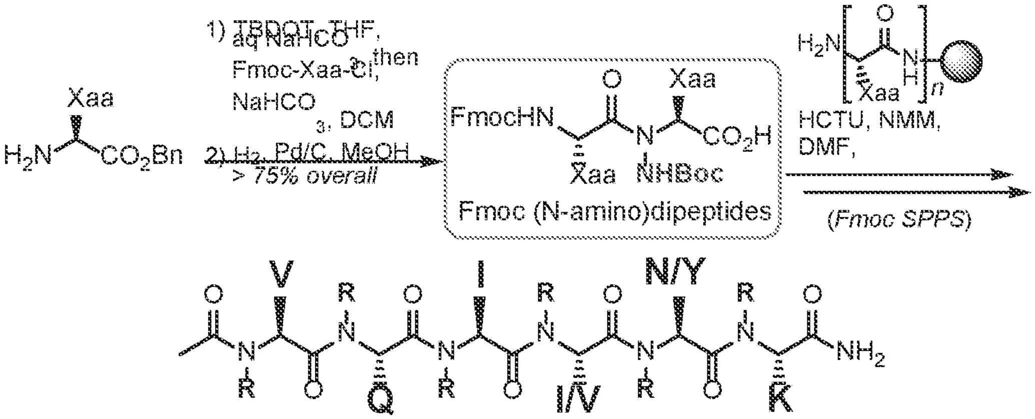

| | cmpd | sequence | $[M+H]^+_{obs}$ |
|---|---|---|---|
| EG02 | **1** | Ac-**aVal**-Gln-Ile-Ile-Asn-Lys-$NH_2$ | 770.4877 |
| EG01 | **2** | Ac-Val-Gln-**aIle**-Ile-Asn-Lys-$NH_2$ | 770.4878 |
| EF09 | **3** | Ac-Val-Gln-Ile-**aIle**-Asn-Lys-$NH_2$ | 770.4879 |
| EG05 | **4** | Ac-**aVal**-Gln-**aIle**-Ile-Asn-Lys-$NH_2$ | 820.5045 |
| EF05 | **5** | Ac-**aVal**-Gln-Ile-Val-Tyr-Lys-$NH_2$ | 805.4930 |
| EF04 | **6** | Ac-Val-Gln-**aIle**-Val-Tyr-Lys-$NH_2$ | 805.4925 |
| EE04 | **7** | Ac-Val-Gln-Ile-**aVal**-Tyr-Lys-$NH_2$ | 805.4927 |
| EE03 | **8** | Ac-Val-Gln-Ile-Val-**aTyr**-Lys-$NH_2$ | 805.4927 |
| EE06 | **9** | Ac-Val-Gln-Ile-Val-Tyr-**aLys**-$NH_2$ | 805.4933 |
| EG07 | **10** | Ac-**aVal**-Gln-**aIle**-Val-Tyr-Lys-$NH_2$ | 820.5045 |
| EG06 | **11** | Ac-**aVal**-Gln-Ile-Val-**aTyr**-Lys-$NH_2$ | 820.5041 |
| EG09 | **12** | Ac-Val-Gln-**aIle**-Val-**aTyr**-Lys-$NH_2$ | 820.5048 |
| EG08 | **13** | Ac-Val-Gln-Ile-**aVal**-Tyr-**aLys**-$NH_2$ | 820.5039 |
| EH02 | **14** | Ac-**aVal**-Gln-**aIle**-Val-**aTyr**-Lys-$NH_2$ | 835.5115 |
| EF06 | **AcPHF6*** | Ac-Val-Gln-Ile-Ile-Asn-Lys-$NH_2$ | 755.4775 |
| EE02 | **AcPHF6** | Ac-Val-Gln-Ile-Val-Tyr-Lys-$NH_2$ | 790.4833 |

No Tau No heparin Treated Tau

Tau infection with 0.19 μM of Tau P301L Fibrils

Tau infection with 0.19 μM Tau + EG05 1.9 μM

Tau infection with 0.19 μM Tau + EG05 0.009 μM

Tau infection with 0.19 μM Tau + EG08 1.9 μM

Tau infection with 0.19 μM Tau + EG08 0.009 μM

Tau infection with 0.19 μM Tau + EG09 1.9 μM

Tau infection with 0.19 μM Tau + EG09 0.009 μM

MODIFIED PEPTIDES FOR THE INHIBITION OF ABNORMAL TAU ACCUMULATION

CROSS-REFERENCE TO RELATED APPLICATIONS

This application is a U.S. national stage entry of International Patent Application No. PCT/US2022/026110, filed on Apr. 25, 2022, which claims priority to U.S. Provisional Patent Application No. 63/179,350, filed on Apr. 25, 2021, the entire contents of each of which are fully incorporated herein by reference.

FEDERALLY SPONSORED RESEARCH

This invention was made with government support under grant number CHE 2021265 awarded by the National Science Foundation. The government has certain rights in the invention.

REFERENCE TO SEQUENCE LISTING

This application is filed with a Computer Readable Form of a Sequence Listing in accord with 37 C.F.R. § 1.821 (c). The text file submitted by EFS, "092012-9146-US02 sequence listing 26-JUL-2023_ST25," was created on Jul. 26, 2023, contains 22 sequences, has a file size of 27.3 Kbytes, and is hereby incorporated by reference in its entirety.

TECHNICAL FIELD

Described herein are N-amino peptides (NAPs) that inhibit disease-associated tau aggregation and prevent fibril formation. The NAPs are derived from the R2 and R3 domains of tau (VQIINK and VQIVYK, respectively) wherein the amide moiety is N-aminated. N-amination of the R2 and R3 domains of tau results in formation of soluble mimics of ordered β-strands that are aggregation resistant and can assemble into layered parallel β-sheets.

BACKGROUND

The higher-order assembly of proteins rich in β structure is correlated with poor prognosis in several neurodegenerative diseases. Intracellular accumulation of the tau protein into neurofibrillary tangles (NFTs) is linked to cognitive dysfunction in over 20 disorders collectively termed "tauopathies." The normal function of tau is to stabilize microtubules (MTs), the support structures in axons. Pathogenic misfolding and aggregation of tau can be caused by mutations in the MAPT gene or by aberrant post-translational modifications. While toxicity has been associated with various forms of aggregated tau, current data supports oligomeric species as a primary driver of neuronal death. It is now accepted that tau pathology becomes self-perpetuating, with the capacity to spread from neuron to neuron and cause normal tau to become misfolded (FIG. 1A). Controlling the processes that govern tau fibrillization and cellular propagation is critical for understanding the progression of tauopathies.

Tau is an intrinsically disordered protein harboring up to four MT-binding repeat domains (R1-R4) in the C-terminal half. See e.g., NCBI Reference Sequence No. NP_005901.2 and SEQ ID NO: 1-2 for the human tau isoform 2 (0N4R) wild type nucleotide and polypeptide sequences, respectively. Like many amyloidogenic proteins, tau fibrillization involves conformational reorganization into β-rich folds, followed by supramolecular assembly into layered parallel β-sheets (FIG. 1A). This assembly is driven by favorable H-bonding and hydrophobic interactions between well-defined aggregation-prone hexapeptide motifs in the R2 ($^{275}$VQIINK$^{280}$; PHF6*; SEQ ID NO: 5) and R3 ($^{306}$VQIVYK$^{311}$; PHF6; SEQ ID NO: 6) domains, which are also essential for MT binding. Short peptide models have long been used to study the structure and function of tau aggregates in vitro. Direct inhibitors of tau fibrillization are largely limited to dyes and other redox-active aromatic compounds. The aggregation-prone R2/R3 segments have more recently been used in the structure-based design of modified peptides that inhibit the aggregation of a PHF6 hexapeptide or truncated forms of recombinant tau. One group recently described a series of peptides capable of blocking the aggregation of full-length tau and as well as its cellular transmission. Conformationally rigid and proteolytically stable peptidomimetics may hold particular promise as ligands of tau and other amyloid proteins that are inherently difficult to target in a sequence-specific manner.

Despite examples of peptidomimetic disruptors of β-sheet-mediated protein interactions, strategies to translate conformationally extended peptide leads into inhibitors remain limited. This is due in part to the inherent flexibility of short peptide sequences, coupled with the large surface areas and diverse modes of β-sheet interactions. The propensity for conformationally extended peptides to aggregate via exposed H-bonding edges presents another significant challenge in the design of soluble β-strand mimics. Presentation of a β-strand epitope for protein recognition typically relies on the templating effect of an auxiliary β-strand (as in linear and macrocyclic β-hairpins), intra-strand conformational restriction through covalent tethering, or backbone amide N-alkylation to preclude strand self-aggregation. While backbone amide substitution allows for retention of side chain information, N-methylation (or incorporation of Pro) can promote main chain torsions incompatible with β-sheet mimicry. An approach for β-strand stabilization was recently described based on peptide backbone N-amination (FIG. 1B). The conformational and non-aggregating characteristics of N-amino peptides (NAPs) are consistent across distinct models of β-sheet folding and are attributed to cooperative non-covalent interactions involving the Nα—$NH_2$ substituent.

What is needed is an approach to target β-rich amyloids by inhibiting disease-associated tau aggregation and preventing fibril formation.

SUMMARY

One embodiment described herein is a compound of formula (I), or a pharmaceutically acceptable salt thereof, (I)

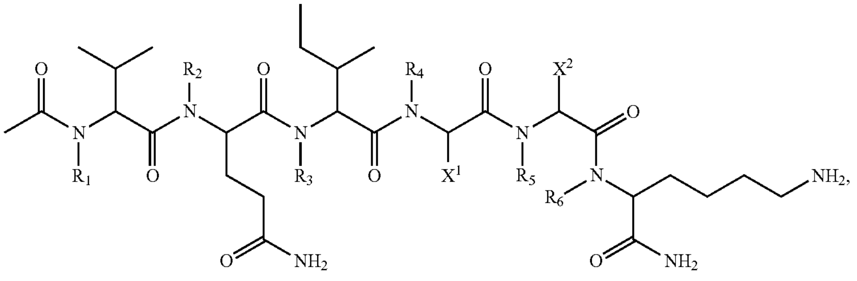

wherein:

$X^1$ is

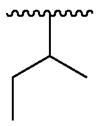

or

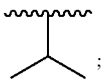

;

$X^2$ is

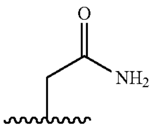

or

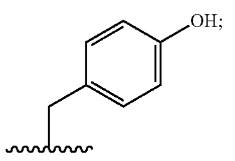

$R^1$, $R^2$, $R^3$, $R^4$, $R^5$, and $R^6$, at each occurrence, are each independently hydrogen or —$NHR^7$, with the proviso that at least one of $R^1$, $R^2$, $R^3$, $R^4$, $R^5$, and $R^6$ is not hydrogen;

$R^7$, at each occurrence, is independently hydrogen, $C_{1-6}$alkyl, $C_{1-6}$haloalkyl, $C_{1-6}$hydroxyalkyl, —$C_{1-3}$alkylene-$OR^{1a}$, —$C(O)R^{1a}$, —$CO_2R^{1a}$, —$C(O)NR^{1b}R^{1c}$, —$SO_2R^{1a}$, $G^1$, —$C(O)G^1$, —$CO_2G^1$, —$C(O)NR^{1b}G^1$, —$SO_2G^1$, —$C_{1-3}$alkylene-$G^1$, —C(O)—$C_{1-3}$alkylene-$G^1$, —$CO_2$—$C_{1-3}$alkylene-$G^1$, —$C(O)NR^{1b}$—$C_{1-3}$alkylene-$G^1$, or —$SO_2$—$C_{1-3}$alkylene-$G^1$;

$R^{1a}$, $R^{1b}$, and $R^{1c}$, at each occurrence, are each independently hydrogen, $C_{1-6}$alkyl, $C_{1-6}$haloalkyl, $C_{1-6}$hydroxyalkyl, —$C_{1-3}$alkylene-$OC_{1-6}$alkyl, $C_{3-8}$cycloalkyl, or —$C_{1-3}$alkylene-$C_{3-8}$cycloalkyl, wherein the $C_{3-8}$cycloalkyl in $R^{1a}$, $R^{1b}$, and $R^{1c}$ is optionally substituted with 1-4 substituents independently selected from halogen, $C_{1-4}$alkyl, and $C_{1-4}$haloalkyl;

$G^1$ is a 6- to 12-membered aryl, a 5- to 12-membered heteroaryl containing 1-2 heteroatoms, or a 3- to 12-membered carbocyclyl, wherein $G^1$ is optionally substituted with 1-5 substituents, each independently halogen, cyano, $R^x$, —$OR^x$, —$C_{1-3}$alkylene-$OR^x$, —$N(R^x)_2$, —$C(O)R^x$, —$CO_2R^x$, —$C(O)N(R^x)_2$, or —$SO_2R^x$; and $R^x$ at each occurrence, is independently $C_{1-4}$alkyl, $C_{1-4}$haloalkyl, $C_{1-6}$hydroxyalkyl, $C_{3-8}$cycloalkyl, or —$C_{1-3}$alkylene-$C_{3-8}$cycloalkyl, wherein the $C_{3-8}$cycloalkyl in $R^x$ is optionally substituted with 1-4 substituents, each independently selected from halogen, $C_{1-4}$alkyl, and $C_{1-4}$haloalkyl.

In one aspect, $R^7$ is hydrogen, $C_{1-6}$alkyl, —$C(O)R^{1a}$, —$CO_2R^{1a}$, —$SO_2G^1$, —$C_{1-3}$alkylene-$G^1$, or —$CO_2$—$C_{1-3}$ alkylene-$G^1$. In another aspect, $G^1$ is the optionally substituted 6- to 12-membered aryl. In another aspect, the ring system of the optionally substituted 6- to 12-membered aryl is a phenyl. In another aspect, $R^7$ is hydrogen or —$CO_2C_{1-6}$ alkyl. In another aspect, $X^1$ is

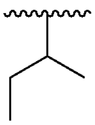 [SMILES: *C(C)CC]

and $X^2$ is

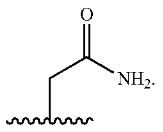 [SMILES: *CC(N)=O]

In another aspect, $X^1$ is

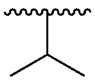

and $X^2$ is

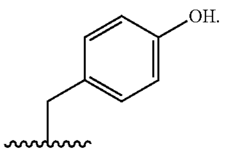 [SMILES: *Cc1ccc(O)cc1]

In another aspect, $R^1$ is —$NHR^7$ and $R^2$, $R^3$, $R^4$, $R^5$, and $R^6$ are each hydrogen. In another aspect, $R^3$ is —$NHR^7$ and $R^1$, $R^2$, $R^4$, $R^5$, and $R^6$ are each hydrogen. In another aspect, $R^4$ is —$NHR^7$, and $R^1$, $R^2$, $R^3$, $R^5$, and $R^6$ are each hydrogen. In another aspect, $R^5$ is —$NHR^7$, and $R^1$, $R^2$, $R^3$, $R^4$, and $R^6$ are each hydrogen. In another aspect, $R^6$ is —$NHR^7$, and $R^1$, $R^2$, $R^3$, $R^4$, and $R^5$ are each hydrogen. In another aspect, $R^1$ and $R^3$ are each —$NHR^7$, and $R^2$, $R^4$, $R^5$, and $R^6$ are each hydrogen. In another aspect, $R^1$ and $R^5$ are each —$NHR^7$, and $R^2$, $R^3$, $R^4$, and $R^6$ are each hydrogen. In another aspect, $R^3$ and $R^5$ are each —$NHR^7$, and $R^1$, $R^2$, $R^4$, and $R^6$ are each hydrogen. In another aspect, $R^4$ and $R^6$ are each —$NHR^7$, and $R^1$, $R^2$, $R^3$, and $R^5$ are each hydrogen. The compound of any one of clauses 1-7, or a pharmaceutically acceptable salt thereof, wherein $R^1$, $R^3$, and $R^5$ are each —$NHR^7$, and $R^2$, $R^4$, and $R^6$ are each hydrogen. In another aspect, the compound is a compound of formula (I-a), (I-a)

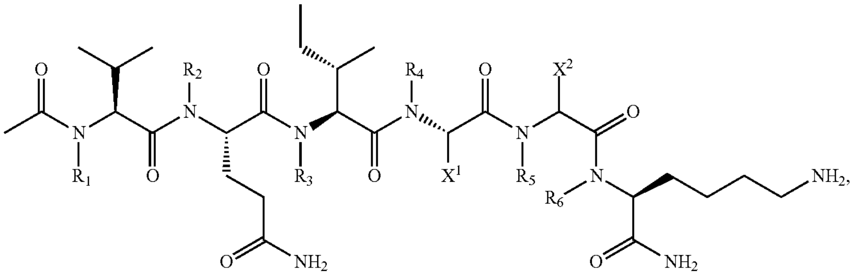

or a pharmaceutically acceptable salt thereof, wherein: $X^1$ is

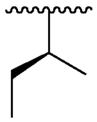

or

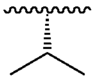

and $X^2$ is

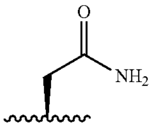

or

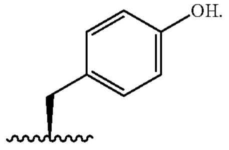

In another aspect, the compound is selected from:

(SEQ ID NO: 7)

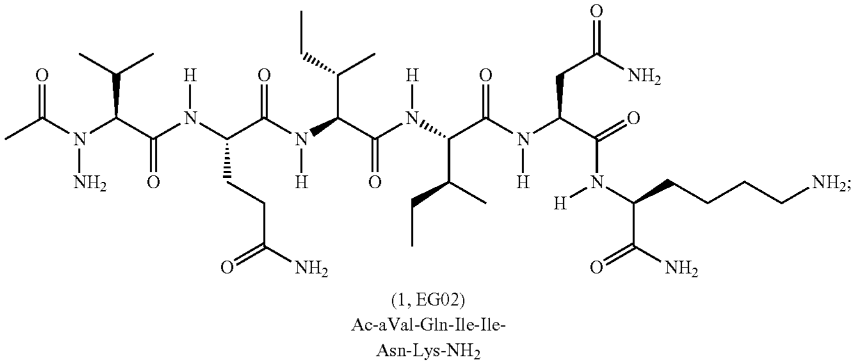

(1, EG02)
Ac-aVal-Gln-Ile-Ile-Asn-Lys-$NH_2$

-continued
(SEQ ID NO: 8)
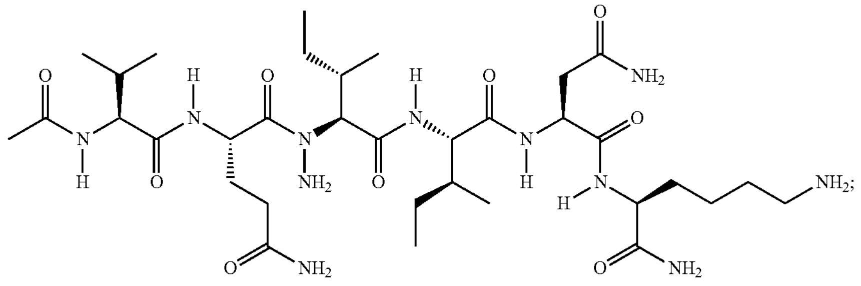
(2, EG01)
Ac-Val-Gln-aIle-Ile-
Asn-Lys-$NH_2$
(SEQ ID NO: 9)
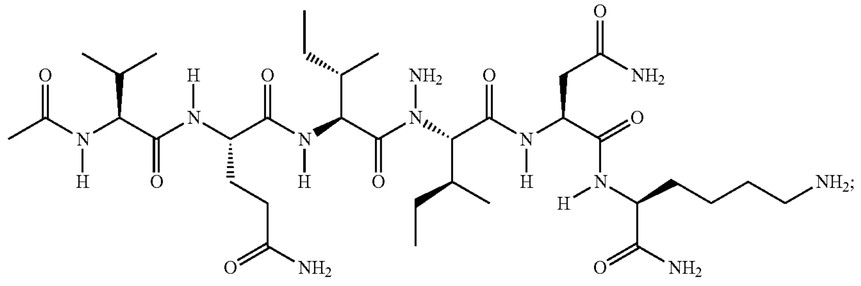
(3, EG09)
Ac-Val-Gln-Ile-aIle-
Asn-Lys-$NH_2$
(SEQ ID NO: 10)
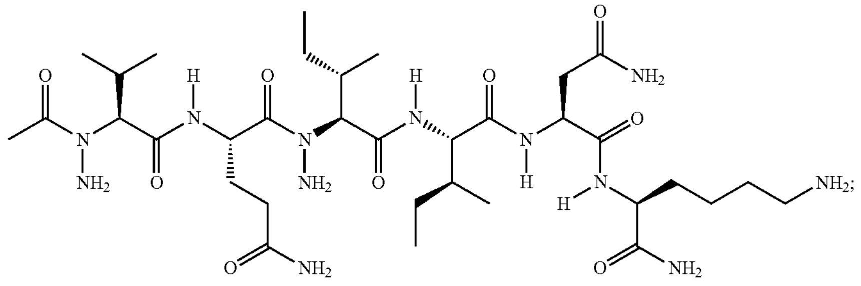
(4, EG05)
Ac-aVal-Gln-aIle-
Ile-Asn-Lys-$NH_2$
(SEQ ID NO: 11)
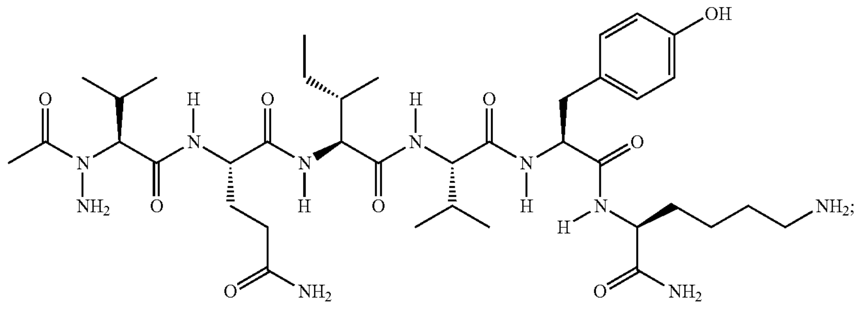
(5, EF05)
Ac-aVal-Gln-Ile-
Val-Tyr-Lys-$NH_2$ -continued
(SEQ ID NO: 12)
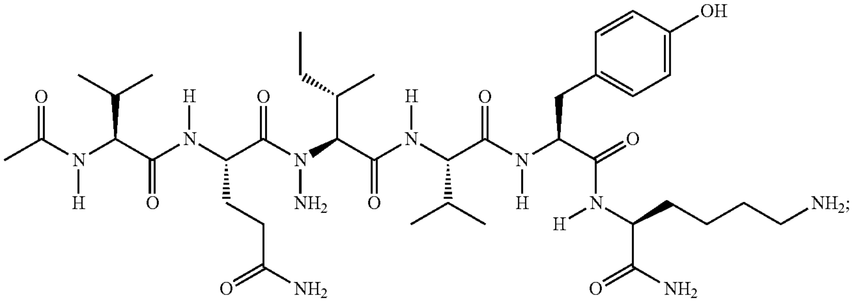
(6, EF04)
Ac-Val-Gln-aIle-
Val-Tyr-Lys-$NH_2$
(SEQ ID NO: 13)
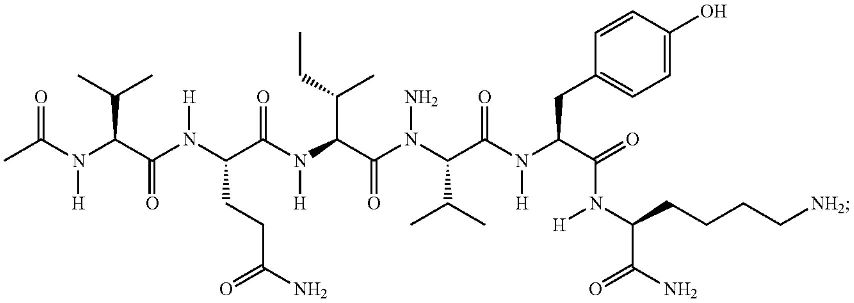
(7, EE04)
Ac-Val-Gln-Ile-
aVal-Tyr-Lys-$NH_2$
(SEQ ID NO: 14)
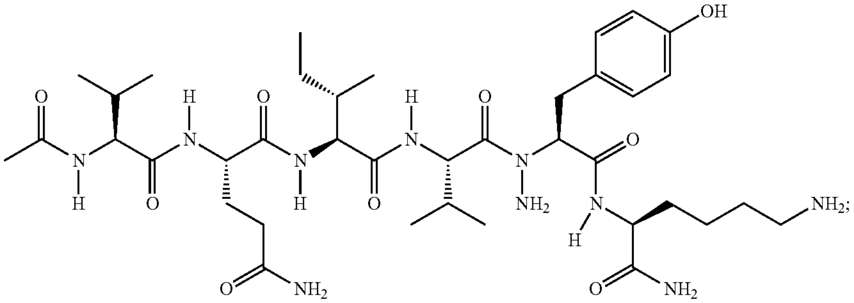
(8, EE03)
Ac-Val-Gln-Ile-Val-
aTyr-Lys-$NH_2$
(SEQ ID NO: 15)
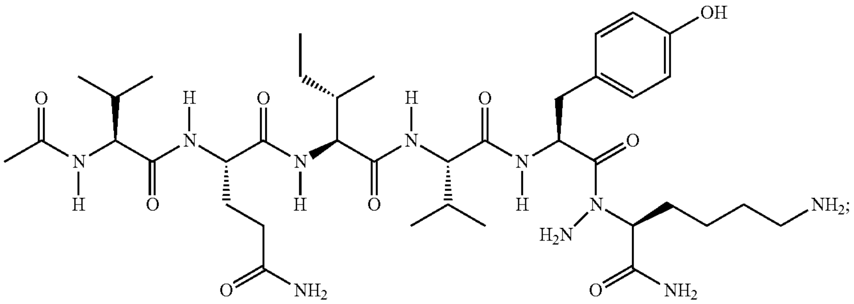
(9, EE06)
Ac-Val-Gln-Ile-Val-
Tyr-aLys-$NH_2$ -continued
(SEQ ID NO: 16)
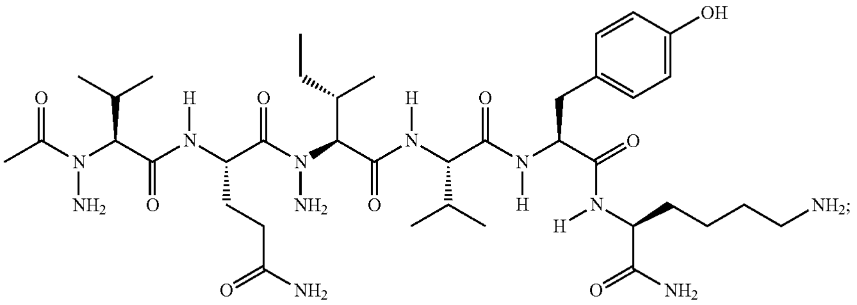
(10, EG07)
Ac-aVal-Gln-aIle-
Val-Tyr-Lys-$NH_2$
(SEQ ID NO: 17)
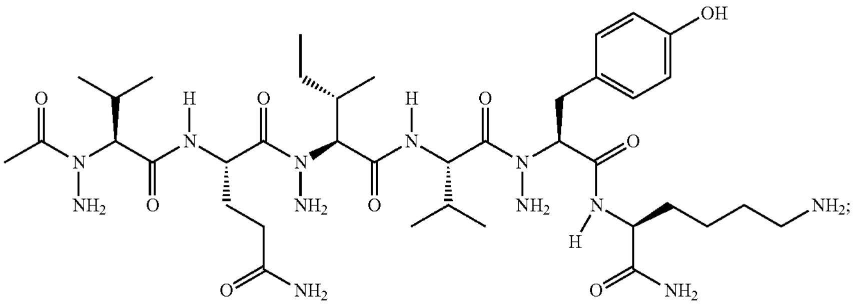
(11, EG06)
Ac-aVal-Gln-Ile-
Val-aTyr-Lys-$NH_2$
(SEQ ID NO: 18)
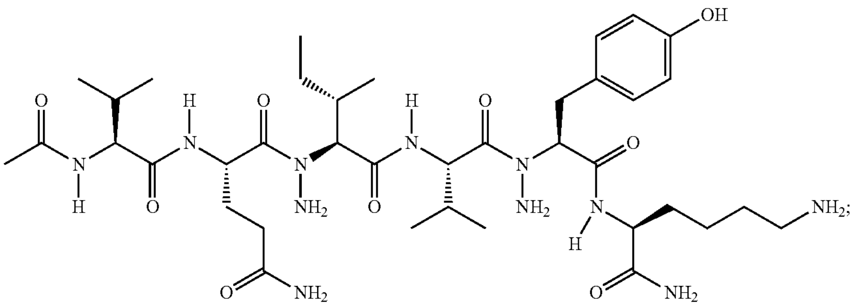
(12, EG09)
Ac-Val-Gln-aIle-
Val-aTyr-Lys-$NH_2$
(SEQ ID NO: 19)
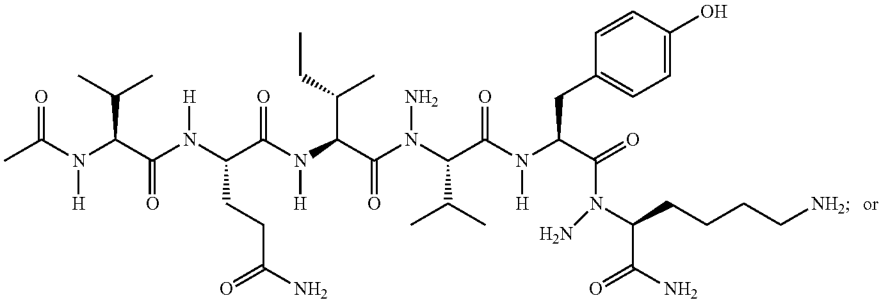
(13, EG08)
Ac-Val-Gln-aIle-
aVal-Tyr-aLys-$NH_2$ -continued (SEQ ID NO: 20)

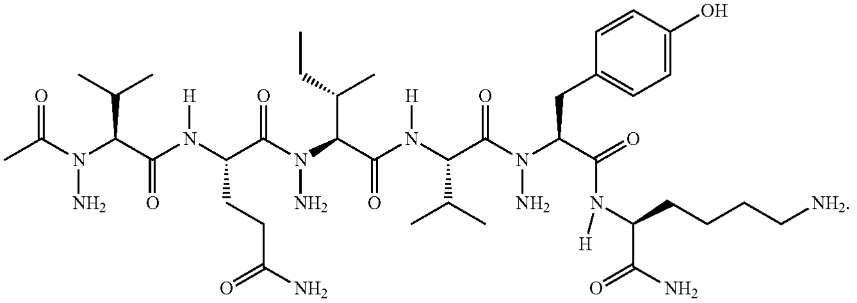

(14, EH02)
Ac-aVal-Gln-aIle-
Val-aTyr-Lys-$NH_2$

In another aspect, the compound is stable in human blood, serum, plasma, or cerebrospinal fluid. In another aspect, the compound is non-toxic to human neuronal cells Another embodiment described herein is a method for inhibiting tau protein fibrillization or aggregation, the method comprising contacting tau protein with one or more compounds described herein. In one aspect, the compounds comprise one or more of compounds 1-14 (SEQ ID NO: 7-20). In another aspect, the compounds comprise one or more of compounds 12 or 13 (SEQ ID NO: 18 or 19). In another aspect, the compounds have a concentration of at least 2-fold molar excess over the tau protein's concentration.

Another embodiment described herein is a method for preventing cellular transmission of neurofibrillary tangles (NFTs), the method comprising contacting cells containing NFTs with one or more compounds of the compounds described herein. In one aspect, the compounds comprise one or more of Compounds 1-14 (SEQ ID NO: 7-20). In another aspect, the compounds comprise one or more of Compounds 12 or 13 (SEQ ID NO: 18 or 19). In another aspect, the compounds have a concentration of about 2-5 μM.

DESCRIPTION OF THE DRAWINGS

(FIG. 1B) N-Amino peptides (NAP) mimics of aggregation-prone peptides.

FIG. 2A-B show an N-amino peptide scan of tau hexapeptides. FIG. 2A shows aggregation-prone tau parent sequences. FIG. 2B shows NAP analogues of PHF6 and PHF6* prepared by SPPS. The nucleotide and polypeptide sequences for human tau (0N4R) mutant, P301L, which was used for these studies is provided in SEQ ID NO: 3-4, respectively.

FIG. 5A shows of the 14 tested N-amino inhibitors we found 6 when incubated at two-fold molar excess (Tau 10 μM: Inhibitor 20 μM), significantly reduced the ThT fluorescence up to 50%, indicative of inhibiting Tau aggregation. These inhibitors also interfered with the rapid aggregation kinetics and overall reduced the total amount of amyloids formed over the course of 48 h. FIG. 5B-C show that other inhibitors were found to be in-effective at inhibiting Tau aggregation in the ThT assay. FIG. 5D shows that N-amino substitution completely abolished the aggregation propensity of the two hexapeptide amyloid forming motifs as evident by significant reduction in ThT fluorescence values: about 14000 and 1700 fold less, see compounds AcPHF6 (EE02; SEQ ID NO: 22) and AcPHF6* (EF06; SEQ ID NO: 21) respectively, as compared with inhibitor compound 5 (EG05; SEQ ID NO: 11), 13 (EG08; SEQ ID NO: 19), 2 (EG01; SEQ ID NO: 8), 4 (EGOS; SEQ ID NO: 10), 13 (EG08; SEQ ID NO: 19), and 12 (EG09; SEQ ID NO: 18).

FIG. 7A shows representative micrographs of HEK293 cells stably expressing tau-RD (P301L/V337M)-YFP, when seeded with blank buffer (No Tau) and with non-fibrillized Tau (no heparin treated Tau). No punctuates observed was clear evidence of the assay's robustness and specificity. FIG. 7B shows representative micrographs of HEK293 cells stably expressing tau-RD (P301L/V337M)-YFP, when seeded with 0.19 μM of Tau (heparin treated Tau). Exposure of fibrillized Tau resulted in aggregation of endogenous tau-RD (P301L/V337M)-YFP seen as focal punctuates with high fluorescence. Large number of observed punctuates was a clear evidence of Tau seeding or also called as Tau infection and assay's sensitivity. FIG. 7C-D show representative micrographs of HEK293 cells stably expressing tau-RD, when seeded with 0.19 μM of heparin treated Tau and compound 4 (EG05; SEQ ID NO: 10) at 1.9 μM (FIG. 7C) or 0.9 μM (FIG. 7D). FIG. 7E-F show representative micrographs of HEK293 cells stably expressing tau-RD, when seeded with 0.19 μM of heparin treated Tau and compound 13 (EG08; SEQ ID NO: 19) at 1.9 μM (FIG. 7E) or 0.9 μM (FIG. 7F). FIG. 7G-H show representative micrographs of HEK293 cells stably expressing tau-RD, when seeded with 0.19 μM of heparin treated Tau and compound 12 (EG09; SEQ ID NO: 18) at 1.9 μM (FIG. 7G) or 0.9 μM (FIG. 7H).

FIG. 9A shows more than 80% of compound 13 (EG08; SEQ ID NO: 19) and 12 (EG09; SEQ ID NO: 18) was found to be intact after 24 h in 25% human serum whereas control peptide was digested more than 90%. FIG. 9B shows the cytotoxic effect of compounds 13 (EG08; SEQ ID NO: 19) and 12 (EG09; SEQ ID NO: 18) at low (10 μM) and high (50 μM) concentration with an incubation time of 48 h, was evaluated using MTT assay on human neuroblastoma SH-SY5Y cell line and was found to be non-cytotoxic FIG. 10 shows solution NMR-derived structural ensemble of 12 (EG09; SEQ ID NO: 18).

DETAILED DESCRIPTION

Figure 1A:
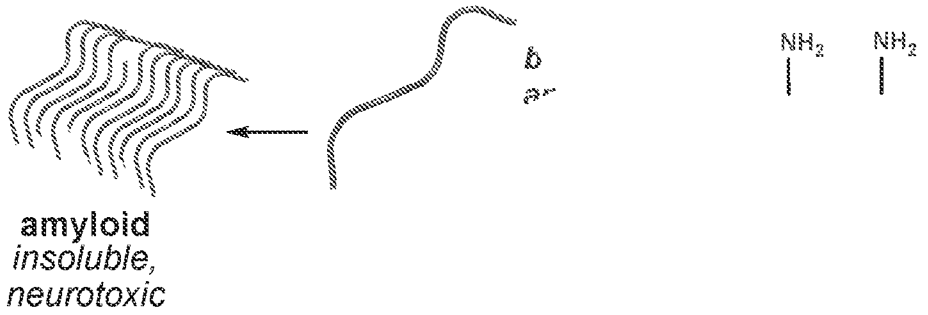
FIG. 1A-B show (FIG. 1A) a tau fibril highlighting the cross-β sidechain interactions of PHF6 and parallel β-sheet stacking and the cellular propagation of tau NFTs from neuron to neuron.
Figure 1B:
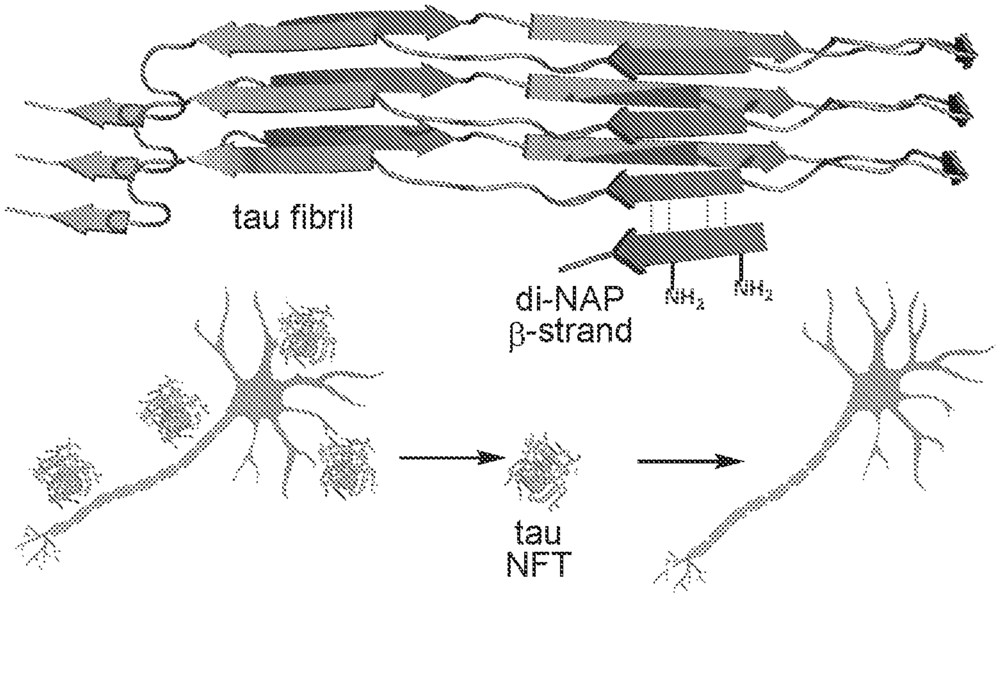

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present disclosure, including definitions, will control. Exemplary methods and materials are described below, although methods and materials similar or equivalent to those described herein can be used in practice or testing of the embodiments and aspects described herein.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "active ingredient" or "active pharmaceutical ingredient" refer to a pharmaceutical agent, active ingredient, compound, or substance, compositions, or mixtures thereof, that provide a pharmacological, often beneficial, effect.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "dose" denotes any form of an active ingredient formulation or composition, including cells, that contains an amount sufficient to initiate or produce a therapeutic effect with at least one or more administrations. "Formulation" and "composition" are used interchangeably herein.

As used herein, the term "prophylaxis" refers to preventing or reducing the progression of a disorder, either to a statistically significant degree or to a degree detectable by a person of ordinary skill in the art.

As used herein, the terms "effective amount" or "therapeutically effective amount," refers to a substantially non-toxic, but sufficient amount of an action, agent, composition, or cell(s) being administered to a subject that will prevent, treat, or ameliorate to some extent one or more of the symptoms of the disease or condition being experienced or that the subject is susceptible to contracting. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a primate. In one embodiment, the subject is a human.

As used herein, a subject is "in need of treatment" if such subject would benefit biologically, medically, or in quality of life from such treatment. A subject in need of treatment does not necessarily present symptoms, particular in the case of preventative or prophylaxis treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest.

The spread of neurofibrillary tangles resulting from tau protein aggregation is a hallmark of Alzheimer's and related neurodegenerative diseases. Early oligomerization of tau involves conformational reorganization into parallel β-sheet structures and supramolecular assembly into toxic fibrils. Despite the need for selective inhibitors of tau propagation, β-rich protein assemblies are inherently difficult to target with small molecules.

Described herein is a minimalist approach to mimic the aggregation-prone modules within tau. A backbone residue scan was carried out and showed that amide N-amination completely abolishes the tendency of these peptides to self-aggregate, rendering them soluble mimics of ordered β-strands from the tau R2 and R3 domains. Several N-amino peptides (NAPs) inhibit disease-associated tau aggregation and prevent fibril formation in vitro. NAPs 12 and 13 are further demonstrated to be effective at blocking the cellular seeding of endogenous tau by both monomeric and fibrillar forms of extracellular tau. Peptidomimetic 12 is serum stable, non-toxic to neuronal cells, and selectivity inhibits the aggregation of tau over Aβ42. Structural analysis of lead NAPs shows considerable conformational constraint imposed by the N-amino groups. The enhanced rigidity and full complement of sidechains within NAPs thus enables tau fibril recognition. The described backbone N-amination approach thus provides a rational basis for the mimicry of other aggregation-prone peptides that drive pathogenic protein assembly.

One embodiment described herein is a compound of formula (I), or a pharmaceutically acceptable salt thereof, (I)

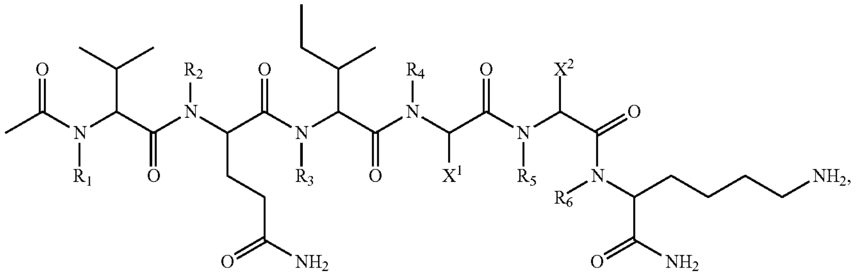

wherein:

$X^1$ is

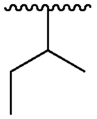 or 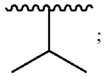 ;

$X^2$ is

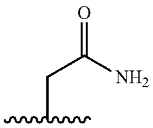 or 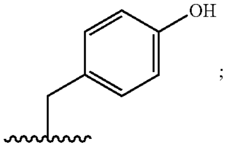 ;

$R^1$, $R^2$, $R^3$, $R^4$, $R^5$, and $R^6$, at each occurrence, are each independently hydrogen or —$NHR^7$, with the proviso that at least one of $R^1$, $R^2$, $R^3$, $R^4$, $R^5$, and $R^6$ is not hydrogen;

$R^7$, at each occurrence, is independently hydrogen, $C_{1-6}$alkyl, $C_{1-6}$haloalkyl, $C_{1-6}$hydroxyalkyl, —$C_{1-3}$alkylene-$OR^{1a}$, —$C(O)R^{1a}$, —$CO_2R^{1a}$, —$C(O)NR^{1b}R^{1c}$, —$SO_2R^{1a}$, $G^1$, —$C(O)G^1$, —$CO_2G^1$, —$C(O)NR^{1b}G^1$, —$SO_2G^1$, —$C_{1-3}$alkylene-$G^1$, —C(O)—$C_{1-3}$alkylene-$G^1$, —$CO_2$—$C_{1-3}$alkylene-$G^1$, —$C(O)NR^{1b}$—$C_{1-3}$alkylene-$G^1$, or —$SO_2$—$C_{1-3}$alkylene-$G^1$;

$R^{1a}$, $R^{1b}$, and $R^{1c}$, at each occurrence, are each independently hydrogen, $C_{1-6}$alkyl, $C_{1-6}$haloalkyl, $C_{1-6}$hydroxyalkyl, —$C_{1-3}$alkylene-$OC_{1-6}$alkyl, $C_{3-8}$cycloalkyl, or —$C_{1-3}$alkylene-$C_{3-8}$cycloalkyl, wherein the $C_{3-8}$cycloalkyl in $R^{1a}$, $R^{1b}$, and $R^{1c}$ is optionally substituted with 1-4 substituents independently selected from halogen, $C_{1-4}$alkyl, and $C_{1-4}$haloalkyl;

$G^1$ is a 6- to 12-membered aryl, a 5- to 12-membered heteroaryl containing 1-2 heteroatoms, or a 3- to 12-membered carbocyclyl, wherein $G^1$ is optionally substituted with 1-5 substituents, each independently halogen, cyano, $R^x$, —$OR^x$, —$C_{1-3}$alkylene-$OR^x$, —$N(R)_2$, —$C(O)R^x$, —$CO_2R^x$, —$C(O)N(R^x)_2$, or —$SO_2R^x$; and $R^x$ at each occurrence, is independently $C_{1-4}$alkyl, $C_{1-4}$haloalkyl, $C_{1-6}$hydroxyalkyl, $C_{3-8}$cycloalkyl, or —$C_{1-3}$alkylene-$C_{3-8}$cycloalkyl, wherein the $C_{3-8}$cycloalkyl in $R^x$ is optionally substituted with 1-4 substituents, each independently selected from halogen, $C_{1-4}$alkyl, and $C_{1-4}$haloalkyl.

In one aspect, $R^7$ is hydrogen, $C_{1-6}$alkyl, —$C(O)R^{1a}$, —$CO_2R^{1a}$, —$SO_2G^1$, —$C_{1-3}$alkylene-$G^1$, or —$CO_2$—$C_{1-3}$ alkylene-$G^1$. In another aspect, $G^1$ is the optionally substituted 6- to 12-membered aryl. In another aspect, the ring system of the optionally substituted 6- to 12-membered aryl is a phenyl. In another aspect, $R^7$ is hydrogen or —$CO_2C_{1-6}$ alkyl. In another aspect, $X^1$ is

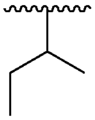 [SMILES: *C(C)CC]

and $X^2$ is

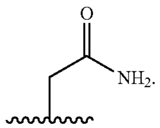 [SMILES: *CC(N)=O]

In another aspect, $X^1$ is

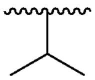

and $X^2$ is

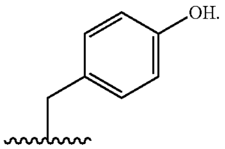 [SMILES: *Cc1ccc(O)cc1]

In another aspect, $R^1$ is —$NHR^7$ and $R^2$, $R^3$, $R^4$, $R^5$, and $R^6$ are each hydrogen. In another aspect, $R^3$ is —$NHR^7$ and $R^1$, $R^2$, $R^4$, $R^5$, and $R^6$ are each hydrogen. In another aspect, $R^4$ is —$NHR^7$, and $R^1$, $R^2$, $R^3$, $R^5$, and $R^6$ are each hydrogen. In another aspect, $R^5$ is —$NHR^7$, and $R^1$, $R^2$, $R^3$, $R^4$, and $R^6$ are each hydrogen. In another aspect, $R^6$ is —$NHR^7$, and $R^1$, $R^2$, $R^3$, $R^4$, and $R^5$ are each hydrogen. In another aspect, $R^1$ and $R^3$ are each —$NHR^7$, and $R^2$, $R^4$, $R^5$, and $R^6$ are each hydrogen. In another aspect, $R^1$ and $R^5$ are each —$NHR^7$, and $R^2$, $R^3$, $R^4$, and $R^6$ are each hydrogen. In another aspect, $R^3$ and $R^5$ are each —$NHR^7$, and $R^1$, $R^2$, $R^4$, and $R^6$ are each hydrogen. In another aspect, $R^4$ and $R^6$ are each —$NHR^7$, and $R^1$, $R^2$, $R^3$, and $R^5$ are each hydrogen. The compound of any one of clauses 1-7, or a pharmaceutically acceptable salt thereof, wherein $R^1$, $R^3$, and $R^5$ are each —$NHR^7$, and $R^2$, $R^4$, and $R^6$ are each hydrogen. In another aspect, the compound is a compound of formula (I-a), (I-a)

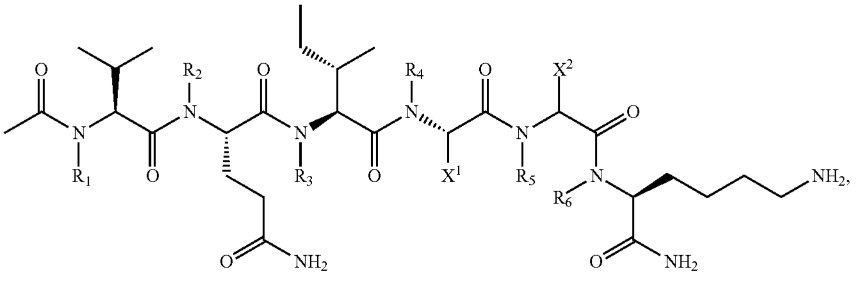

or a pharmaceutically acceptable salt thereof, wherein: $X^1$ is

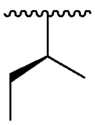

or

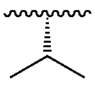

and $X^2$ is

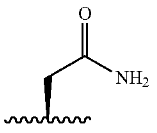

or

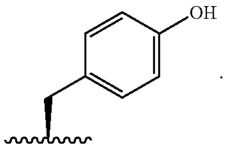

.

In another aspect, the compound is selected from:

(SEQ ID NO: 7)

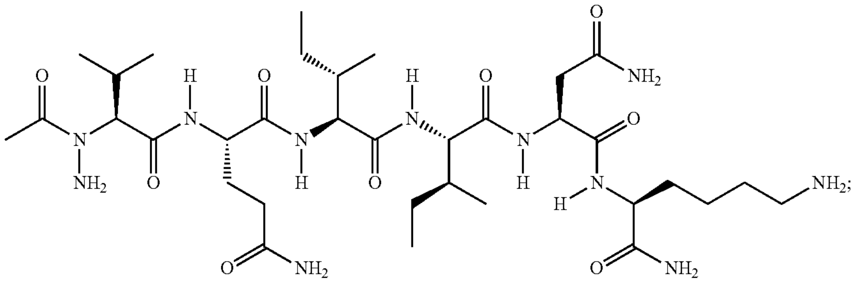

(1, EG02)
Ac-aVal-Gln-Ile-Ile-Asn-Lys-$NH_2$ (SEQ ID NO: 8)

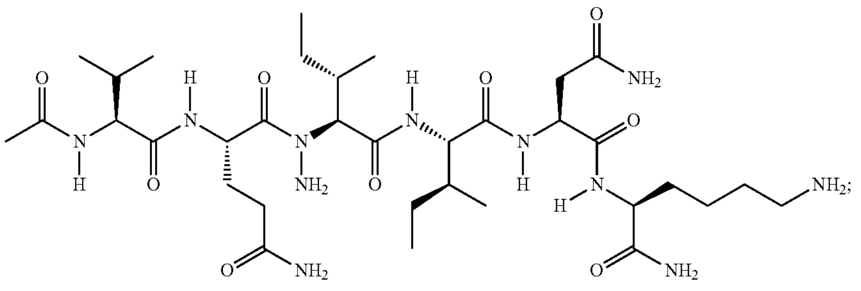

(2, EG01)
Ac-Val-Gln-aIle-Ile-Asn-Lys-$NH_2$

-continued
(SEQ ID NO: 9)
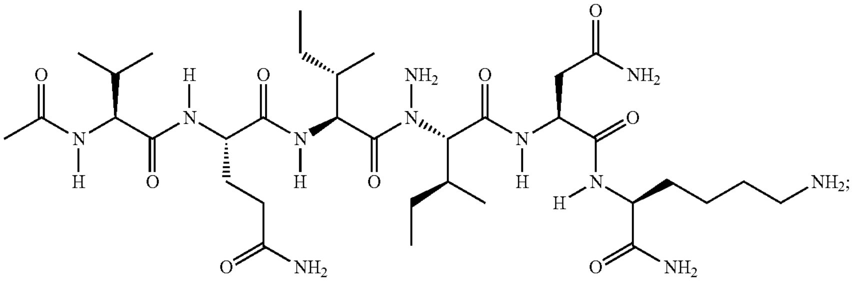
(3, EG09)
Ac-Val-Gln-Ile-aIle-
Asn-Lys-$NH_2$
(SEQ ID NO: 10)
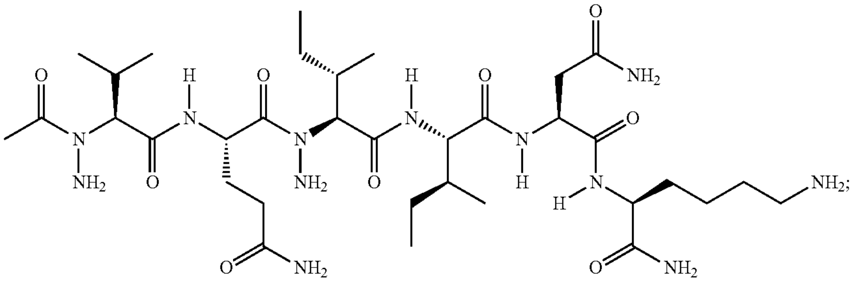
(4, EG05)
Ac-aVal-Gln-aIle-
Ile-Asn-Lys-$NH_2$
(SEQ ID NO: 11)
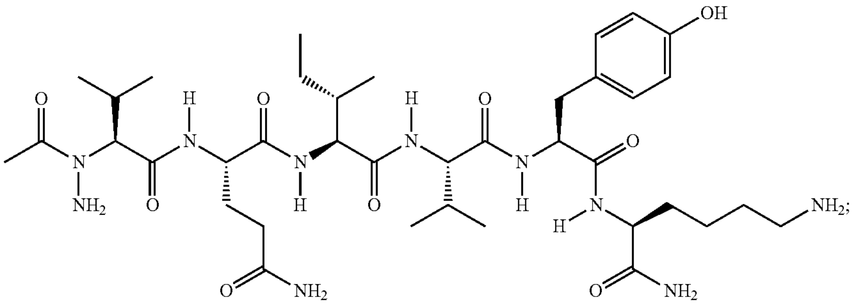
(5, EF05)
Ac-aVal-Gln-Ile-
Val-Tyr-Lys-$NH_2$
(SEQ ID NO: 12)
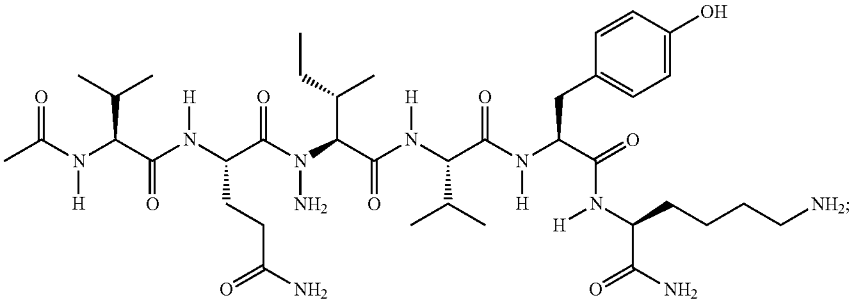
(6, EF04)
Ac-Val-Gln-aIle-
Val-Tyr-Lys-$NH_2$ -continued
(SEQ ID NO: 13)
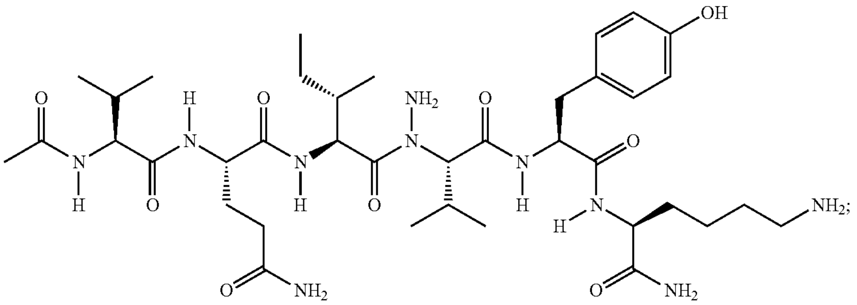
(7, EE04)
Ac-Val-Gln-Ile-
aVal-Tyr-Lys-$NH_2$
(SEQ ID NO: 14)
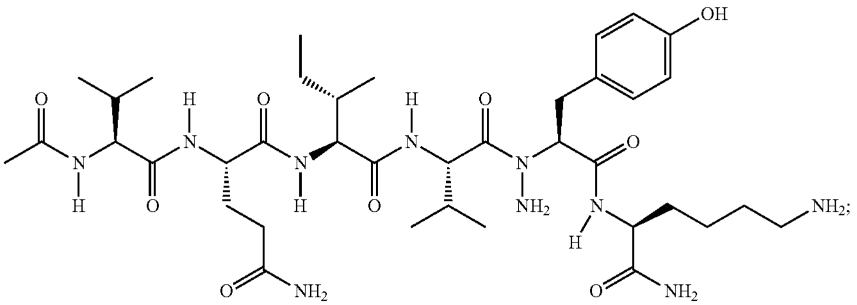
(8, EE03)
Ac-Val-Gln-Ile-Val-
aTyr-Lys-$NH_2$
(SEQ ID NO: 15)
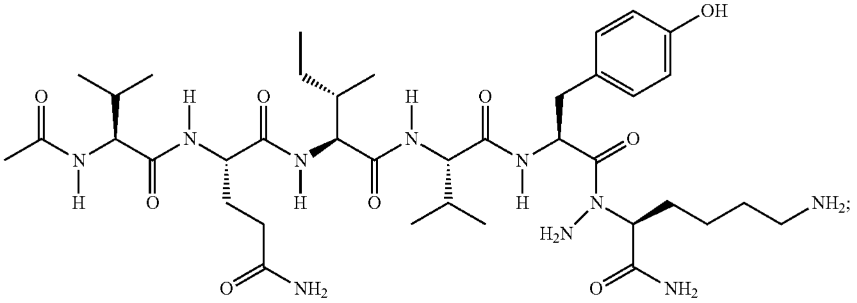
(9, EE06)
Ac-Val-Gln-Ile-Val-
Tyr-aLys-$NH_2$
(SEQ ID NO: 16)
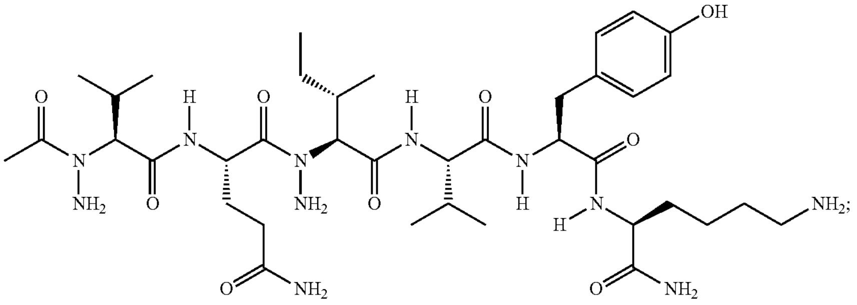
(10, EG07)
Ac-aVal-Gln-alle-
Val-Tyr-Lys-$NH_2$ -continued
(SEQ ID NO: 17)
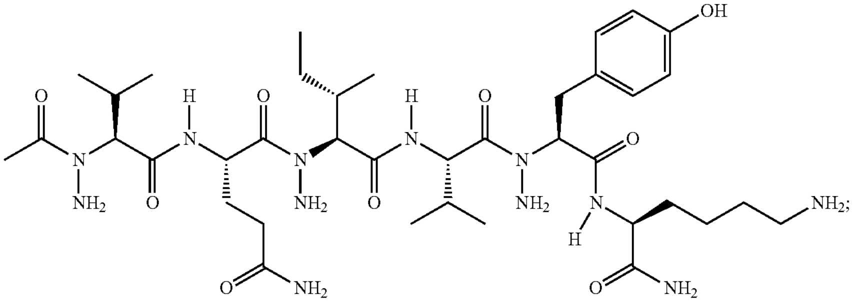
(11, EG06)
Ac-aVal-Gln-Ile-
Val-aTyr-Lys-$NH_2$
(SEQ ID NO: 18)
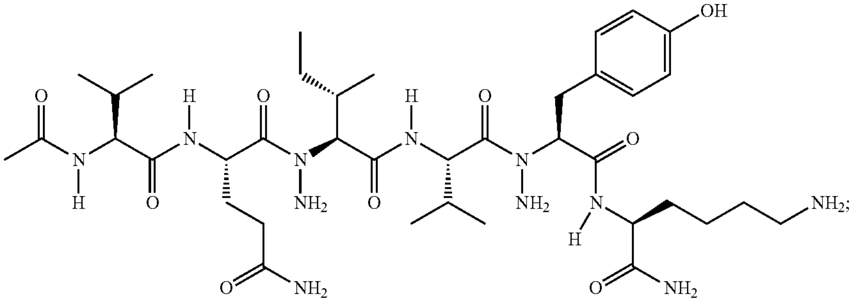
(12, EG09)
Ac-Val-Gln-aIle-
Val-aTyr-Lys-$NH_2$
(SEQ ID NO: 19)
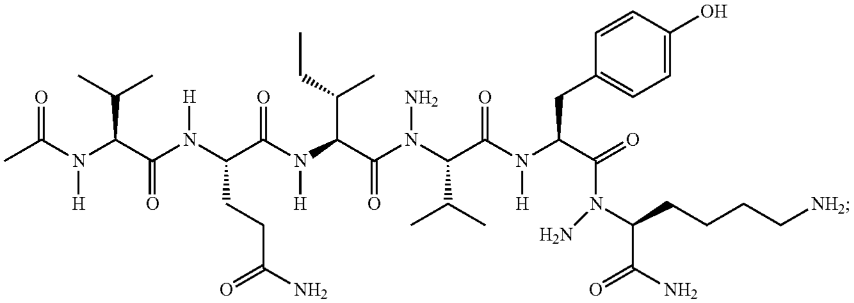
or
(13, EG08)
Ac-Val-Gln-aIle-
aVal-Tyr-aLys-$NH_2$
(SEQ ID NO: 20)
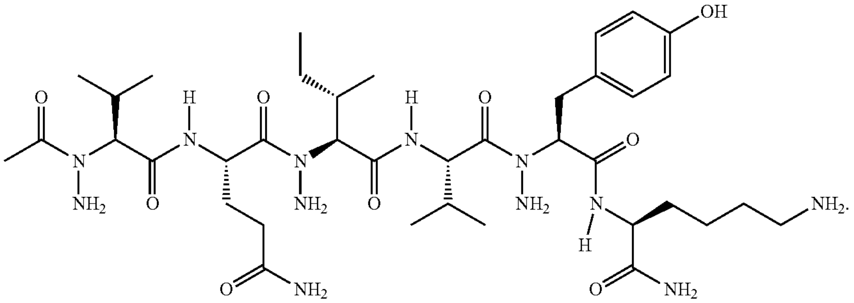
(14, EH02)
Ac-aVal-Gln-aIle-
Val-aTyr-Lys-$NH_2$ In another aspect, the compound is stable in human blood, serum, plasma, or cerebrospinal fluid. In another aspect, the compound is non-toxic to human neuronal cells Another embodiment described herein is a method for inhibiting tau protein fibrillization or aggregation, the method comprising contacting tau protein with one or more compounds described herein. In one aspect, the compounds comprise one or more of compounds 1-14 (SEQ ID NO: 7-20). In another aspect, the compounds comprise one or more of compounds 12 or 13 (SEQ ID NO: 18 or 19). In another aspect, the compounds have a concentration of at least 2-fold molar excess over the tau protein's concentration.

Another embodiment described herein is a method for preventing cellular transmission of neurofibrillary tangles (NFTs), the method comprising contacting cells containing NFTs with one or more compounds of the compounds described herein. In one aspect, the compounds comprise one or more of Compounds 1-14 (SEQ ID NO: 7-20). In another aspect, the compounds comprise one or more of Compounds 12 or 13 (SEQ ID NO: 18 or 19). In another aspect, the compounds have a concentration of about 2-5 μM.

Fragments, derivatives, or analogs of the polypeptides of SEQ ID NO: 7-20 can be (i) ones in which one or more of the amino acid residues (e.g., 1, 2, 3, 4, 5, or 6 residues, or even more) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 1, 2, 3, 4, 5, or 6 residues or even more), or (iii) ones in which the mature polypeptide is fused with another polypeptide or compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

In addition, fragments, derivatives, or analogs of the polypeptides of SEQ ID NO: 7-20 can be substituted with one or more conserved or non-conserved amino acid residue (preferably a conserved amino acid residue). In some cases these polypeptides, fragments, derivatives, or analogs thereof will have a polypeptide sequence at least 50%, 55%, 60%, 65%, 70%, 75%, 80%, 85%, 90%, 91%, 92%, 93%, 94%, 95%, 96%, 97%, 98%, 99% or 100% identical to the polypeptide sequence shown in SEQ ID NO: 7-20 and will comprise functional or non-functional proteins or enzymes. Similarly, additions or deletions to the polypeptides can be made either at the N- or C-termini or within non-conserved regions of the polypeptide (which are assumed to be non-critical because they have not been photogenically conserved).

As described herein, in many cases the amino acid substitutions, mutations, additions, or deletions are preferably of a minor nature, such as conservative amino acid substitutions that do not significantly affect the folding or activity of the protein or additions or deletions to the N- or C-termini. Of course, the number of amino acid substitutions, additions, or deletions a skilled artisan would make depends on many factors, including those described herein. Generally, the number of substitutions, additions, or deletions for any given polypeptide will not be more than about 4, 3, 2, or 1.

TABLE 1

Peptide Compounds

Val-Gln-Ile-Ile-Asn-Lys
($V_{275}QIINK_{280}$)
PHF6* (SEQ ID NO: 5)

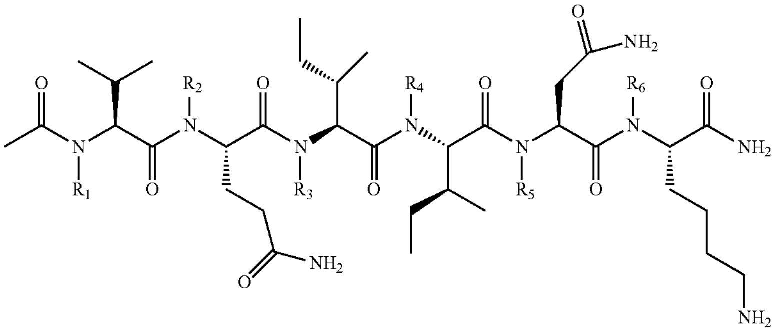

| Cmpd | SEQ ID NO | Sequence | $R^1$ | $R^2$ | $R^3$ | $R^4$ | $R^5$ | $R^6$ |
|---|---|---|---|---|---|---|---|---|
| 1 (EG02) | 7 | Ac-aVal-Gln-Ile-Ile-Asn-Lys-$NH_2$ | $NH_2$ | H | H | H | H | H |
| 2 (EG01) | 8 | Ac-Val-Gln-aIle-Ile-Asn-Lys-$NH_2$ | H | H | $NH_2$ | H | H | H |
| 3 (EG09) | 9 | Ac-Val-Gln-Ile-aIle-Asn-Lys-$NH_2$ | H | H | H | $NH_2$ | H | H |
| 4 (EG05) | 10 | Ac-aVal-Gln-aIle-Ile-Asn-Lys-$NH_2$ | $NH_2$ | H | $NH_2$ | H | H | H |
| AcPHF6* | 21 | Ac-Val-Gln-Ile-Ile-Asn-Lys-$NH_2$ | H | H | H | H | H | H |

TABLE 1-continued

| Peptide Compounds |
|---|
| Val-Gln-Ile-Val-Tyr-Lys<br>($V_{306}QIVNK_{311}$)<br>PHF6 (SEQ ID NO: 6) |

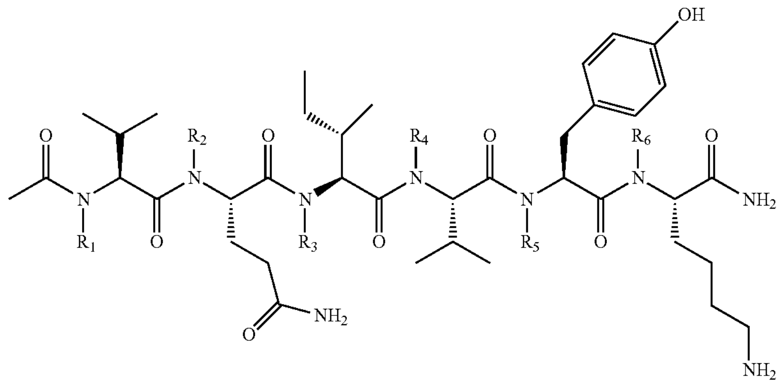

| Cmpd | SEQ ID NO | Sequence | $R^1$ | $R^2$ | $R^3$ | $R^4$ | $R^5$ | $R^6$ |
|---|---|---|---|---|---|---|---|---|
| 5 (EF05) | 11 | Ac-aVal-Gln-Ile-Val-Tyr-Lys-$NH_2$ | $NH_2$ | H | H | H | H | H |
| 6 (EF04) | 12 | Ac-Val-Gln-alle-Val-Tyr-Lys-$NH_2$ | H | H | $NH_2$ | H | H | H |
| 7 (EE04) | 13 | Ac-Val-Gln-Ile-aVal-Tyr-Lys-$NH_2$ | H | H | H | $NH_2$ | H | H |
| 8 (EE03 | 14 | Ac-Val-Gln-Ile-Val-aTyr-Lys-$NH_2$ | H | H | H | H | $NH_2$ | H |
| 9 (EE06) | 15 | Ac-Val-Gln-Ile-Val-Tyr-aLys-$NH_2$ | H | H | H | H | H | $NH_2$ |
| 10 (EG07) | 16 | Ac-aVal-Gln-alle-Val-Tyr-Lys-$NH_2$ | $NH_2$ | H | $NH_2$ | H | H | H |
| 11 (EG06) | 17 | Ac-aVal-Gln-Ile-Val-aTyr-Lys-$NH_2$ | $NH_2$ | H | H | H | $NH_2$ | M |
| 12 (EG09) | 18 | Ac-Val-Gln-alle-Val-aTyr-Lys-$NH_2$ | H | H | $NH_2$ | H | $NH_2$ | H |
| 13 (EG08) | 19 | Ac-Val-Gln-Ile-aVal-Tyr-aLys-$NH_2$ | H | H | H | $NH_2$ | H | $NH_2$ |
| 14 (EH02) | 20 | Ac-aVal-Gln-alle-Val-aTyr-Lys-$NH_2$ | $NH_2$ | H | $NH_2$ | H | $NH_2$ | H |
| AcPHF6 | 22 | Ac-Val-Gln-Ile-Val-Tyr-Lys-$NH_2$ | H | H | H | H | H | H |

aXaa refers to amination of the amine moiety.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

Various embodiments and aspects of the inventions described herein are summarized by the following clauses:

Clause 1. A compound of formula (I), or a pharmaceutically acceptable salt thereof, (I)

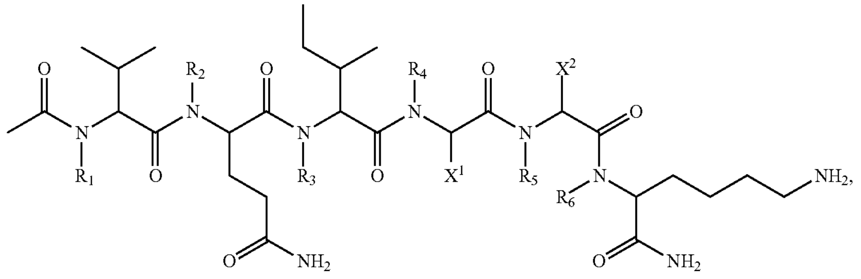

wherein:

$X^1$ is

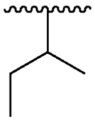 or 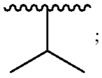 ;

$X^2$ is

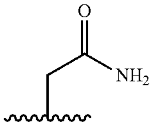 or 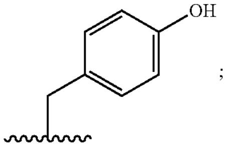 ;

$R^1$, $R^2$, $R^3$, $R^4$, $R^5$, and $R^6$, at each occurrence, are each independently hydrogen or —$NHR^7$, with the proviso that at least one of $R^1$, $R^2$, $R^3$, $R^4$, $R^5$, and $R^6$ is not hydrogen;

$R^7$, at each occurrence, is independently hydrogen, $C_{1-6}$alkyl, $C_{1-6}$haloalkyl, $C_{1-6}$hydroxyalkyl, —$C_{1-3}$alkylene-$OR^{1a}$, —$C(O)R^{1a}$, —$CO_2R^{1a}$, —$C(O)NR^{1b}R^{1c}$, —$SO_2R^{1a}$, $G^1$, —$C(O)G^1$, —$CO_2G^1$, —$C(O)NR^{1b}G^1$, —$SO_2G^1$, —$C_{1-3}$alkylene-$G^1$, —C(O)—$C_{1-3}$alkylene-$G^1$, —$CO_2$—$C_{1-3}$alkylene-$G^1$, —$C(O)NR^{1b}$—$C_{1-3}$alkylene-$G^1$, or —$SO_2$—$C_{1-3}$alkylene-$G^1$;

$R^{1a}$, $R^{1b}$, and $R^{1c}$, at each occurrence, are each independently hydrogen, $C_{1-6}$alkyl, $C_{1-6}$haloalkyl, $C_{1-6}$hydroxyalkyl, —$C_{1-3}$alkylene-$OC_{1-6}$alkyl, $C_{3-8}$cycloalkyl, or —$C_{1-3}$alkylene-$C_{3-8}$cycloalkyl, wherein the $C_{3-8}$cycloalkyl in $R^{1a}$, $R^{1b}$, and $R^{1c}$ is optionally substituted with 1-4 substituents independently selected from halogen, $C_{1-4}$alkyl, and $C_{1-4}$haloalkyl;

$G^1$ is a 6- to 12-membered aryl, a 5- to 12-membered heteroaryl containing 1-2 heteroatoms, or a 3- to 12-membered carbocyclyl, wherein $G^1$ is optionally substituted with 1-5 substituents, each independently halogen, cyano, $R^x$, —$OR^x$, —$C_{1-3}$alkylene-$OR^x$, —$N(R^x)_2$, —$C(O)R^x$, —$CO_2R^x$, —$C(O)N(R^x)_2$, or —$SO_2R^x$; and $R^x$ at each occurrence, is independently $C_{1-4}$alkyl, $C_{1-4}$haloalkyl, $C_{1-6}$hydroxyalkyl, $C_{3-8}$cycloalkyl, or —$C_{1-3}$alkylene-$C_{3-8}$cycloalkyl, wherein the $C_{3-8}$cycloalkyl in $R^x$ is optionally substituted with 1-4 substituents, each independently selected from halogen, $C_{1-4}$alkyl, and $C_{1-4}$haloalkyl.

Clause 2. The compound of clause 1, or a pharmaceutically acceptable salt thereof, wherein $R^7$ is hydrogen, $C_{1-6}$alkyl, —$C(O)R^{1a}$, —$CO_2R^{1a}$, —$SO_2G^1$, —$C_{1-3}$alkylene-$G^1$, or —$CO_2$—$C_{1-3}$alkylene-$G^1$.

Clause 3. The compound of clause 1 or 2, or a pharmaceutically acceptable salt thereof, wherein $G^1$ is the optionally substituted 6- to 12-membered aryl.

Clause 4. The compound of any one of clauses 1-3, or a pharmaceutically acceptable salt thereof, wherein the ring system of the optionally substituted 6- to 12-membered aryl is a phenyl.

Clause 5. The compound of any one of clauses 1-4, or a pharmaceutically acceptable salt thereof, wherein $R^7$ is hydrogen or —$CO_2C_{1-6}$alkyl.

Clause 6. The compound of any one of clauses 1-5, or a pharmaceutically acceptable salt thereof, wherein $X^1$ is

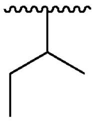 [SMILES: *C(C)CC]

and $X^2$ is

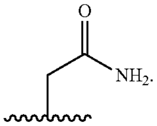 [SMILES: *CC(N)=O]

Clause 7. The compound of any one of clauses 1-6, or a pharmaceutically acceptable salt thereof, wherein $X^1$ is

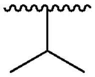 [SMILES: *C(C)C]

and $X^2$ is

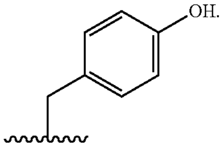 [SMILES: *Cc1ccc(O)cc1]

Clause 8. The compound of any one of clauses 1-7, or a pharmaceutically acceptable salt thereof, wherein $R^1$ is —$NHR^7$ and $R^2$, $R^3$, $R^4$, $R^5$, and $R^6$ are each hydrogen.

Clause 9. The compound of any one of clauses 1-7, or a pharmaceutically acceptable salt thereof, wherein $R^3$ is —$NHR^7$ and $R^1$, $R^2$, $R^4$, $R^5$, and $R^6$ are each hydrogen.

Clause 10. The compound of any one of clauses 1-7, or a pharmaceutically acceptable salt thereof, wherein $R^4$ is —$NHR^7$, and $R^1$, $R^2$, $R^3$, $R^5$, and $R^6$ are each hydrogen.

Clause 11. The compound of any one of clauses 1-7, or a pharmaceutically acceptable salt thereof, wherein $R^5$ is —$NHR^7$, and $R^1$, $R^2$, $R^3$, $R^4$, and $R^6$ are each hydrogen.

Clause 12. The compound of any one of clauses 1-7, or a pharmaceutically acceptable salt thereof, wherein $R^6$ is —$NHR^7$, and $R^1$, $R^2$, $R^3$, $R^4$, and $R^5$ are each hydrogen.

Clause 13. The compound of any one of clauses 1-7, or a pharmaceutically acceptable salt thereof, wherein $R^1$ and $R^3$ are each —$NHR^7$, and $R^2$, $R^4$, $R^5$, and $R^6$ are each hydrogen.

Clause 14. The compound of any one of clauses 1-7, or a pharmaceutically acceptable salt thereof, wherein $R^1$ and $R^5$ are each —$NHR^7$, and $R^2$, $R^3$, $R^4$, and $R^6$ are each hydrogen.

Clause 15. The compound of any one of clauses 1-7, or a pharmaceutically acceptable salt thereof, wherein $R^3$ and $R^5$ are each —$NHR^7$, and $R^1$, $R^2$, $R^4$, and $R^6$ are each hydrogen.

Clause 16. The compound of clause 1, or a pharmaceutically acceptable salt thereof, wherein $R^4$ and $R^6$ are each —$NHR^7$, and $R^1$, $R^2$, $R^3$, and $R^5$ are each hydrogen.

Clause 17. The compound of any one of clauses 1-7, or a pharmaceutically acceptable salt thereof, wherein $R^1$, $R^3$, and $R^5$ are each —$NHR^7$, and $R^2$, $R^4$, and $R^6$ are each hydrogen.

Clause 18. The compound of any one of clauses 1-7, wherein the compound is a compound of formula (I-a),

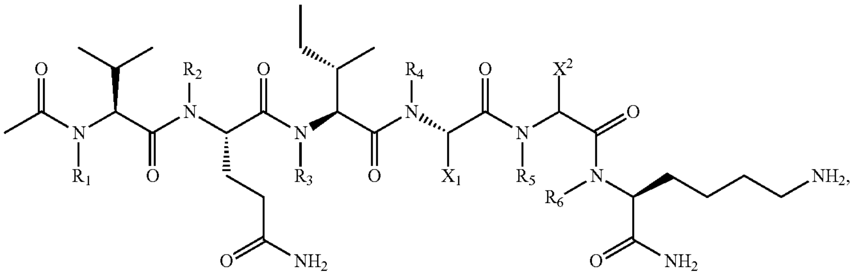

(I-a)

or a pharmaceutically acceptable salt thereof, wherein:

$X^1$ is

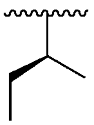

or

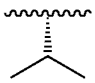

and $X^2$ is

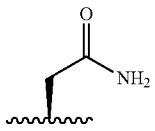

or

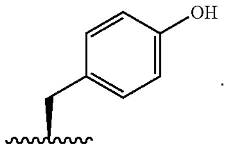

.

Clause 19. The compound of any one of clauses 1-18, wherein the compound is selected from:

(SEQ ID NO: 7)

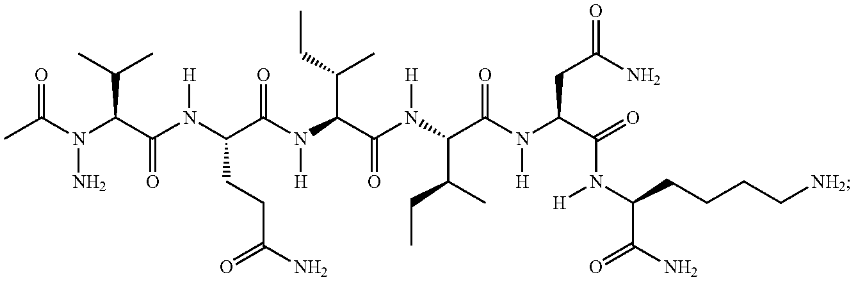

(1, EG02)
Ac-aVal-Gln-Ile-Ile-Asn-Lys-$NH_2$ (SEQ ID NO: 8)

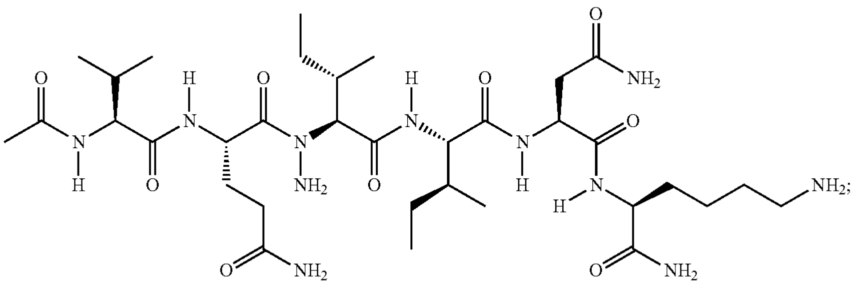

(2, EG01)
Ac-Val-Gln-aIle-Ile-Asn-Lys-$NH_2$

-continued
(SEQ ID NO: 9)
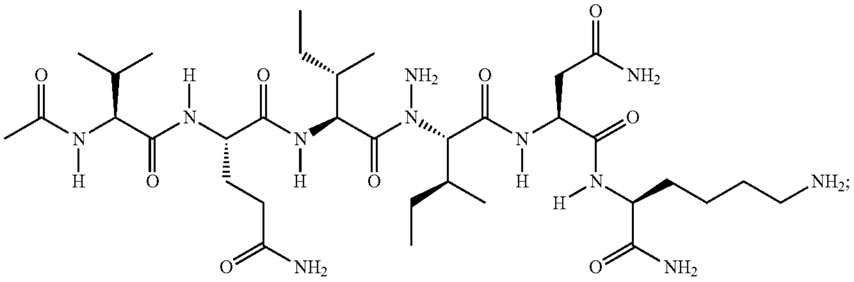
(3, EG09)
Ac-Val-Gln-Ile-alle-
Asn-Lys-$NH_2$
(SEQ ID NO: 10)
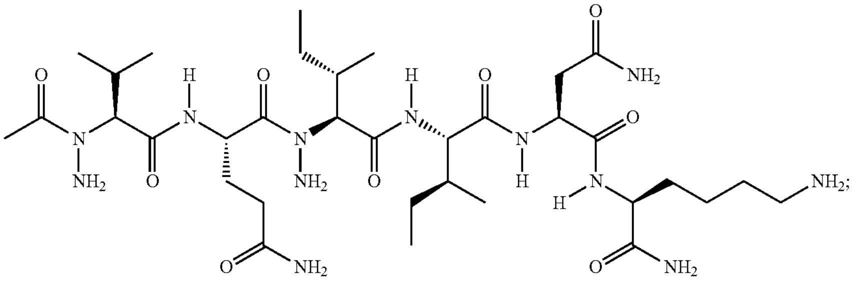
(4, EG05)
Ac-aVal-Gln-alle-
Ile-Asn-Lys-$NH_2$
(SEQ ID NO: 11)
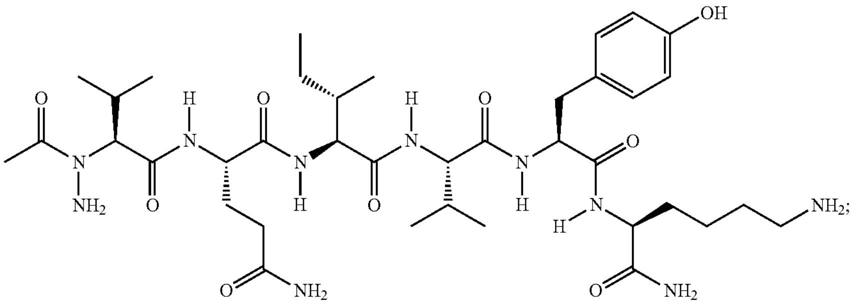
(5, EF05)
Ac-aVal-Gln-Ile-
Val-Tyr-Lys-$NH_2$
(SEQ ID NO: 12)
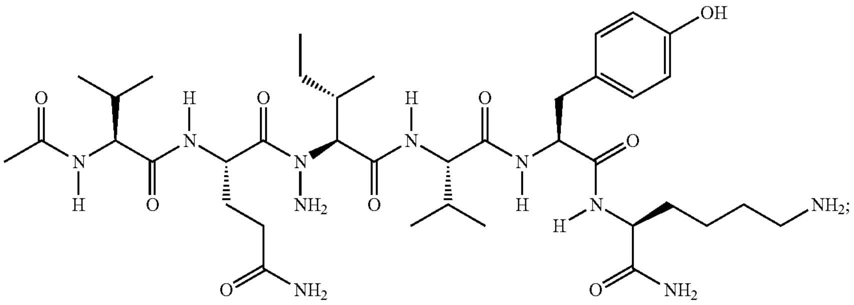
(6, EF04)
Ac-Val-Gln-alle-
Val-Tyr-Lys-$NH_2$ -continued
(SEQ ID NO: 13)
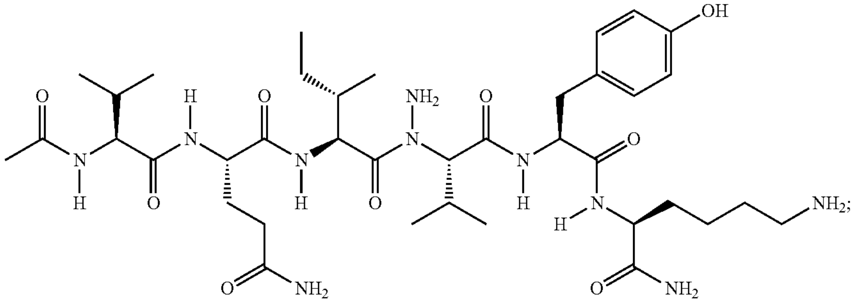
(7, EE04)
Ac-Val-Gln-Ile-aVal-Tyr-Lys-$NH_2$
(SEQ ID NO: 14)
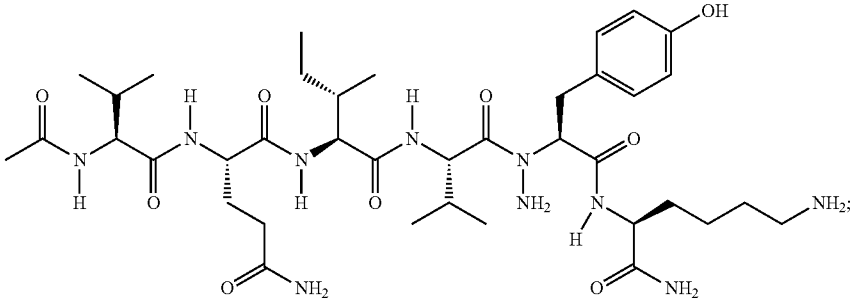
(8, EE03)
Ac-Val-Gln-Ile-Val-aTyr-Lys-$NH_2$
(SEQ ID NO: 15)
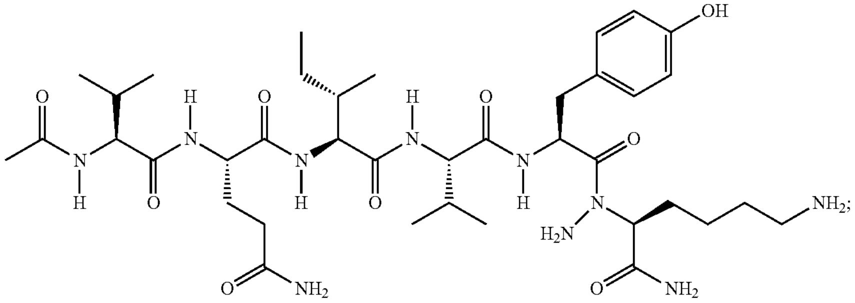
(9, EE06)
Ac-Val-Gln-Ile-Val-Tyr-aLys-$NH_2$
(SEQ ID NO: 16)
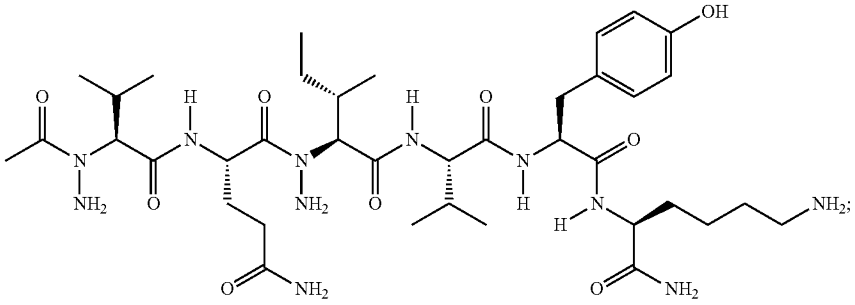
(10, EG07)
Ac-aVal-Gln-aIle-Val-Tyr-Lys-$NH_2$ -continued
(SEQ ID NO: 17)
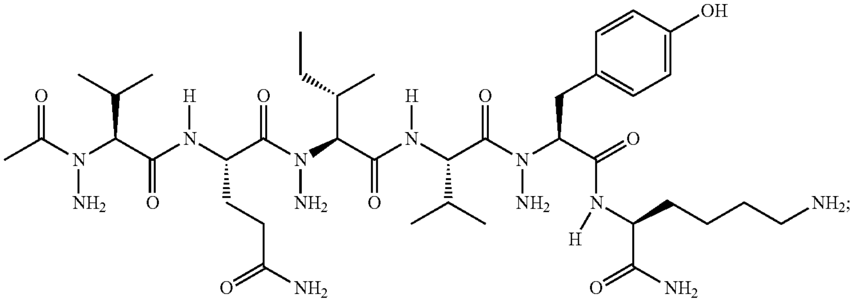
(11, EG06)
Ac-aVal-Gln-Ile-
Val-aTyr-Lys-$NH_2$
(SEQ ID NO: 18)
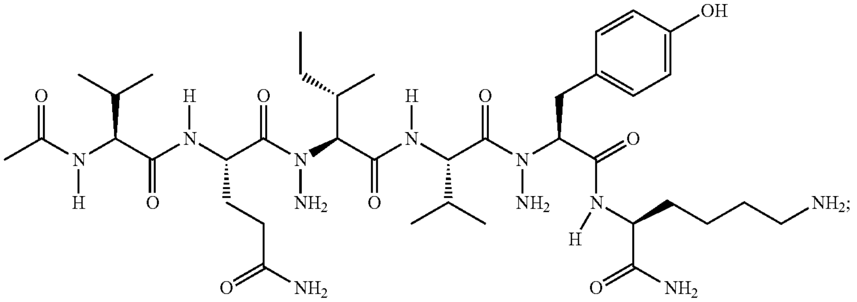
(12, EG09)
Ac-Val-Gln-aIle-
Val-aTyr-Lys-$NH_2$
(SEQ ID NO: 19)
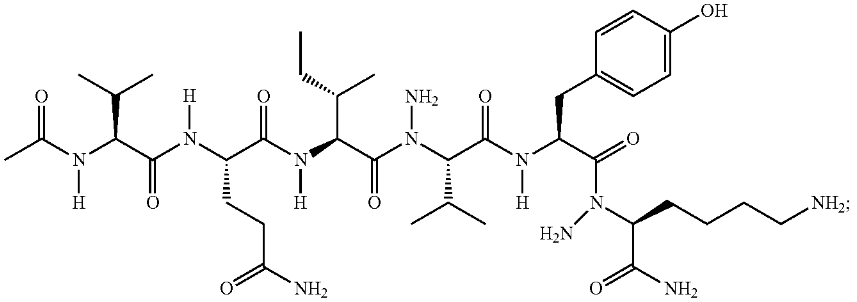
or
(13, EG08)
Ac-Val-Gln-aIle-
aVal-Tyr-aLys-$NH_2$
(SEQ ID NO: 20)
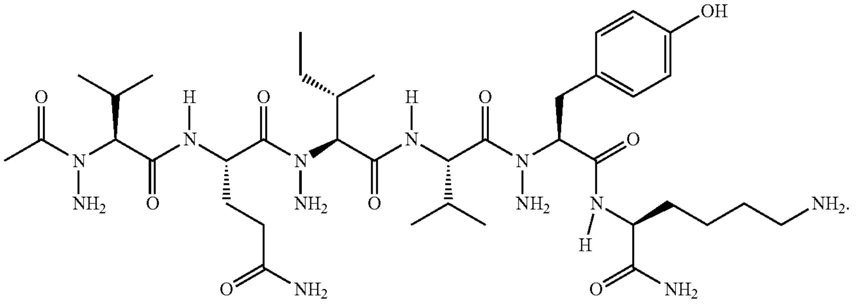
(14, EH02)
Ac-aVal-Gln-aIle-
Val-aTyr-Lys-$NH_2$ Clause 20. The compound of any one of clauses 1-19, wherein the compound is stable in human blood, serum, plasma, or cerebrospinal fluid.

Clause 21. The compound of any one of clauses 1-20, wherein the compound is non-toxic to human neuronal cells Clause 22. A method for inhibiting tau protein fibrillization or aggregation, the method comprising contacting tau protein with one or more compounds of any one of clauses 1-21.

Clause 23. The method of clause 22, wherein the compounds comprise one or more of compounds 1-14 (SEQ ID NO: 7-20).

Clause 24. The method of clause 22 or 23, wherein the compounds comprise one or more of compounds 12 or 13 (SEQ ID NO: 18 or 19).

Clause 25. The method of any one of clauses 22-24, wherein the compounds have a concentration of at least 2-fold molar excess over the tau protein's concentration.

Clause 26. A method for preventing cellular transmission of neurofibrillary tangles (NFTs), the method comprising contacting cells containing NFTs with one or more compounds of any one of clauses 1-21.

Clause 27. The method of clause 26, wherein the compounds comprise one or more of Compounds 1-14 (SEQ ID NO: 7-20).

Clause 28. The method of clause 26 or 27, wherein the compounds comprise one or more of Compounds 12 or 13 (SEQ ID NO: 18 or 19).

Clause 29. The method of any one of clauses 26-28, wherein the compounds have a concentration of about 2-5 μM.

EXAMPLES

Example 1

Chemical Synthesis

Unless stated otherwise, reactions were performed in flame-dried glassware under a positive pressure of argon or nitrogen gas using dry solvents. Commercial grade reagents and solvents were used without further purification except where noted. Anhydrous solvents were purchased directly from chemical suppliers. Thin-layer chromatography (TLC) was performed using silica gel 60 F254 pre-coated plates (0.25 mm). Flash chromatography was performed using silica gel (60 μm particle size). Reaction progress was judged by TLC analysis (single spot/two solvent systems) using a UV lamp, CAM (ceric ammonium molybdate), ninhydrin, or basic $KMnO_4$ stain(s) for detection purposes. NMR spectra were recorded on a 500 or 800 MHz spectrometer. Proton chemical shifts are reported as δ values relative to residual signals from deuterated solvents ($CDCl_3$, DMSO-$d_6$, $D_2O$).

General Procedure for N-Amino Dipeptide Synthesis

A general scheme for the preparation of substituted oxaziridines is shown in Scheme 1.

Scheme 1

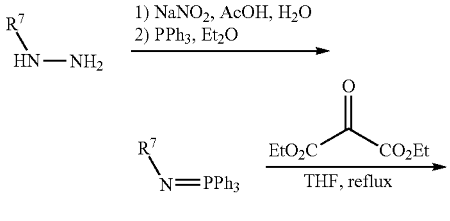

-continued

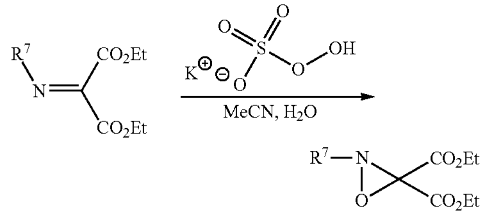

To a solution of the amino benzyl ester (HCl salt, 1.0 equiv.) in a biphasic mixture of THF and sat. aq. $NaHCO_3$ (1:1), 2-(tert-butyl)-3,3-diethyl-1,2-oxaziridine-2,3,3-tricarboxylate (1.1 equiv.) was added and the reaction mixture was allowed to stir at rt for 4 h. The reaction was diluted with EtOAc, and the aqueous layer drained. The organic layer was washed with additional water, then dried over anhydrous $Na_2SO_4$, filtered, and concentrated. Purification by flash chromatography over silica gel (15-50% EtOAc/hexanes) afforded the hydrazino ester as a clear oil (75-95% yield).

A general scheme for the preparation of moc N—NHR$^7$ dipeptides from α-hydrazino ester intermediates is shown in Scheme 2.

Scheme 2

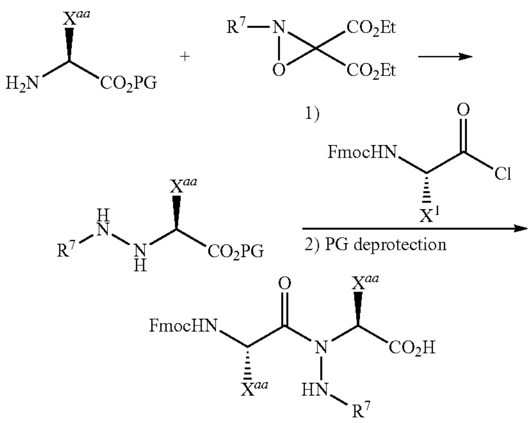

**PG may be any suitable acid labile protecting group

A solution of Fmoc amino acid (1.2 equiv.) in DCM was treated with 1-chloro-N,N,2-trimethyl-1-propenylamine (1.6 equiv.) and stirred for 10 min. The solution was then transferred into a flask containing a mixture of the hydrazino ester above (1 equiv.) and $NaHCO_3$ (3 equiv.) in DCM. The reaction was stirred for 6 h and quenched with water. The organic layer was collected, and the aq. phase extracted with additional DCM. The combined organic layers were dried over anhydrous $Na_2SO_4$, filtered, and concentrated. Purification by silica gel flash chromatography (15-75% EtOAc/hexanes) afforded the protected N-amino dipeptide as an off-white solid (73-82% yield).

To a solution of the protected N-amino dipeptide above (1.0 equiv.) in EtOAc was added 10% Pd/C (150 mg/mmol) and the mixture stirred under $H_2$ atmosphere at rt for 6 h. The reaction was diluted with additional EtOAc, filtered through Celite, and concentrated. Purification by flash chromatography (25-100% EtOAc/hexanes) afforded the aminated carboxylic acid as a white solid (68-94%).

Exemplary schemes are shown in Schemes 3 and 4.

Scheme 3

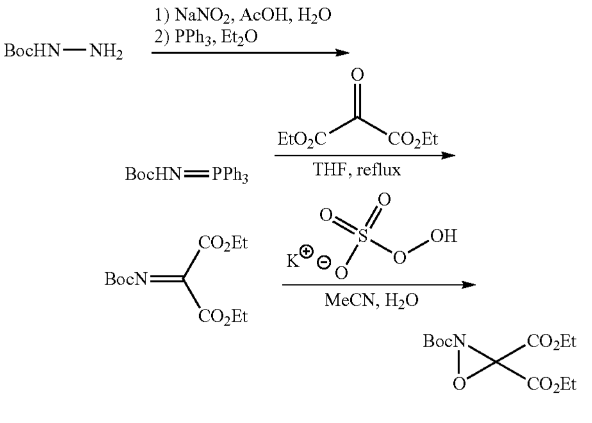

Scheme 4

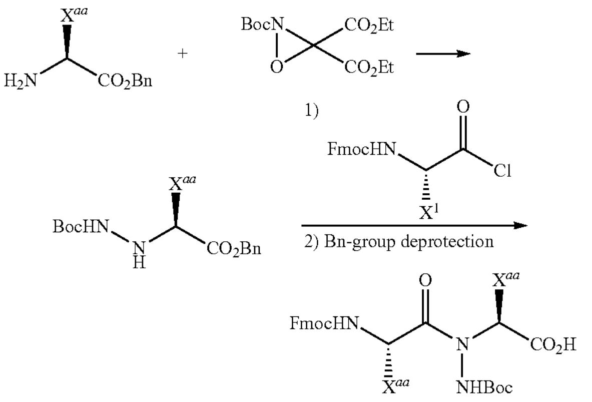

Fmoc-Ile-(N'-Boc)aVal-OH

Obtained as a white solid (54% yield over 3 steps); $^1$H NMR (500 MHz, $CDCl_3$, mixture of rotamers) δ 8.60 (s, 1H), 8.19 (s, 1H), 7.76 (d, J=7.5 Hz, 2H), 7.66-7.49 (m, 2H), 7.44-7.37 (m, 2H), 7.33-7.29 (m, 2H), 5.62-5.42 (m, 0.8H), 5.16 (m, 0.2H), 4.78-4.61 (m, 0.4H), 4.55-4.14 (m, 4.6H), 2.50-2.27 (m, 0.4H), 2.09-1.86 (m, 1.6H), 1.71-1.60 (m, 1H), 1.58-1.47 (m, 9H), 1.23-0.84 (m, 13H); $^{13}$C NMR (126 MHz, $CDCl_3$, mixture of rotamers) δ 175.8, 175.7, 172.6, 171.5, 158.3, 157.5, 156.1, 155.7, 144.0, 143.6, 143.5, 141.3, 127.9, 127.8, 127.7, 127.1, 125.3, 125.2, 125.1, 125.0, 120.1, 120.0, 120.0, 84.7, 84.6, 77.4, 67.8, 67.6, 67.0, 64.1, 55.9, 54.8, 47.3, 46.9, 38.5, 38.0, 35.2, 28.3, 28.2, 27.9, 26.8, 24.6, 23.9, 23.6, 21.1, 20.1, 19.2, 19.1, 16.1, 15.8, 11.7, 10.5; HRMS (ESI-TOF) m/z $[M+H]^+$ calculated for $C_{31}H_{42}N_3O_7$ 569.3096, found 569.3121.

Fmoc-Ile-(N'-Boc)aIle-OH

Obtained as a white solid (47% yield over 3 steps); $^1$H NMR (500 MHz, $CDCl_3$, mixture of rotamers) δ 8.52 (s, 0.67H), 8.07 (s, 0.13H), 7.76 (d, J=7.5 Hz, 2H), 7.65-7.50 (m, 2H), 7.45-7.37 (m, 2H), 7.35-7.28 (m, 2H), 5.57-5.43 (m, 0.9H), 5.24 (s, 0.1H), 4.83-4.64 (m, 0.25H), 4.60 (d, J=8.0 Hz, 0.75H), 4.49-4.27 (m, 3H), 4.26-4.10 (m, 2H), 2.07 (bs, 0.25H), 1.99-1.86 (m, 0.75H), 1.79-1.61 (m, 2H), 1.58-1.37 (m, 10H), 1.28-1.15 (m, 2H), 1.09-0.84 (m, 13H); $^{13}$C NMR (126 MHz, $CDCl_3$, mixture of rotamers) δ 175.6, 175.2, 173.9, 172.8, 171.3, 158.2, 157.4, 156.0, 155.5, 154.2, 143.8, 143.4, 143.3, 141.2, 127.8, 127.6, 127.6, 127.5, 127.1, 127.0, 125.2, 125.1, 125.0, 124.9, 124.9, 120.0, 119.9, 119.9, 119.8, 84.5, 82.5, 67.7, 66.9, 66.1, 62.9, 62.6, 55.8, 55.3, 54.6, 47.1, 46.8, 38.5, 37.9, 35.2, 35.1, 35.0, 33.0, 28.0, 27.7, 27.2, 26.8, 26.4, 24.5, 23.7, 23.5, 15.9, 15.6, 15.4, 12.1, 11.7, 11.5, 11.2, 10.3; HRMS (ESI-TOF) m/z $[M+H]^+$ calculated for $C_{32}H_{44}N_3O_7$ 583.3252, found 583.3255.

Fmoc-Gln(Trt)-(N'-Boc)aIle-OH

Obtained as a white solid (42% yield over 3 steps); $^1$H NMR (500 MHz, $CDCl_3$, mixture of rotamers) δ 8.27 (bs, 0.2H), 8.00 (bs, 0.4H), 7.80-7.70 (m, 2H), 7.65-7.52 (m, 2H), 7.39 (q, J=7.5 Hz, 2H), 7.34-7.10 (m, 17H), 6.91 (bs, 0.5H), 6.73 (bs, 0.3H), 5.99-5.87 (m, 0.25H), 5.77 (d, J=8.0 Hz, 0.6H), 4.93-4.86 (m, 0.2H), 4.80-4.51 (m, 2H), 4.45-4.30 (m, 2H), 4.27-4.17 (m, 1H), 2.49-2.03 (m, 3H), 1.99-1.58 (m, 3H), 1.51-1.09 (m, 10H), 1.01-0.80 (m, 6H); $^{13}$C NMR (126 MHz, $CDCl_3$, mixture of rotamers) δ 175.2, 174.5, 172.5, 172.0, 171.8, 156.1, 156.0, 154.9, 154.4, 144.2, 144.1, 143.7, 141.3, 141.2, 128.6, 127.9, 127.6, 127.0, 125.2, 125.1, 119.9, 83.3, 82.1, 77.2, 70.9, 66.8, 63.0, 51.1, 47.2, 34.5, 34.4, 33.2, 28.9, 28.6, 28.1, 27.8, 26.6, 15.8, 15.6, 11.8, 11.6; HRMS (ESI-TOF) m/z $[M+H]^+$ calculated for $C_{50}H_{55}N_4O_8$ 840.4093, found 840.4117.

Fmoc-Val-(N'-Boc)aTyr(tBu)-OH

Obtained as a white solid (45% yield over 3 steps); $^1$H NMR (500 MHz, $CDCl_3$, mixture of rotamers) δ 7.76-7.65 (m, 3H), 7.53-7.46 (m, 2H), 7.38-7.22 (m, 5H), 7.06-7.00 (m, 0.5H), 6.91 (m, 1.5H), 6.72 (d, J=8.0 Hz, 1H), 6.04 (bs, 0.3H), 5.35-5.11 (m, 1.5H), 4.41-4.05 (m, 4H), 3.99-3.89 (m, 1H), 3.34-3.19 (m, 1.5H), 2.81 (t, J=13.8 Hz, 0.5H), 2.04-1.91 (m, 0.5H), 1.70 (s, 0.5H), 1.51-1.34 (m, 9H), 1.31-1.19 (m, 4H), 1.11 (s, 6H), 0.93-0.79 (m, 6H); $^{13}$C NMR (126 MHz, $CDCl_3$, mixture of rotamers) δ 175.5, 174.9, 172.7, 171.6, 157.9, 156.8, 155.9, 155.7, 154.1, 153.8, 143.8, 143.6, 143.4, 141.1, 131.8, 130.6, 130.5, 129.3, 128.5, 127.6, 126.9, 125.1, 124.3, 124.1, 119.8, 84.4, 84.2, 78.3, 67.3, 66.9, 62.4, 58.7, 55.9, 55.7, 47.0, 46.9, 46.8, 33.5, 32.6, 31.0, 29.5, 29.4, 28.6, 28.0, 27.4, 19.5, 18.0, 16.5; HRMS (ESI-TOF) m/z $[M+H]^+$ calculated for $C_{38}H_{48}N_3O_8$ 675.3514, found 675.3531.

Fmoc-Tyr(tBu)-(N'-Boc)aLys(Boc)-OH

Obtained as a white solid (53% yield over 3 steps); $^1$H NMR (500 MHz, $CDCl_3$, mixture of rotamers) δ 8.63 (bs, 0.3H), 7.77 (d, J=7.5 Hz, 2H), 7.63-7.50 (m, 2H), 7.41 (t, J=7.5 Hz, 2H), 7.32 (t, J=7.4 Hz, 2H), 7.14-6.76 (m, 5H), 5.69-5.42 (m, 0.9H), 5.25 (m, 0.1H), 4.98-4.54 (m, 3H), 4.41-4.14 (m, 3H), 3.23-2.80 (m, 2H), 1.98 (bs, 0.6H), 1.81-1.65 (m, 1.3H), 1.56-1.24 (m, 35H); $^{13}$C NMR (126 MHz, $CDCl_3$, mixture of rotamers) δ 174.5, 173.4, 173.0, 171.9, 156.2, 155.2, 154.0, 143.8, 143.5, 141.1, 130.9, 129.9, 127.5, 126.9, 125.1, 124.1, 124.0, 119.8, 84.3, 84.0, 82.8, 80.7, 79.1, 78.4, 78.3, 77.2, 67.4, 66.8, 62.3, 59.6, 59.0, 58.4, 52.6, 52.0, 47.0, 46.8, 41.2, 40.2, 39.7, 38.5, 37.6, 36.6, 33.9, 31.8, 29.6, 29.3, 28.7, 28.3, 28.0, 27.8, 23.7, 23.4; HRMS (ESI-TOF) m/z $[M+H]^+$ calculated for $C_{44}H_{59}N_4O_{10}$ 804.4304, found 804.4329.

Solid-Phase Synthesis of NAPs

Solid-phase peptide synthesis was carried out using CEM-Liberty Blue peptide synthesizer on Fmoc-capped polystyrene rink amide MBHA resin (100-200 mesh, 0.05-0.15 mmol scale). The following amino acid derivatives suitable for Fmoc SPPS were used: Fmoc-Gln(Trt)-OH, Fmoc-Asn (Trt)-OH, Fmoc-Tyr(tBu)-OH, Fmoc-Lys(Boc)-OH, Fmoc-Val-OH, Fmoc-Ile-OH. Dry resin was washed with DMF 3× and allowed to swell in DMF for 5 min at elevated temperature prior to use. All reactions were carried out using gentle agitation. Fmoc deprotection steps were carried out by treating the resin with a solution of 20% piperidine/DMF (5 min×2). Coupling of Fmoc-protected amino acids as well as Fmoc-(N'-Boc)-hydrazino dipeptide acids was conducted using 5 equiv. HCTU (0.5 M in DMF), 10 equiv. NMM (1.0 M in DMF), and 5 equiv. of the carboxylic acid in DMF at 50° C. (10 min). After each reaction the resin was washed with DMF 2×, DCM 2×. Peptides were cleaved from the resin by incubating with gentle stirring in 2 mL of 95:2.5:2.5 TFA:$H_2O$:TIPS at rt for 2 h. The cleavage mixture was filtered, and the resin was rinsed with an additional 1 mL of cleavage solution. The filtrate was treated with 8 mL of cold $Et_2O$ to induce precipitation. The mixture was centrifuged, and the supernatant was removed. The remaining solid was washed 2 more times with $Et_2O$ and dried under vacuum. Peptides were analyzed and purified on $C_{12}$ RP-HPLC columns (preparative: 4 µm, 90 Å, 250×21.2 mm; analytical: 4µ, 90 Å, 150×4.6 mm) using linear gradients of MeCN/$H_2O$ (with 0.1% formic acid), then lyophilized to afford white powders. All peptides were characterized by LCMS (ESI), HRMS (ESI-TOF), and $^1$H NMR. Analytical HPLC samples for all purified peptides were prepared as 1 mM in MeCN. Linear gradients of MeCN in $H_2O$ (0.1% formic acid) were run over 20 or 12 minutes and spectra are provided for λ=220 nm.

Ac-aVal-Gln-Ile-Ile-Asn-Lys-$NH_2$ (1; EG02)

The crude peptide was purified by preparative scale RP-HPLC using a 5-95% MeCN/$H_2O$ gradient (with 0.1% formic acid). The pure peptide was obtained in 81% yield. HRMS (ESI-TOF) m/z $[M+H]^+$ calculated for $C_{34}H_{64}N_{11}O_9$ 770.4883, found 770.4877.

Ac-Val-Gln-aIle-Ile-Asn-Lys-$NH_2$ (2; EG01)

The crude peptide was purified by preparative scale RP-HPLC using a 5-95% MeCN/$H_2O$ gradient (with 0.1% formic acid). The pure peptide was obtained in 45% yield. HRMS (ESI-TOF) m/z $[M+H]^+$ calculated for $C_{34}H_{64}N_{11}O_9$ 770.4883, found 770.4878.

Ac-Val-Gln-Ile-aIle-Asn-Lys-$NH_2$ (3; EF09)

The crude peptide was purified by preparative scale RP-HPLC using a 5-95% MeCN/$H_2O$ gradient (with 0.1% formic acid). The pure peptide was obtained in 75% yield. HRMS (ESI-TOF) m/z $[M+H]^+$ calculated for $C_{34}H_{65}N_{12}O_9$ 770.4883, found 770.4879.

Ac-aVal-Gln-aIle-Ile-Asn-Lys-$NH_2$ (4; EG05)

The crude peptide was purified by preparative scale RP-HPLC using a 5-95% MeCN/$H_2O$ gradient (with 0.1% formic acid). The pure peptide was obtained in 81% yield. HRMS (ESI-TOF) m/z $[M+H]^+$ calculated for $C_{38}H_{65}N_{10}O_9$ 785.4992, found 785.4992.

Ac-aVal-Gln-Ile-Val-Tyr-Lys-$NH_2$ (5; EF05)

The crude peptide was purified by preparative scale RP-HPLC using a 5-95% MeCN/$H_2O$ gradient (with 0.1% formic acid). The pure peptide was obtained in 88% yield. HRMS (ESI-TOF) m/z $[M+H]^+$ calculated for $C_{38}H_{65}N_{10}O_9$ 805.4931, found 805.4930.

Ac-Val-Gln-aIle-Val-Tyr-Lys-$NH_2$ (6; EF04)

The crude peptide was purified by preparative scale RP-HPLC using a 5-95% MeCN/$H_2O$ gradient (with 0.1% formic acid). The pure peptide was obtained in 55% yield. HRMS (ESI-TOF) m/z $[M+H]^+$ calculated for $C_{38}H_{65}N_{10}O_9$ 805.4931, found 805.4925.

Ac-Val-Gln-Ile-aVal-Tyr-Lys-$NH_2$ (7; EE04)

The crude peptide was purified by preparative scale RP-HPLC using a 5-95% MeCN/$H_2O$ gradient (with 0.1% formic acid). The pure peptide was obtained in 88% yield. HRMS (ESI-TOF) m/z $[M+H]^+$ calculated for $C_{38}H_{65}N_{10}O_9$ 805.4931, found 805.4927.

Ac-Val-Gln-Ile-Val-aTyr-Lys-$NH_2$ (8; EE03)

The crude peptide was purified by preparative scale RP-HPLC using a 5-95% MeCN/$H_2O$ gradient (with 0.1% formic acid). The pure peptide was obtained in 38% yield. HRMS (ESI-TOF) m/z $[M+H]^+$ calculated for $C_{38}H_{65}N_{10}O_9$ 805.4931, found 805.4927.

Ac-Val-Gln-Ile-Val-Tyr-aLys-$NH_2$ (9; EE06)

The crude peptide was purified by preparative scale RP-HPLC using a 5-95% MeCN/$H_2O$ gradient (with 0.1% formic acid). The pure peptide was obtained in 99% yield. HRMS (ESI-TOF) m/z $[M+H]^+$ calculated for $C_{38}H_{65}N_{10}O_9$ 805.4931, found 805.4933.

Ac-aVal-Gln-aIle-Val-Tyr-Lys-$NH_2$ (10; EG07)

The crude peptide was purified by preparative scale RP-HPLC using a 5-95% MeCN/$H_2O$ gradient (with 0.1% formic acid). The pure peptide was obtained in 52% yield. HRMS (ESI-TOF) m/z $[M+H]^+$ calculated for $C_{38}H_{66}N_{11}O_9$ 820.5040, found 820.5045.

Ac-aVal-Gln-Ile-Val-aTyr-Lys-$NH_2$ (11; EG06)

The crude peptide was purified by preparative scale RP-HPLC using a 5-95% MeCN/$H_2O$ gradient (with 0.1% formic acid). The pure peptide was obtained in 58% yield. HRMS (ESI-TOF) m/z $[M+H]^+$ calculated for $C_{38}H_{66}N_{11}O_9$ 820.5040, found 820.5041.

Ac-Val-Gln-aIle-Val-aTyr-Lys-$NH_2$ (12; EG09)

The crude peptide was purified by preparative scale RP-HPLC using a 5-95% MeCN/$H_2O$ gradient (with 0.1% formic acid). The pure peptide was obtained in 44% yield. HRMS (ESI-TOF) m/z $[M+H]^+$ calculated for $C_{38}H_{66}N_{11}O_9$ 820.5040, found 820.5048.

Ac-Val-Gln-Ile-aVal-Tyr-aLys-$NH_2$ (13; EG08)

The crude peptide was purified by preparative scale RP-HPLC using a 5-95% MeCN/$H_2O$ gradient (with 0.1% formic acid). The pure peptide was obtained in 42% yield. HRMS (ESI-TOF) m/z $[M+H]^+$ calculated for $C_{38}H_{66}N_{11}O_9$ 820.5040, found 820.5039.

Ac-aVal-Gln-aIle-Val-aTyr-Lys-NH2 (14; EH02)

The crude peptide was purified by preparative scale RP-HPLC using a 5-95% MeCN/$H_2O$ gradient (with 0.1% formic acid). The pure peptide was obtained in 28% yield. HRMS (ESI-TOF) m/z $[M+H]^+$ calculated for $C_{38}H_{67}N_{12}O_9$ 835.5149, found 835.5115.

Ac-Val-Gln-Ile-Val-Tyr-Lys-$NH_2$ (Ac-PHF6; EE02)

The crude peptide was purified by preparative scale RP-HPLC using a 5-95% MeCN/$H_2O$ gradient (with 0.1% formic acid). The pure peptide was obtained in 92% yield. HRMS (ESI-TOF) m/z $[M+H]^+$ calculated for $C_{38}H_{63}N_9O_9$ 790.4822, found 790.4833.

Ac-Val-Gln-Ile-Ile-Asn-Lys-$NH_2$ (Ac-PHF6* EF06)

The crude peptide was purified by preparative scale RP-HPLC using a 5-95% MeCN/$H_2O$ gradient (with 0.1% formic acid). The pure peptide was obtained in 50% yield. HRMS (ESI-TOF) m/z $[M+H]^+$ calculated for $C_{34}H_{63}N_{10}O_9$ 755.4774, found 755.4775.

Example 2

2D NOE Spectroscopy for Compounds 12 (EG09) and 13 (EG08)

NMR Acquisition Parameters

Purified peptides were dissolved in $CDCl_3$ or DMSO-$d_6$. Final peptide concentration was 1 mM, determined by mass. Data were collected at 25° C. on a 500 MHz Bruker ASCEND 11.74 T, narrow bore 54 mm, BOSS-3 36 shim system, BSMS shim and digital lock control units with a 5 mm direct detect SMART probe ($^1H/^{13}C/^{15}N$ with Z-axis PFG), or an 800 MHz AVANCE II with UltraStabilized and UltraShield 18.79 T, 54 mm bore, BOSS-2 34 shim system and a 5 mm broadband (BBO) $^{15}N$-$^{31}P$, 1H decoupling, Z-axis PFG. The TOCSY used a mixing time of 80 ms, and the ROESY had a mixing time of 200 ms. In the $F_2$ direction, the TOCSY and ROESY had 2048 complex points collected, and in the $F_1$ direction, 512 complex points were collected. Watergate 3-9-19 was used for solvent suppression where appropriate. Bruker TopSpin 4.0 or Mestrenova 10.0 software was used to process the data, and Gaussian functions were used before Fourier transformation.

Ac-Val-Gln-aIle-Val-aTyr-Lys-$NH_2$ (12, EG09) in DMSO-de

The following is a list of inter-residue correlations: Val1 NH—Ac $CH_3$ (s); Gln2 NH-Val1 α (s); Gln2 NH-Val1 β (s); Gln2 NH-Val1 γ (m); aIle3 $NH_2$-Gln2 α (s); aIle3 $NH_2$-Gln2 β (w); Val4 $NH_2$-aIle3 α (s); Val4 $NH_2$-aIle3 γ (m); aTyr5 NH2-Val4 α (s); Tyr5 NH2-Val4 β (s); aTyr5 ε-aIle3 β $CH_3$ (w); aTyr5 δ-aIle3 γ $CH_3$ (m); aTyr5 ε-aIle3 γ $CH_3$ (s); Lys6 NH-aTyr5 α (s); Lys6 NH-aTyr5 β (s); C-term $NH_2$-Lys6 NH (w) C-term $NH_2$-Lys6 α (s); and C-term $NH_2$-Lys6 β (m) C-term $NH_2$-Lys6 δ (w).

Ac-Val-Gln-aIle-Val-aTyr-Lys-$NH_2$ (12, EG09) in $D_2O$

The following is a list of inter-residue correlations: Val1 NH—Ac $CH_3$ (s); Gln2 NH-Val1 α (s); Gln2 NH-Val1 γ (m); aIle3 $NH_2$-Gln2 β (m); Val4 $NH_2$-aIle3 α (s); Val4 $NH_2$-aIle3 γ (w); Val4 $NH_2$-aIle3 δ (m); aTyr5 $NH_2$-Val4 β (s); aTyr5 δ-aIle3 δ (w); aTyr5 ε-aIle3 δ (m); Lys6 NH-aTyr5 α (s); Lys6 NH-aTyr5 β (m); C-term $NH_2$-Lys6 α (s); and C-term $NH_2$-Lys6 β (w).

Ac-Val-Gln-Ile-aVal-Tyr-aLys-$NH_2$ (13, EG08) in DMSO-$d_6$.

The following is a list of inter-residue correlations: Val1 NH—Ac $CH_3$ (s); Gln2 NH-Val1 α (s); Gln2 NH-Val1 β (m); Gln2 NH-Val1 γ (w); Ile3 NH-Gln 2 α (s); aVal4 $NH_2$-Ile3 α (s); aVal4 $NH_2$-Ile3 β (w); aVal4 $NH_2$-Ile3 γ (w); Tyr5 NH-aVal4 α (s); Tyr5 NH-aVal4 β (m); Tyr5 NH-aVal4 γ (m); Tyr5 δ-Ile3 γ (w); Tyr5 ε-Ile3 γ (w); Tyr5 ε-Ile3 δ (w); Tyr5 ε-aLys6 β (w); aLys6 $NH_2$-Tyr5 α (s); aLys6 NH2-Tyr5 β (m); aLys6 $NH_2$-Tyr5 δ (w); C-term $NH_2$-aLys6 α (s); and C-term $NH_2$-aLys6 β (w).

Ac-Val-Gln-Ile-aVal-Tyr-aLys-$NH_2$ (13, EG08) in $D_2O$

The following is a list of inter-residue correlations: Val1 NH—Ac $CH_3$ (s); Gln2 NH-Val1 α (s); Ile3 NH-Gln2 α (s); Ile3 NH-Gln2 β (m); Ile3 NH-Gln2 γ (w); aVal4 $NH_2$-Ile3 α (s); aVal4 $NH_2$-Ile3 β (m); aVal4 $NH_2$-Ile3 γ (w); aVal4 NH2-Ile3 δ (w); Tyr5 NH-aVal4 α (s); Tyr5 NH-aVal4 γ (m); Tyr5 δ-Ile3 γ $CH_3$ (w); Tyr5 ε-Ile3 γ $CH_3$ (w); Tyr5 δ-Ile3 δ (m); Tyr5 ε-Ile3 δ (m); aLys6 $NH_2$-Tyr5 α (s); aLys6 $NH_2$-Tyr5 β (m); and aLys6 $NH_2$-Tyr5 δ (w).

TABLE 2

$^1H$ NMR data for Compounds12 (EG09) and 13 (EG08) (δ values in ppm)

| | NH | α | β | Others |
|---|---|---|---|---|
| Ac-Val-Gln-alle-Val-aTyr-Lys-$NH_2$ (Cmpd 12, EG09) in DMSO-$d_6$ | | | | |
| Val | 7.85 | 4.20 | 1.94 | γ $CH_3$ 0.79, 0.81; Ac $CH_3$ 1.85 |
| Gln | 7.88 | 5.12 | 1.81, 1.60 | γ $CH_2$ 2.00, 2.07; δ $NH_2$ 7.47, 6.48 |
| alle | — | 4.67 | 1.98 | $NH_2$ 4.61; γ CH2 0.91; γ $CH_3$ 1.24; δ $CH_3$ 0.68 |
| Val | 7.68 | 5.12 | 1.95 | γ $CH_2$ 0.73 |
| aTyr | — | 5.24 | 3.01 | $NH_2$ 4.51; δ $CH_2$ 7.03; ε $CH_2$ 6.60 |
| Lys | 8.19 | 4.14 | 1.63 | γ $CH_2$ 1.25; δ $CH_2$ 1.47; ε $CH_2$ 2.68; C-term $NH_2$ 7.28, 7.02 |
| Ac-Val-Gln-alle-Val-aTyr-Lys-$NH_2$ (Cmpd 12, EG09) in $D_2O$ | | | | |
| Val | 8.13 | 4.09 | 2.04 | γ $CH_3$ 0.93; Ac $CH_3$ 2.05 |
| Gln | 8.40 | 5.37 | 2.05, 1.86 | γ $CH_2$ 2.31, 2.35; δ $NH_2$ 7.54, 6.89 |
| alle | — | 4.59 | 2.07 | $NH_2$ 4.66; γ $CH_2$ 0.85, 1.02; γ $CH_3$ 1.35; δ $CH_3$ 0.69 |
| Val | 8.23 | 5.16 | 5.16 | γ $CH_2$ 0.84 |
| aTyr | — | 5.32 | 5.32 | $NH_2$ 4.65; δ $CH_2$ 7.19; ε $CH_2$ 6.83 |
| Lys | 8.44 | 4.24 | 4.24 | γ $CH_2$ 1.39; δ $CH_2$ 1.68; ε $CH_2$ 2.98; C-term $NH_2$ 7.32, 7.12 |
| Ac-Val-Gln-Ile-aVal-Tyr-aLys-$NH_2$ (Cmpd 13, EG08) in DMSO-$d_6$ | | | | |
| Val | 8.16 | 4.07 | 2.05 | γ $CH_3$ 0.95; Ac $CH_3$ 2.06 |
| Gln | 8.47 | 4.38 | 2.02, 1.92 | γ $CH_2$ 2.34; δ NH2 7.23, 6.74; δ $NH_2$ 7.54, 6.88 |
| Ile | 8.21 | 5.26 | 1.71 | γ $CH_2$ 1.14, 1.44; γ $CH_3$ 0.83; δ $CH_3$ 0.53 |
| aVal | N/A | 4.62 | 2.24 | $NH_2$ 4.49; γ $CH_2$ 0.82, 0.94 |
| Tyr | 8.63 | 5.53 | 3.12, 2.79 | δ $CH_2$ 7.20; ε $CH_2$ 6.82 |
| aLys | N/A | 4.98 | 1.93 | $NH_2$ 4.56; γ $CH_2$ 1.36, 1.30; δ $CH_2$ 1.71; ε $CH_2$ 2.99; C-term $NH_2$ 7.14, 6.85 |
| Ac-Val-Gln-Ile-aVal-Tyr-aLys-$NH_2$ (Cmpd 13, EG08) in $D_2O$ | | | | |
| Val | 7.92 | 4.16 | 1.95 | γ $CH_3$ 0.82, 0.84; Ac $CH_3$ 1.86 |
| Gln | 8.09 | 4.24 | 1.82, 1.67 | γ $CH_2$ 2.06; δ $NH_2$ 7.23, 6.74 |
| Ile | 7.56 | 5.28 | 1.69 | γ $CH_2$ 1.37, 1.00; γ $CH_3$ 0.63; δ $CH_3$ 0.75 |
| aVal | N/A | 4.65 | 2.17 | $NH_2$ 4.57; γ $CH_2$ 0.70, 0.89 |
| Tyr | 8.20 | 5.27 | 2.91, 2.67 | δ $CH_2$ 6.59; ε $CH_2$ 7.01 |
| aLys | N/A | 4.89 | 1.71, 1.84 | $NH_2$ 4.65; γ $CH_2$ 1.27, 1.13; δ $CH_2$ 1.51; ε $CH_2$ 2.70; C-term $NH_2$ 7.47, 7.17 |

Example 3

$TAU_{P301L}$ Expression and Purification

Figure 4:
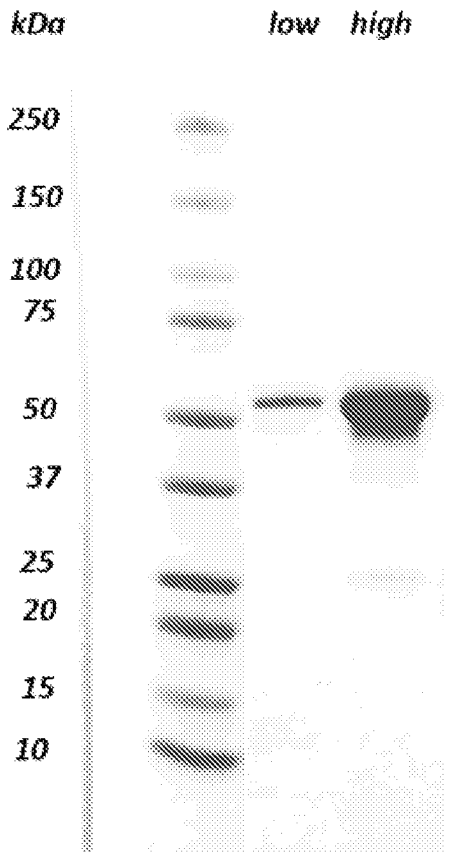
FIG. 4 shows a Coomassie blue-stained SDS/PAGE of purified recombinant $tau_{P301L}$ protein loaded at low and high concentration.

Human $tau_{P301L}$ (0N4R) (SEQ ID NO: 3-4) was cloned into pET28b with an N-terminal $His_6$ tag. Briefly, transformed BL21(DE3) cells were grown in LB+kanamycin media at 37° C. until $OD_{600}$ reached 0.8 and was then induced with 1 mM IPTG overnight at 16° C. Cells were then harvested, resuspended, and lysed by probe sonication in the lysis buffer containing 20 mM Tris, 500 mM NaCl, 10 mM imidazole, Roche cOmplete™ protease inhibitor cocktail, adjusted to pH 8.0. The lysate was then boiled for 20 minutes in a water bath and the debris was pelleted by centrifugation at 20,000×g for about 40 minutes 4° C. The supernatant obtained was then injected onto a 5 mL IMAC Ni-charged affinity column (Profinity™) and eluted over a gradient of 10-200 mM imidazole. Eluted tau-containing fractions were further purified and using GE HiPrep™ 16/60 Sephacryl™ S-200 high-resolution size exclusion chromatography into a storage buffer containing 20 mM Tris·HCl, 150 mM NaCl, and 1 mM DTT, adjusted to pH 7.6. The purity of the protein was confirmed was SDS-PAGE analysis (FIG. 4) and the concentration was estimated using BCA assay.

Thioflavin T (ThT) Fluorescence Aggregation Assay

Recombinant $tau_{P301L}$ (10 μM final concentration) and NAP inhibitors 20 μM final concentration) were mixed in an aggregation buffer (100 mM sodium acetate, 10 μM ThT, 10 μM heparin, 2 mM DTT, 0.5% DMSO, pH 7.4) in a 96-well clear bottom black plate with a final reaction volume of 200 μL. The plate was then sealed with a clear sealing film and allowed to incubate at 37° C. with continuous shaking in a Biotek Synergy H1 microplate reader. An automated method was used to carry out ThT fluorescence measurements at an excitation wavelength of 444 nm and an emission wavelength of 485 nm at an interval of every 5 minutes for 48 hours. Experiments were carried out in technical replicates on at least two different days. Every experiment included control wells that lacked $tau_{301L}$, heparin, or NAPs. The average of tau-only (no heparin) wells was used to subtract background fluorescence and the average of the first and last 10 data points of tau+heparin wells, after blank subtraction, was used to normalize the data. All data plots were generated with SigmaPlot.

Transmission Electron Microscopy

For analyzing fibrils by transmission electron microscopy (TEM), aggregation was carried out under conditions similar to the assay above but with ThT excluded and a final reaction volume of 100 μL Samples were incubated in a microcentrifuge tube for 4 days at 37° C. with a mixing speed of 100 rpm. A 10 μL aliquot of the sample was then applied to 400-meshed formvar/carbon-coated copper grids and negative stained with 2% uranyl-acetate. Micrographs were taken on a JEOL 2011 TEM at 200 kV.

Cellular Seeding Assays

Tau Fibril Formation $Tau_{P301L}$ was diluted to a final concentration of 10 μM in an aggregation buffer containing 100 mM sodium acetate, 10 μM heparin, 2 mM DTT, pH 7.4. The protein was incubated in a microcentrifuge tube for 4 days at 37° C. with a shaking speed of 100 rpm. Control vials included those wherein (1) buffer was added in place of $tau_{P301L}$, and (2) buffer was added in place of heparin.

Tau Seeding Assay

HEK293 cells stably expressing tau-RD (LM)-YFP were cultured in DMEM media containing 10% FBS, 1% penicillin/streptomycin, and 1% Glutamax™ (Gibco) in a 75 $cm^2$ cell culture flask under 5% $CO_2$ at 37° C. For each experiment, cells were plated at a density of 15000 cells/well into 96 well tissue culture plates.

Seeding by Monomeric Tau

Monomeric $tau_{P301L}$ was co-incubated with NAPs for 4 days in an aggregation buffer at 37° C. (see above section). Following incubation, the reaction mixture was diluted in low serum Opti-MEM® media (Gibco), mixed with lipofectamine 2000 in 20:1 ratio (complex:lipofectamine) and allowed to incubate for an additional 20 minutes at RT. A mixture of 0.19 μM of Tau+1.9 μM or 0.009 μM of inhibitors (final concentrations) was added to the cells. Cells were incubated for additional 48 h before taking measurements on a BioTek Cytation 5 cell imager and microplate reader. 10×10 pictures/well were taken at 20× magnification under FITC channel and the punctate counting was carried out using built-in software. Each data set was collected from technical replicates on at least two different days. Every experiment included control wells (no tau, no heparin, and no NAP). All data plots were generated with SigmaPlot. Error bars shown are standard deviation from technical replicates.

Seeding by Fibrillar Tau $Tau_{P301L}$ fibrils were prepared as described above (see section on fibril formation) and sonicated for 3 minutes prior to use in this assay. In a reaction volume of 40 μL, 8 μL of fibrils was diluted with 31 μL of low-serum Opti-MEM® (Gibco) media and then mixed with 1 μL of NAPs (DMSO concentration was constant across various concentration of inhibitors). The reaction mixture was then allowed to incubate at 37° C. for 36 h, then mixed with 2 μL of lipofectamine 2000 and further incubated for 20 minutes at R.T. A 10 μL aliquot of this mixture was then added into 90 μL of cells (15000 cells/well). Cells were incubated for additional 48 h before taking measurements on BioTek Cytation 5 cell imager and microplate reader. 10×10 pictures/well were taken at 20× magnification under FITC channel and the punctate counting were carried out using built-in software. Each data set were collected from technical replicates on at least two different days. Every experiment had Tau control well (no Tau but rest all), heparin control well (no heparin but rest all), and Tau alone well (no inhibitors but rest all). Every experiment included control wells (no tau, no heparin, and no NAP). All data plots were generated with Sigma plot. $IC_{50}$ values were calculated by fitting the data set using sigmoidal logistic 4 parameter equation. Error bars represent standard deviation from technical replicates. % Tau infection was calculated using following formula:

$$\%\text{ Tau infection} = 100 \times \frac{(\text{No. of punctates in sample well} - \text{No. of punctates in blank well})}{(\text{No. of punctates in Tau alone} - \text{No. of punctates in blank well})}$$

Human Serum Stability Assay

The stability of NAPs in 25% human serum (Millipore Sigma) was assessed by HPLC. The reaction was started by adding NAPs at a final concentration of 500 μM in prewarmed serum. The mixture was incubated at 37° C. for 24 h. A 100 μL aliquot of the reaction mixture was taken out at 0 h, 1 h, 4 h, and 24 h and was mixed with an equal volume of 20% TCA and incubated at 4° C. for 15 minutes to precipitate serum proteins. After centrifugation at 12000 rpm for 10 min, the supernatant was collected and mixed with an internal standard (1 mg/mL of Cbz-Tyr-OH dissolved in MeCN) and stored at −20° C. Samples were then analyzed by LC-MS and the percentage of peptide remaining was calculated by integrating peaks.

MTT Cell Viability Assays

MTT cell viability assays were carried out on both HEK293 cells stably expressing tau-RD (LM)-YFP and SH-SY5Y cells. Cells were cultured in DMEM/F12 complete media containing 10% FBS, 1% penicillin/streptomycin and 1% Glutamax™ (Gibco) in a 75 $cm^2$ cell culture flask under 5% $CO_2$ at 37° C. Cell viability was determined using MTT reduction assay. Briefly, 15,000 cells/well were plated in a 96 well tissue culture plate and were allowed to incubate overnight in a $CO_2$ incubator. The media was aspirated, and the NAP inhibitor prepared in complete media was added at a given final concentration. The plate was then allowed to incubate for additional 48 h in a $CO_2$ incubator and the media was aspirated again and replaced with 0.5 mg/mL of MTT prepared in complete media and incubated for additional 3 h. Media was then replaced with DMSO to dissolve formazan crystals and the absorbance was measured at 570 nm using Synergy H1 micro plate reader. Each data set were collected from technical replicates on at least two different days.

Example 4

Molecular Dynamics Simulations

Simulated Annealing with NOE Distance Restraints

The simulated annealing protocol includes the following steps: (1) Structures of 12 (EG09; SEQ ID NO: 18) and 13 (EG08; SEQ ID NO: 19) were prepared using Maestro. (2) Each initial structure was first energy minimized in vacuum. (3) Next, beginning with the minimized structure, 100 replicas were generated with different initial velocities and each replica was heated from 300 K to 800 K in 100 ps and simulated at 800 K for another 100 ps. (4) After annealing, each replica was solvated. The dimensions of the box were chosen such that the distance between the walls of the box and any atom of the compound was at least 1.0 nm. Minimal counter ions were added to neutralize the net charge of the system. The entire system was then energy minimized using the steepest descent algorithm to remove any bad contacts. (5) Next, the system underwent a 500 ps NVT equilibration at 300 K. (6) Lastly, the system was annealed from 300 K to 500 K and then subsequently down to 5 K over 1 ns in an NPT ensemble (the temperature was increased from 300 K to 500 K in the first 100 ps, maintained at 500 K for 100 ps, decreased to 300 K in the following 500 ps, maintained at 300 K for 100 ps, and then decreased to 5 K in the last 200 ps). (7) After all the simulation steps, the final frames from each of the 100 trajectories were used for the analysis.

GROMACS 4.6.7 suite with the OPLS2005 force field with TIP4P water model was used for simulations. Throughout the simulated annealing protocol, NOE-derived distance restraints were applied to the compound with a force constant of 10,000 $kJ \cdot mol^{-1} \cdot nm^{-2}$. The temperature was regulated using a v-rescale thermostat, with a coupling time constant of 0.1 ps. The pressure was regulated using a Berendsen barostat, with a time coupling constant of 2.0 ps and isothermal compressibility of $4.5 \times 10^{-5}$ $bar^{-1}$. The leapfrog algorithm with an integration time step of 2 fs was used to evolve the dynamics of the system. The LINCS algorithm was used to constrain all bonds containing hydrogens to the equilibrium bond lengths. For simulations in vacuum, the cutoffs of all non-bonded (electrostatics and van der Waals) interaction were set to 999.0 nm and the neighbor list was only constructed once and never updated. For simulations in solvent, all non-bonded interactions as well as neighbor searching were truncated at 1.0 nm. Long-range electrostatics beyond the 1.0 nm were calculated using the particle mesh Ewald method with a Fourier spacing of 0.12 nm and an interpolation order of 4. To account for truncation of the Lennard-Jones interactions, a long-range analytic dispersion correction was applied to both energy and pressure.

Dihedral principal component analysis (dPCA) was performed on the backbone (ø, ψ) angles of residues V, Q, I, V, Y, K of 12 (EG09; SEQ ID NO: 18) and 13 (EG08; SEQ ID NO: 19). The first three principal components were used for further cluster analysis. The population for each cluster was calculated and the conformational entropy for each system was computed via the relation: $S=-R\Sigma_i p_i \ln p_i$, where $p_i$ is the population of cluster i, and R is the ideal gas constant. For 12 (EG09; SEQ ID NO: 18), 99 structures were grouped into 18 clusters. For 13 (EG08; SEQ ID NO: 19), 87 structures were grouped into 16 clusters.

Conventional Molecular Dynamics

Conventional molecular dynamics (MD) simulations were performed for AcPHF6 (EE02; SEQ ID NO: 22), 12 (EG09; SEQ ID NO: 18), and 13 (EG08; SEQ ID NO: 19). Initial structures were built using Maestro. The topology file for each compound was generated using the Schrödinger utility ffld_server and converted to the GROMACS format using the ffconv.py script. All MD simulations in this study were performed using the GROMACS 4.6.7 suite with the OPLS 2005 force field and the TIP4P water model. The initial structure was first energy minimized for 10,000 steps and then solvated in a cubic box of water molecules. The box size was chosen such that the distance between the compound and the box wall was at least 1.0 nm. Minimal explicit counter ions were also added to neutralize the net charge of the system. With all heavy atoms restrained, the solvated system was further energy minimized for 5,000 steps. With all the heavy atoms remained restrained to their initial coordinates, a 50-ps NVT equilibration at 300 K was performed, followed by a 50-ps NPT equilibration at 300 K and 1 bar to adjust the solvent density. Then, the position restraints on heavy atoms were removed. The system underwent a further equilibration process in the NVT ensemble for 100 ps, and in the NPT ensemble for 100 ps. The equilibrated system then underwent a 500 ns production run in the NPT ensemble at 300 K and 1 bar. In all the simulations, the temperature was regulated using the v-rescale thermostat with a coupling time constant of 0.1 ps. To avoid the "hot solvent/cold solute" artifacts, two separated thermostats were applied to the solvent (water and ions) and the compound. For the NPT simulations, the pressure was maintained using the isotropic Parrinello-Rahman barostat with a coupling time of 2.0 ps and compressibility of $4.5 \times 10^{-5}$ $bar^{-1}$. Bonds involving hydrogen were constrained using the LINCS algorithm. A 2-fs time step was used with the leapfrog integrator. The nonbonded interactions (Lennard-Jones and electrostatic) were truncated at 1.0 nm. Long-range electrostatic interactions were treated using the Particle Mesh Ewald summation method. A long-range analytic dispersion correction was applied to both the energy and pressure to account for the truncation of Lennard-Jones interactions. The last 400 ns of each production run was used for further analysis.

Example 5

Design and Synthesis of NAP-Based Tau Ligands

The $^{306}$VQIVYK$^{311}$ hexapeptide motif (SEQ ID NO: 6) is widely accepted as the key amyloidogenic core of tau because filaments formed from this motif closely resemble those observed from Alzheimer's disease (AD) tau. However, recent crystal structures of the $^{275}$VQIINK$^{280}$ motif (SEQ ID NO: 5) show tighter side chain packing and strand interdigitation relative to the R3 hexapeptide, suggesting it to be a more powerful driver of tau aggregation. Since the specific contribution of individual residues in these sequences have not yet been studied, a backbone N-amino scan was performed along the length of each hexapeptide. The NAP-based library included mono-, di-, and tri-N-aminated analogues. Poly-N-amino peptides were limited to those harboring amide substitutions on a single H-bonding edge, thus retaining a fully intact edge for interaction with tau.

Figure 3:
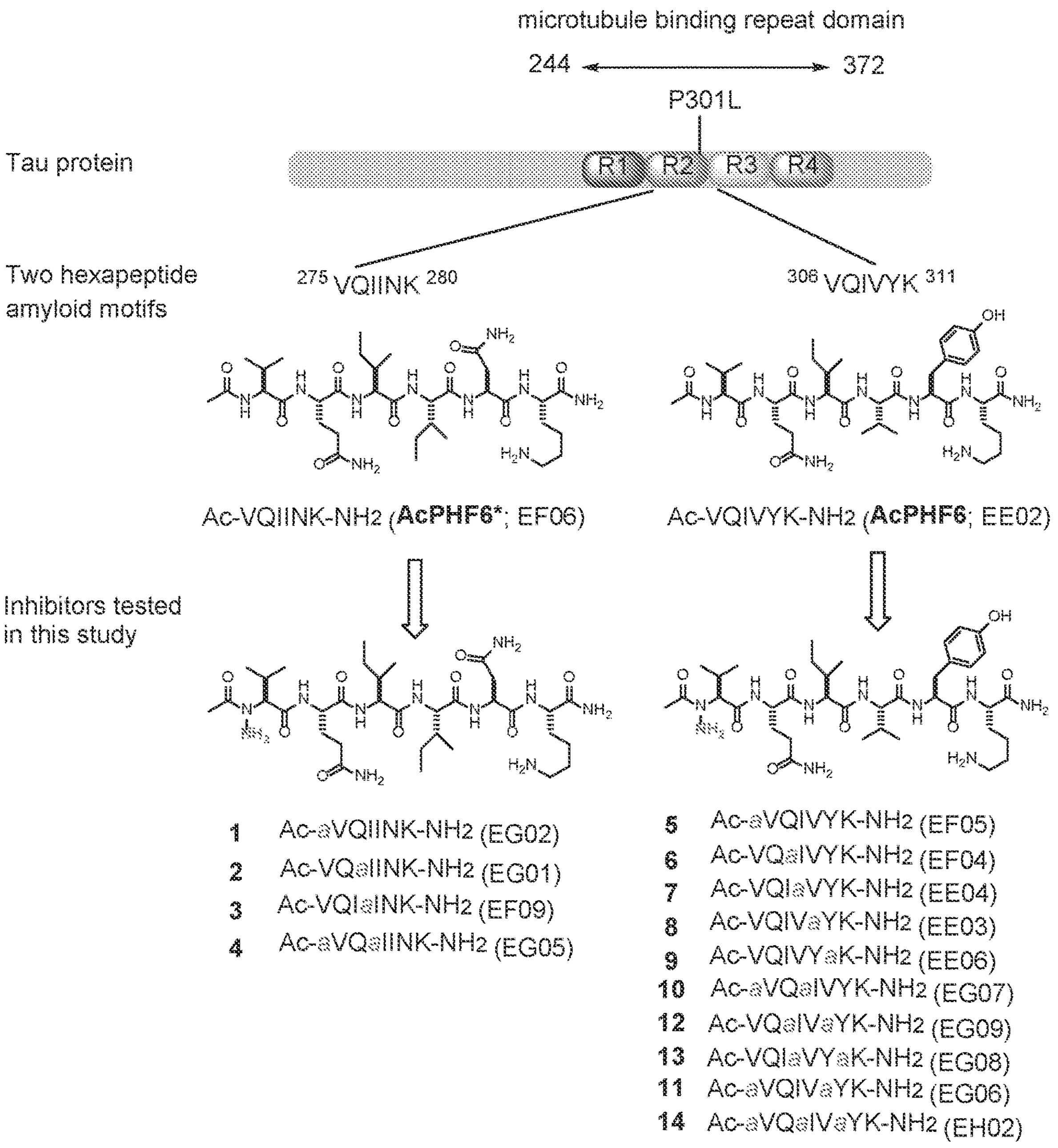
FIG. 3 shows a schematic of Tau protein and structure of peptide inhibitors tested here: Largest isoforms of Tau consist of all four-microtubule binding repeat domain R1, R2, R3 and R4 repeats. The two hexapeptide motif "VQIINK" (SEQ ID NO: 5) and "VQIVYK" (SEQ ID NO: 6) that drive Tau aggregation is located at the beginning of R2 and R3, respectively and the disease associated missense mutations that leads to Proline→Leucine substitution is located near the "VQIVYK" at position 301. The nucleotide and polypeptide sequences for human tau (0N4R) mutant, P301L, which was used for these studies is provided in SEQ ID NO: 3-4, respectively. Sequences and nomenclature of exemplary N-amino peptide inhibitors described herein for blocking Tau aggregation.

Fourteen NAP β-strand mimics were synthesized on solid support as shown in FIG. 2-3 and Table 1, supra. Analogues harboring N-amino glutamic acid (aGln) or N-amino aspartic acid (aAsn) residues were excluded since these undergo rapid intra-residue cyclization via the hydrazide during cleavage. This strategy relied on incorporation of orthogonally-protected N-amino dipeptide building blocks that are available in 3 steps from the corresponding α-amino benzyl esters. Notably, this dipeptide fragment approach allows for Fmoc SPPS of NAPs using automated, microwave-assisted HCTU/NMM condensation protocols on Rink amide MBHA resin. In contrast to canonical dipeptide (or larger) fragments, N-aminated building blocks are highly resistant to racemization during activation owing to the electron-withdrawing NHBoc substituent. Following elongation, NAPs were cleaved from the resin and purified by preparative RP-HPLC. All NAPs were characterized by $^1$H NMR and HRMS. The parent unmodified hexapeptides AcPHF6 (SEQ ID NO: 22) and AcPHF6* (SEQ ID NO: 21) were also synthesized for comparison to backbone-aminated variants.

Example 6

NAP Tau Mimics Inhibit Tau Fibrillization In Vitro

Figure 5A:
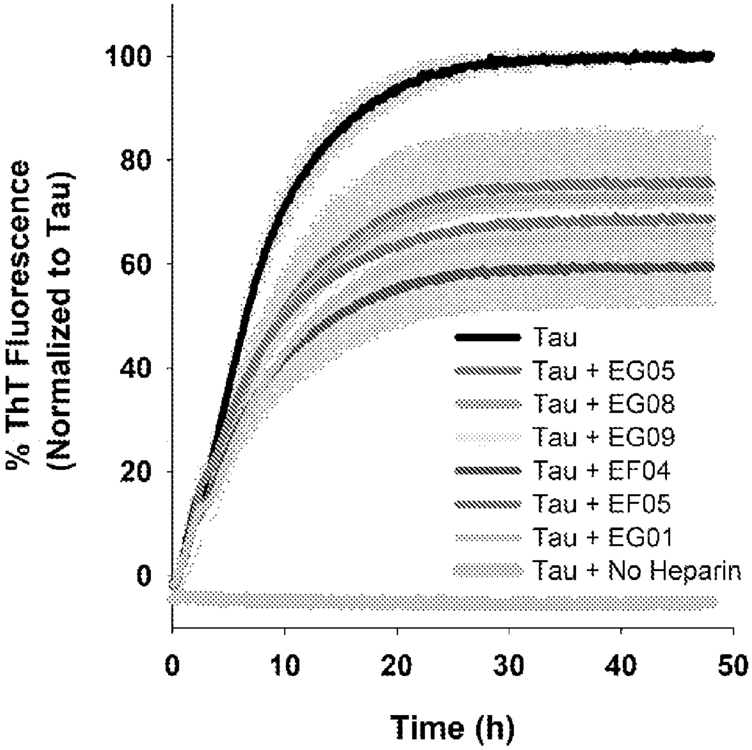
FIG. 5A-D Inhibition of Tau P301L aggregation and monomeric nature of inhibitors examined using Thioflavin T Fluorescence.
Figure 5B:
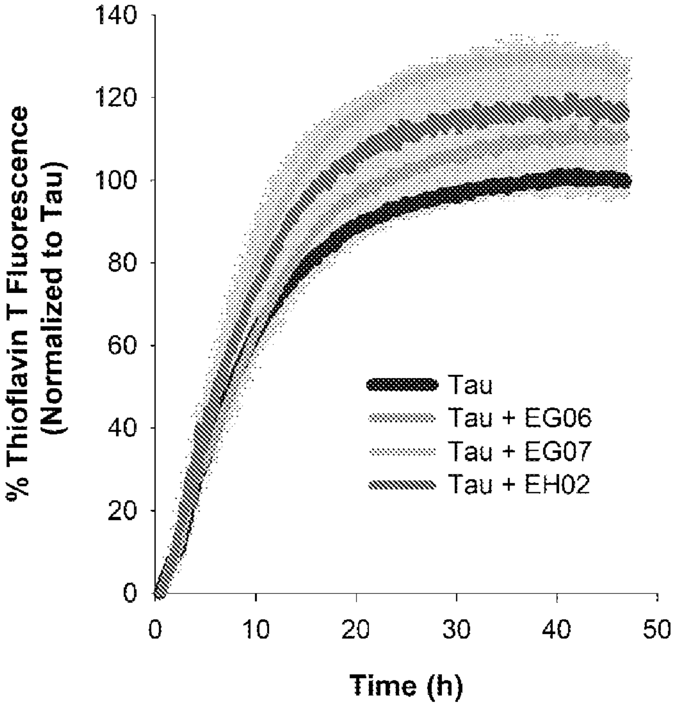
Figure 5C:
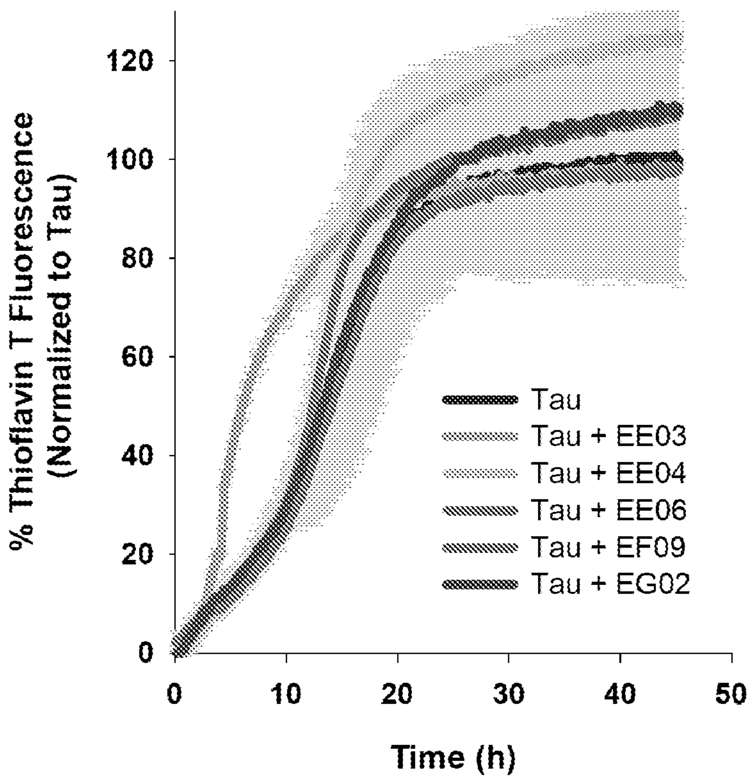
Figure 5D:
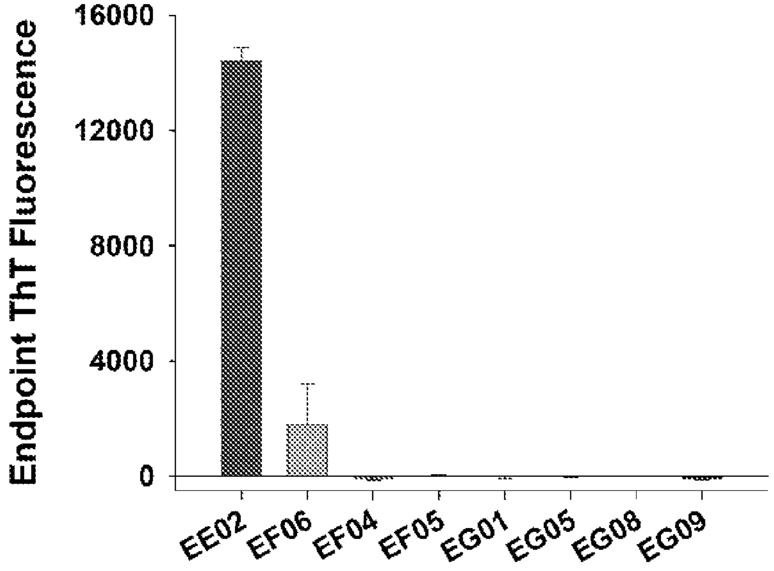

Thioflavin T (ThT), an amyloid specific fluorescent dye that binds to β-sheet assemblies, was chosen to first evaluate the effect of NAPs on recombinant tau aggregation. For these studies, full-length tau featuring a P301L mutation (FIG. 4) was expressed and purified, which is frequently observed in patients with frontotemporal dementia and parkinsonism linked to chromosome 17 (FTDP-17). This missense mutation leads to local structure destabilization around the amyloid forming region resulting in faster aggregation. Recombinant $tau_{P301L}$ aggregated in the presence of equimolar heparin sulfate ($t_{1/2}$=6.5±0.4 h) starting with a very short 0.5 h lag phase followed by a 24 h exponential growth phase. Of the 14 NAPs tested, 6 were found to significantly reduce end-point ThT fluorescence of $tau_{P301L}$ when incubated at 2-fold molar excess (FIG. 5A-C). Compounds 2 (EG01; SEQ ID NO: 8) and 4 (EG05; SEQ ID NO: 10) are mono- and di-aminated hexapeptides, respectively, derived from the R2 aggregation-prone sequence, respectively, whereas compounds 5 (EF05; SEQ ID NO: 11), 6 (EF04; SEQ ID NO: 12), 12 (EG09; SEQ ID NO: 18), and 13 (EG08; SEQ ID NO: 19) are each derived from the R3 domain sequence. Several other NAPs had no effect on end-point ThT fluorescence or lacked consistent inhibition across repeated experiments (FIG. 5B-C). In agreement with previous reports, significant aggregation of both the R2 and R3 parent peptides (AcPHF6, SEQ ID NO: 22; and AcPHF6*; SEQ ID NO: 21) was observed when incubated alone in aq. NaOAc buffer, as evidenced by intense ThT fluorescence after 48 h (FIG. 5D). In contrast, the 6 NAP inhibitors above exhibited no such fluorescence, suggesting that a single backbone N-amino group was sufficient to confer resistance to self-aggregation.

Figure 6:
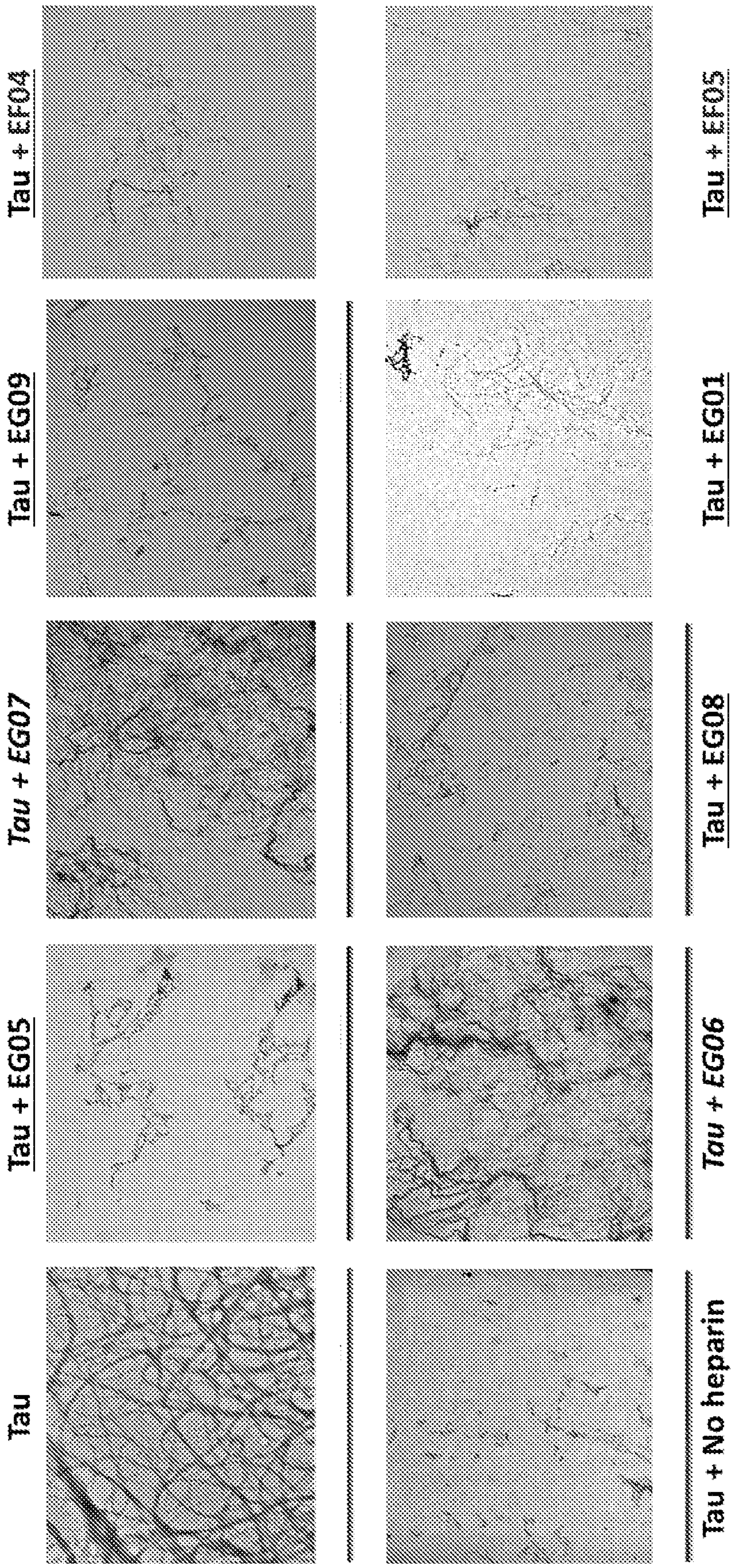
FIG. 6 shows fibril Morphology under Transmission Electron Microscope: Aggregation of Tau resulted in large, mature, and filamentous fibrils, characteristic to pathological hallmark of several neurodegenerative diseases. On incubating Tau P301L with Compounds 4 (EG05; SEQ ID NO: 10), 13 (EG08; SEQ ID NO: 19), and 12 (EG09; SEQ ID NO: 18) respectively, resulted in non-fibrillary, amorphous aggregates similar to control—with no heparin. In agreement with ThT aggregation assay, compounds 10 (EG07; SEQ ID NO: 13), 9 (EG06; SEQ ID NO: 15) and 14 (EH02; SEQ ID NO: 20) did not inhibit Tau fibril formation. Scale bars represent distance in images: 500 nm in Tau and 2 μm in rest of the images acquired on JEOL 2011 TEM at 200 kV. Inhibitors that were effective at inhibiting fibril formation are underlined and the other non-effective inhibitors are italicized.

To confirm the effect of NAPs on tau fibril growth, transmission electron microscopy (TEM) was used to visualize the morphology and maturity of fibrillar species. Heparin-induced $tau_{P301L}$ fibrils were allowed to grow over 96 h in the presence or absence of inhibitors. Untreated $tau_{P301L}$ afforded large, helical, amyloid-like filamentous fibrils. In contrast, no elongated or mature fibrils were observed in the presence of a two-fold molar excess of the 6 NAP inhibitors above. Di-N-aminated peptides 4 (EG05; SEQ ID NO: 10), 12 (EG09; SEQ ID NO: 18), and 13 (EG08; SEQ ID NO: 19) were particularly effective at blocking fibrillization, resulting in non-fibrillary amorphous aggregates similar to control wells containing $tau_{P301L}$ without heparin (FIG. 6). In the case of the mono-N-aminated peptides 2 (EG01; SEQ ID NO: 8), 5 (EF05; SEQ ID NO: 11), and 6 (EG04; SEQ ID NO: 12), short, immature rod-like fibrils were observed, indicative of a more modest effect on tau assembly (FIG. 6).

Example 7

Di-N-Aminated Hexapeptides Block the Cellular Transmission of Tau Fibrils

Figure 7A:
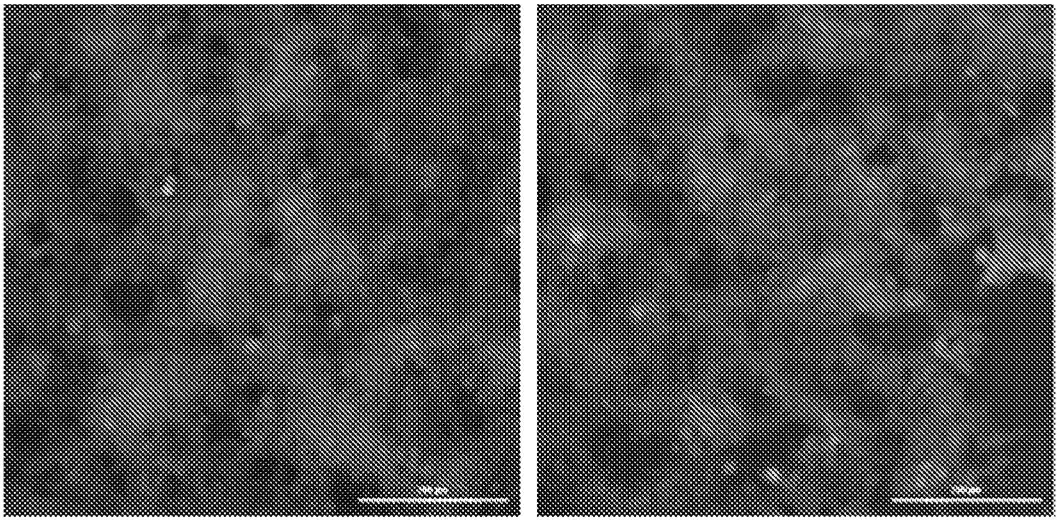
FIG. 7A-G show inhibition of monomeric Tau aggregation, seeding and propagation: In this assay format, before seeding cells, monomeric Tau was co-incubated with inhibitors for 4 days and then at a final concentration, HEK293 cells stably expressing tau-RD (P301L/V337M)-YFP, was seeded with 0.19 μM of Tau+1.9 μM or 0.009 μM of inhibitors.
Figure 7B:
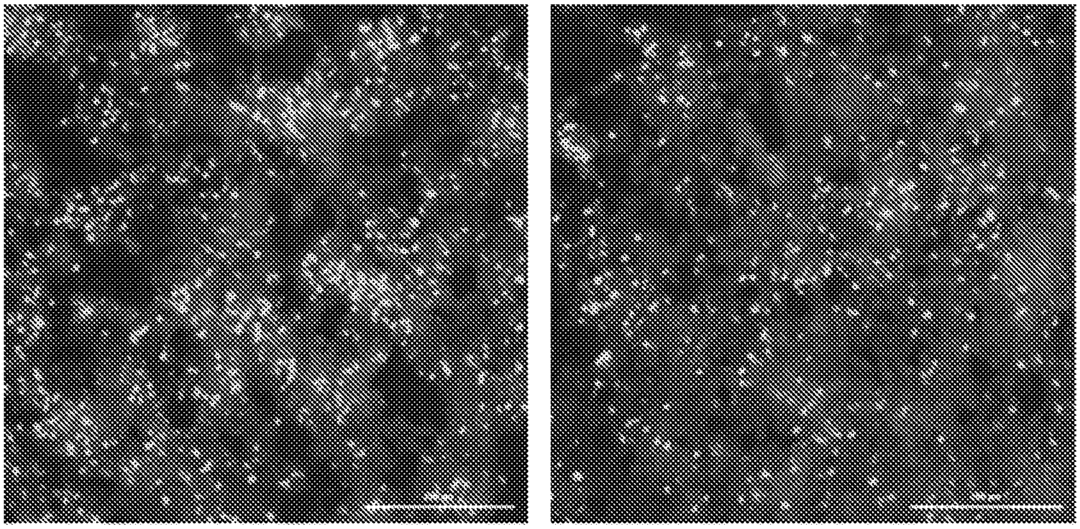
Figure 7C:
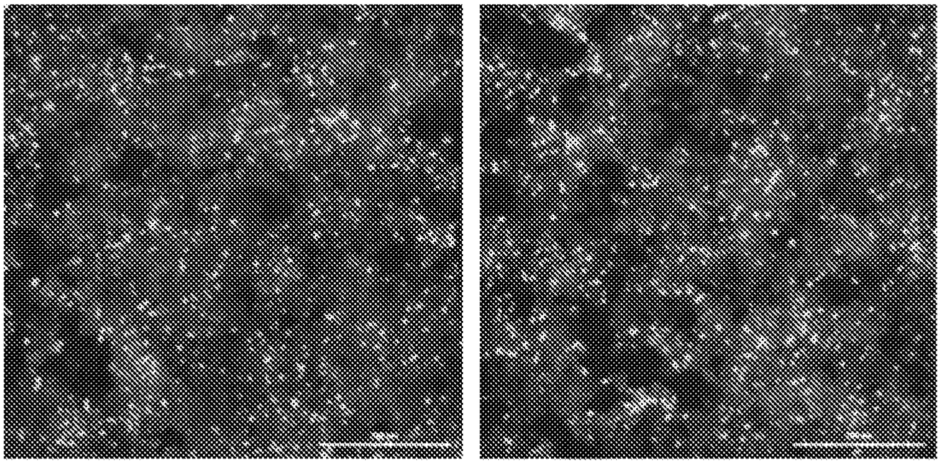
Figure 7D:
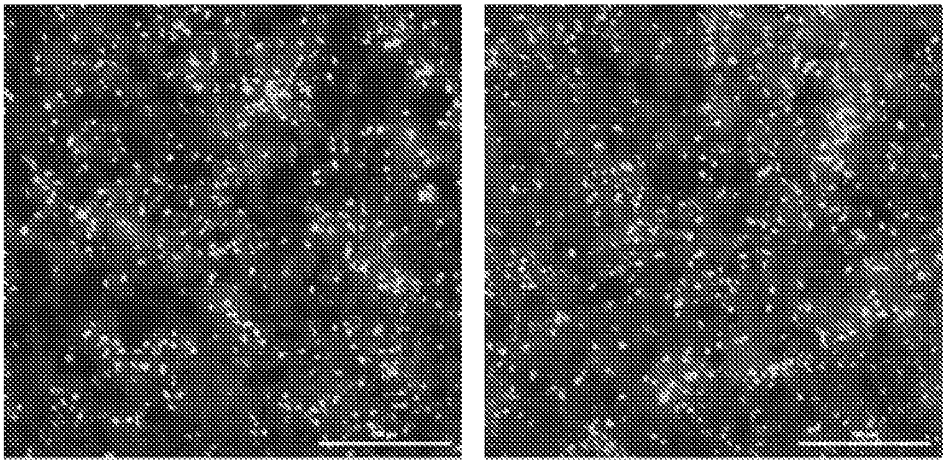
Figure 7E:
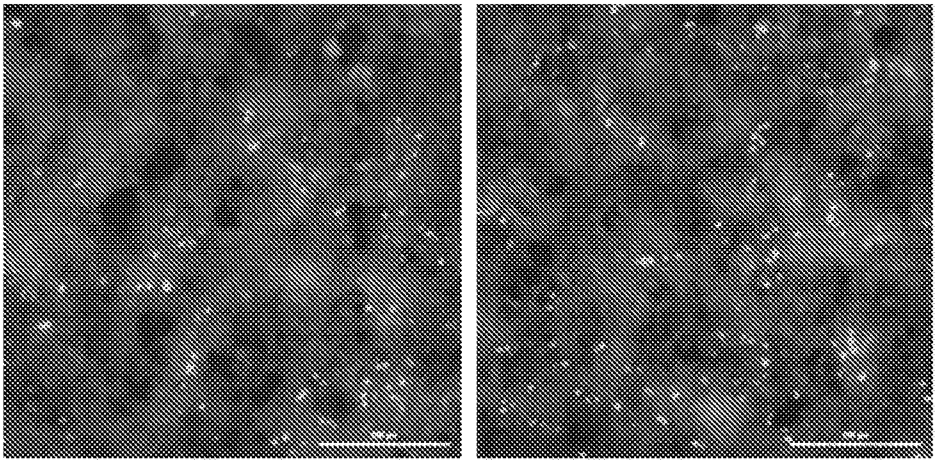
Figure 7F:
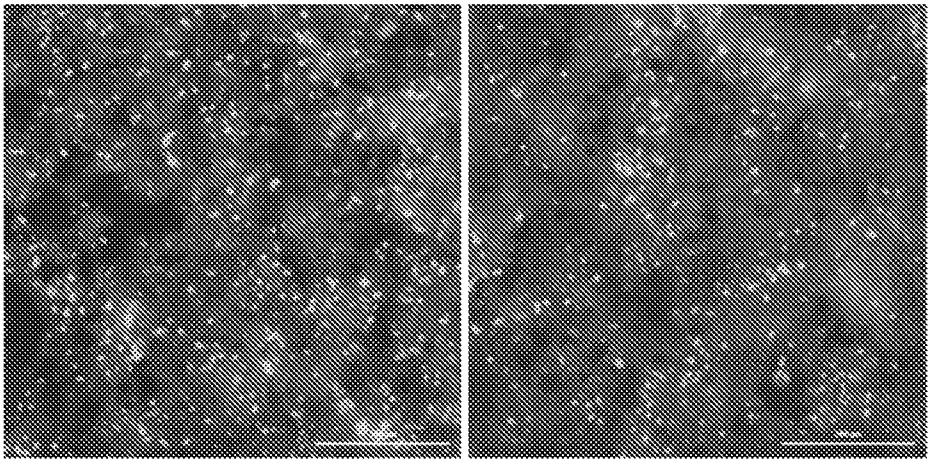
Figure 7G:
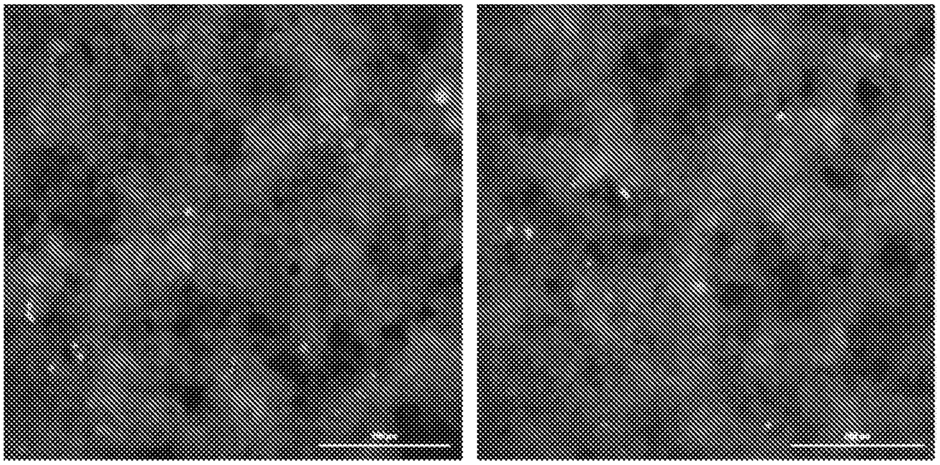
Figure 7H:
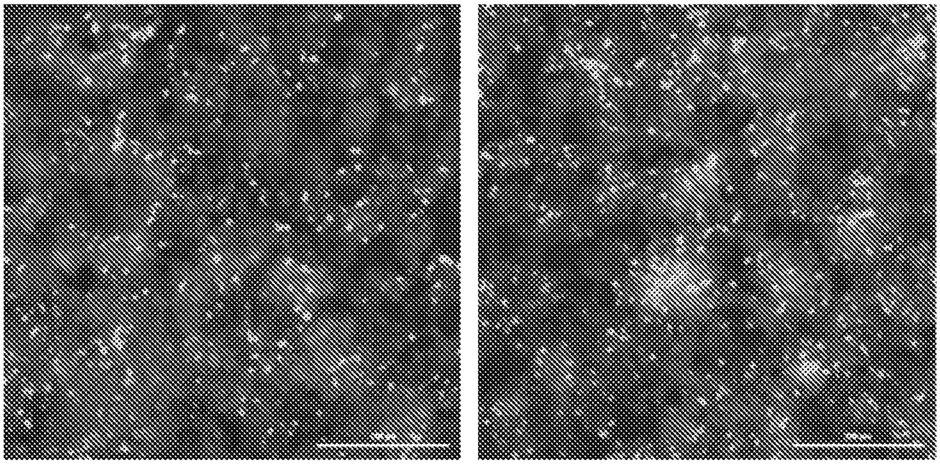
Figure 7I:
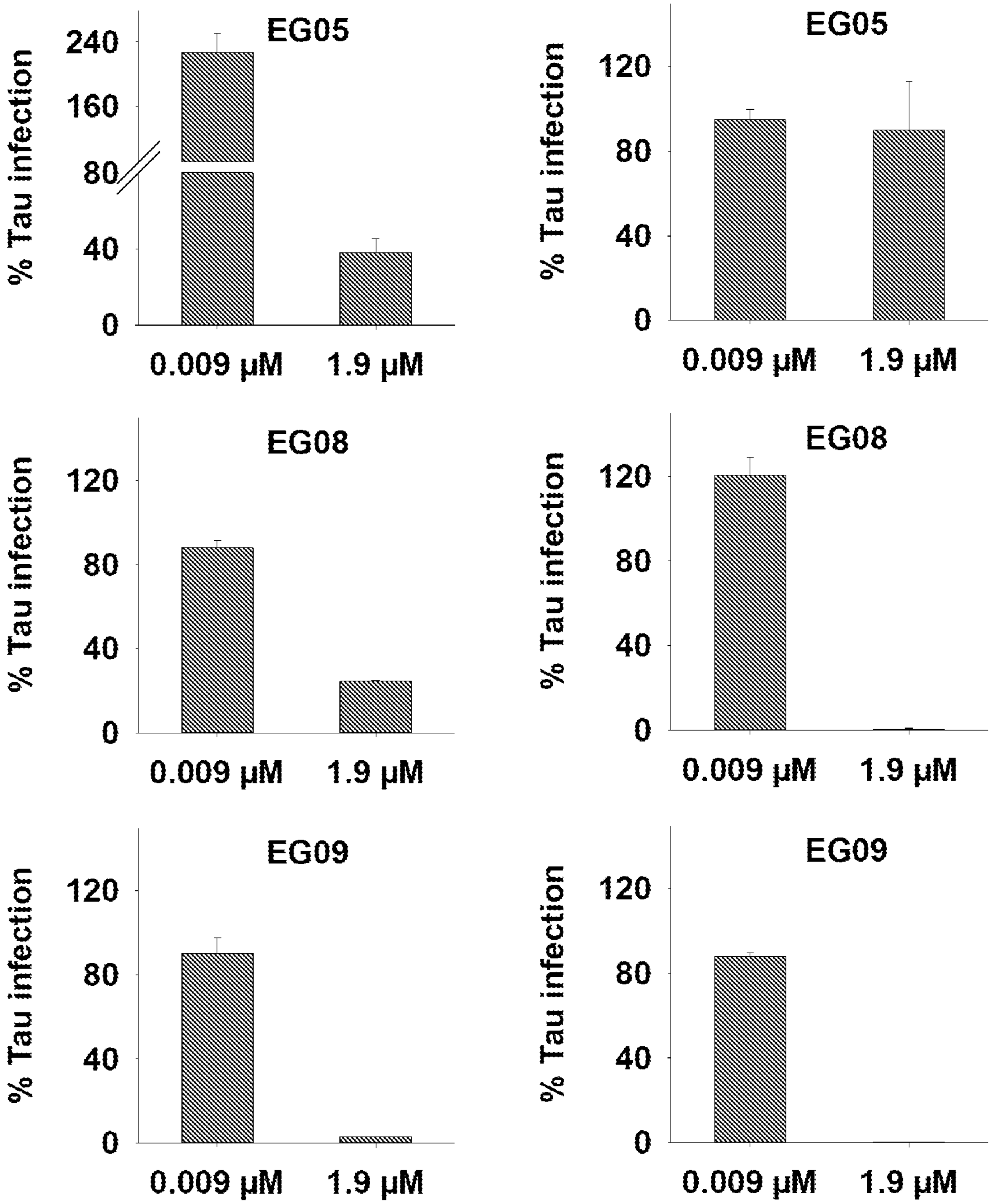
FIG. 7I shows bar graphs illustrating the number of intracellular fluorescent puncta relative to control infection wells lacking inhibitor.

Recent studies show that extracellular tau fibrils spread in a prion-like fashion from one cell to the next. This mode of propagation is important for the spread of NFTs, neuropil threads, and plaque-associated neurites-all of which contribute to the progression of AD. To test whether NAP inhibitors are able to block the seeding activity of recombinant $tau_{P301L}$, HEK293 biosensor cells were employed that stably express a tau-yellow fluorescent protein fusion (tau-RD (LM)-YFP). When these cells were treated with preformed heparin-induced fibrils of $tau_{P301L}$. a large number of intracellular tau aggregates were observed, as indicated by punctate fluorescence after 48 h. These wells exhibited a mean of 38% aggregate-containing cells over 3 separate experiments, demonstrating the ability for fibrillar $tau_{P301L}$ to enter cells and seed the aggregation of the endogenous tau-RD(LM)-YFP (FIG. 7). Given their superior anti-fibrillar activity by TEM and reduced peptide character, cell seeding experiments with di-N-aminated peptides 4 (EG05; SEQ ID NO: 10), 12 (EG09; SEQ ID NO: 18), and 13 (EG08; SEQ ID NO:19) were carried out. Pre-treatment of monomeric $tau_{P301L}$ with 1.9 μM of di-NAPs 12 (EG09; SEQ ID NO: 18) and 13 (EG08; SEQ ID NO: 19) (derived from PHF6) significantly reduced seeding capacity (FIG. 7G-H; E-F, respectively). This effect was less pronounced at 0.009 μM. Inhibitor 4 (EG05; SEQ ID NO: 10), derived from the R2 domain PHF6* motif exhibited far weaker anti-seeding activity at both high and low concentrations (FIG. 7C-D).

Figure 8:
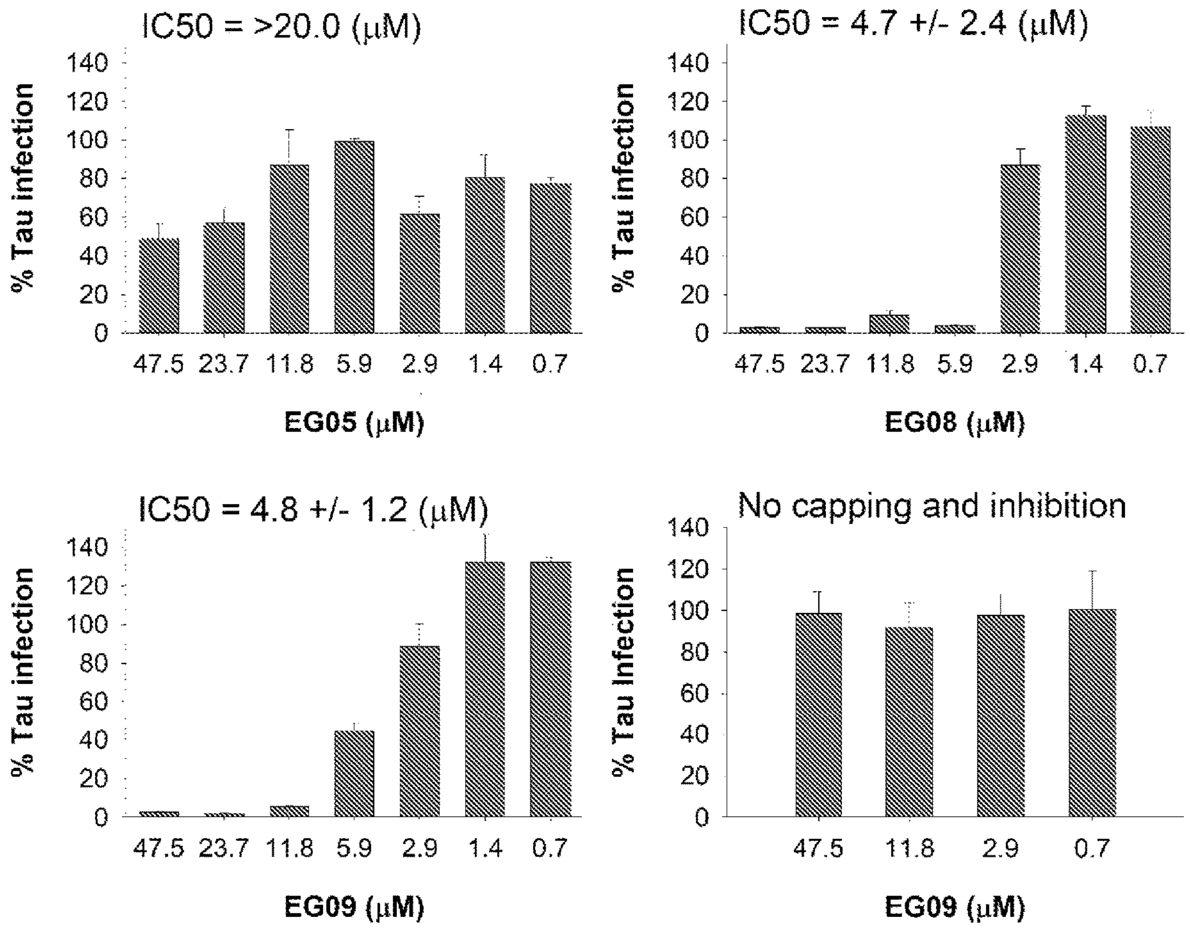
FIG. 8 shows capping pre-formed Tau P301L fibers to prevent infection: $IC_{50}$ plots depicting the quantity of inhibitors required to cap pre-formed 0.19 μM Tau P301L fibers (final concentration) from infecting HEK293 cells stably expressing tau-RD (P301L/V337M)-YFP. $IC_{50}$ values were derived from biological repeats. Compound 4 (EG05; SEQ ID NO: 10) was ineffective at capping Tau fibers whereas compounds 13 (EG08; SEQ ID NO: 19) and 12 (EG09; SEQ ID NO: 18) were more or less equally effective at capping and preventing Tau infection. As a proof of capping action, incubation step of compound 12 (EG09) with Tau fibers was omitted, resulting in no capping and thus no inhibition of Tau infection.

Given that pathogenic tau can be secreted from cells in various forms (as oligomers, aggregates, or mature fibrils), the ability of NAPs to cap pre-formed tau fibrils to block cellular transmission was tested. In this experiment NAPs were incubated with mature $tau_{P301L}$ fibrils for 36 h prior to treatment of cells expressing tau-RD(LM)-YFP. Indeed, compounds 12 (EG09; SEQ ID NO: 18) and 13 (EG08; SEQ ID NO: 19) were found to be able to effectively inhibit propagation in a dose-dependent manner. A fibril capping $IC_{50}$ in cells in the 5 μM range across 3 repeated experiments was determined (FIG. 8). These results demonstrate that the structure-based NAP mimicry approach afford ligands with anti-seeding activity irrespective of tau aggregation state.

Consistent with the seeding experiments above using monomeric $tau_{P301L}$, di-NAP 4 was generally ineffective at capping pre-formed fibrils and blocking propagation (FIG.

8). The possibility that di-NAPs 12 (EG09; SEQ ID NO: 18) and 13 (EG08; SEQ ID NO: 19) may be entering cells and inhibiting seeding by interacting with endogenous tau-RD (LM)-YFP was then considered, rather than capping extracellular pre-formed fibrils. The experiment was thus repeated without the 36-h inhibitor+mature fibril co-incubation period. Both di-NAPs failed to inhibit endogenous tau aggregation in this experiment, suggesting that the compounds interact with extracellular $tau_{P301L}$ to block cellular transmission.

Example 8

Di-NAPs are Stable in Human Serum and Non-Toxic to Neuronal Cells

Figure 9A:
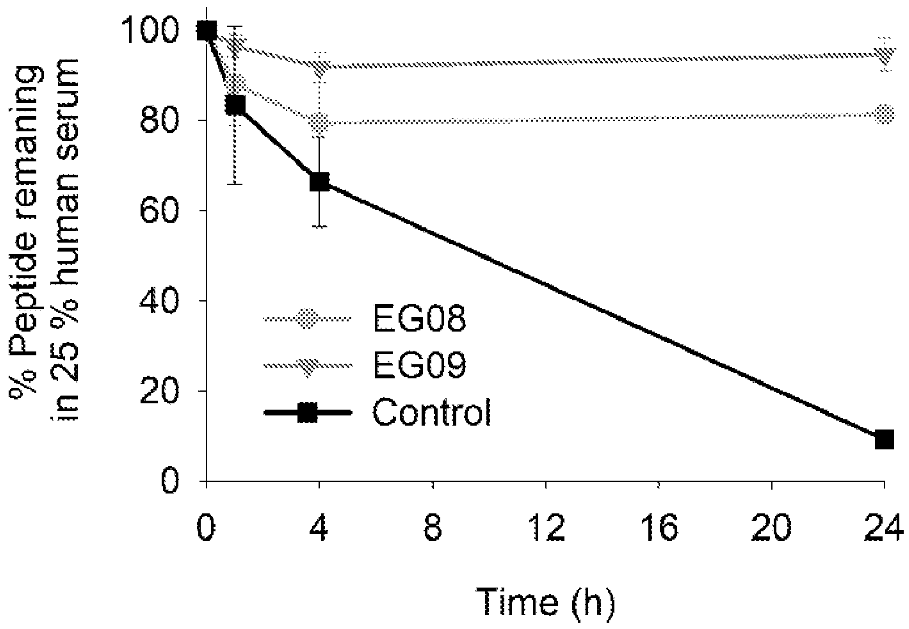
FIG. 9A-B show human serum stability and cytotoxic effect of compounds 13 (EG08; SEQ ID NO: 19) and 12 (EG09; SEQ ID NO: 18) on human neuroblastoma SH-SY5Y cells.
Figure 9B:
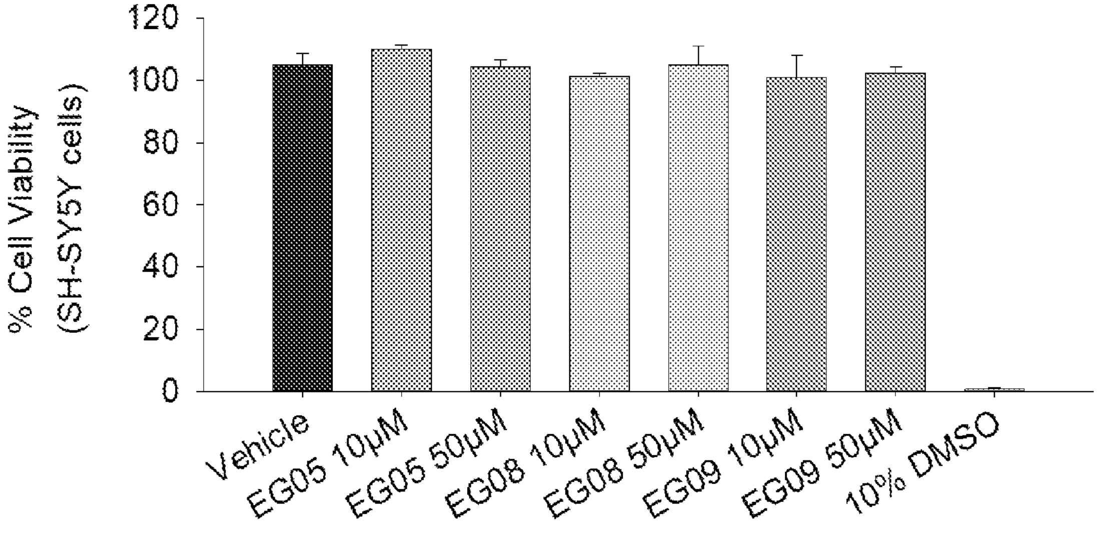

Compounds 12 (EG09; SEQ ID NO: 18) and 13 (EG08; SEQ ID NO: 19) feature two hydrazide bonds within the peptidomimetic backbone. Their utility as tau ligands in cell-based experiments would benefit from resistance to proteolytic degradation. Stability studies were carried out in human serum and degradation was monitored by RP-HPLC (FIG. 9A). Both compounds 12 (EG09; SEQ ID NO: 18) and 13 (EG08; SEQ ID NO: 19) were found to be remarkably stable in 25% human serum (>83% intact after 24 h). In contrast, an eight-residue control peptide was rapidly degraded over 24 h in the same assay. Although the parent AcPHF6 peptide could not be used as a control due to rapid self-aggregation, the stability of compounds 12 (EG09; SEQ ID NO: 18) and 13 (EG08; SEQ ID NO: 19) demonstrates the ability of N-amination to protect against peptide backbone degradation (FIG. 9B).

Cellular seeding experiments with $tau_{P301L}$ in the presence or absence of di-NAPs did not result in detectable toxicity to HEK293 biosensor cells (FIG. 9A). An MTT assay was carried out to ensure that inhibitors 12 (EG09; SEQ ID NO: 18) and 13 (EG08; SEQ ID NO: 19) are not toxic human neural cells. As shown in FIG. 9B, compounds 12 (EG09; SEQ ID NO: 18) and 13 (EG08; SEQ ID NO: 19) exhibited no appreciable toxicity toward SH-SY5Y cells up to 50 μM, or 10-fold their anti-seeding $IC_{50}$ values.

Example 9

N-Amination Imparts Backbone Conformational Constraint in Solution

Figure 10A:
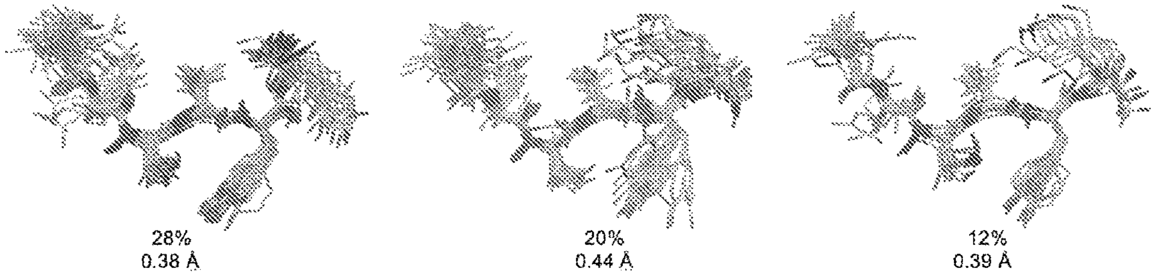
FIG. 10A shows sequential and medium to long-range NOEs observed in the ROESY spectrum along with $^3J_{NH-C\alpha H}$ coupling constant were used to derive distance and dihedral restraints for simulated annealing. About one hundred energy-minimized structures were calculated and grouped into eighteen dusters. Structures of top three clusters are shown with their populations and average backbone RMSD relative to the cluster average.
Figure 10B:
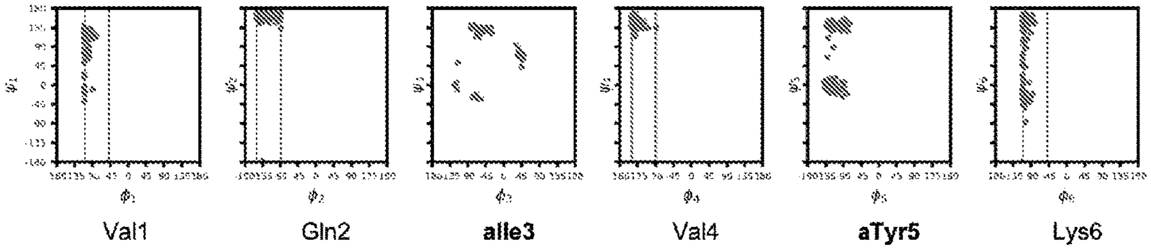
FIG. 10B shows residue-wise Ramachandran plots for the solution-derived structural ensemble. Green lines mark the dihedral restraints derived from the $^3J_{NH-C\alpha H}$ coupling constants.

Di-NAPs that cap mature tau fibrils are expected to adopt parallel-sheet-like conformations. The X-ray crystallographic structure of a model di-N-aminated tripeptide previously demonstrated its self-association as a dimeric species with extended backbone geometries. To gain insight into the solution structure of the lead tau ligands, 2D-NMR spectroscopy was carried out followed by simulated annealing. While AcPHF6 was insoluble in water, gCOSY, TOCSY, and ROESY NMR spectra in 9:1 $H_2O$:$D_2O$ for compounds 12 (EG09; SEQ ID NO: 18) and 13 (EG08; SEQ ID NO: 19) were able to be obtained. NMR spectra in $D_2O$ were remarkably well resolved and devoid of significant minor rotamers despite the presence of two N-substituted amide bonds. Moreover, inter-residue NOEs were limited to correlations consistent with an extended solution conformation ($i_\alpha \rightarrow i+1_{NH}$). Though short linear peptides are expected to be highly flexible in solution, the absence of characteristic turn correlations suggests conformational restriction imparted by the N-amino groups. Distance-restrained simulated annealing and clustering based on backbone dihedral angles afforded ensembles of the three most populated conformers of compound 12 (EG09; SEQ ID NO: 18) (FIG. 10). These clusters revealed high convergence of φ and ψ torsions within the Gln2 and Val3 residues to the β-sheet region of Ramachandran space. In contrast, the N-aminated aIle3 and aTyr5 residues exhibit greater conformational heterogeneity. This pattern was also observed in the case of di-NAP 13 (EG08; SEQ ID NO: 19). To specifically parse the conformational impact of N-amination, unrestrained conventional MD simulations on compound 12 (EG09; SEQ ID NO: 18) and AcPHF6 were carried out. Ramachandran plots for the 400 ns simulation again showed that N-amination severely restricts accessible backbone torsions of the preceding residue. It was previously shown that NAPs readily engage in intra-residue $C^6$ H-bonds between the N—$NH_2$ donor and the carbonyl-O acceptor, even in protic solvent. Coupled with the constraint imposed on the preceding residue, the hydrazide bond thus may serve to further stabilize β-sheet-like conformations that recognize fibrillar tau.

Example 10

Di-NAP 12 does not Inhibit $A\beta_{42}$ Aggregation In Vitro

Figure 11:
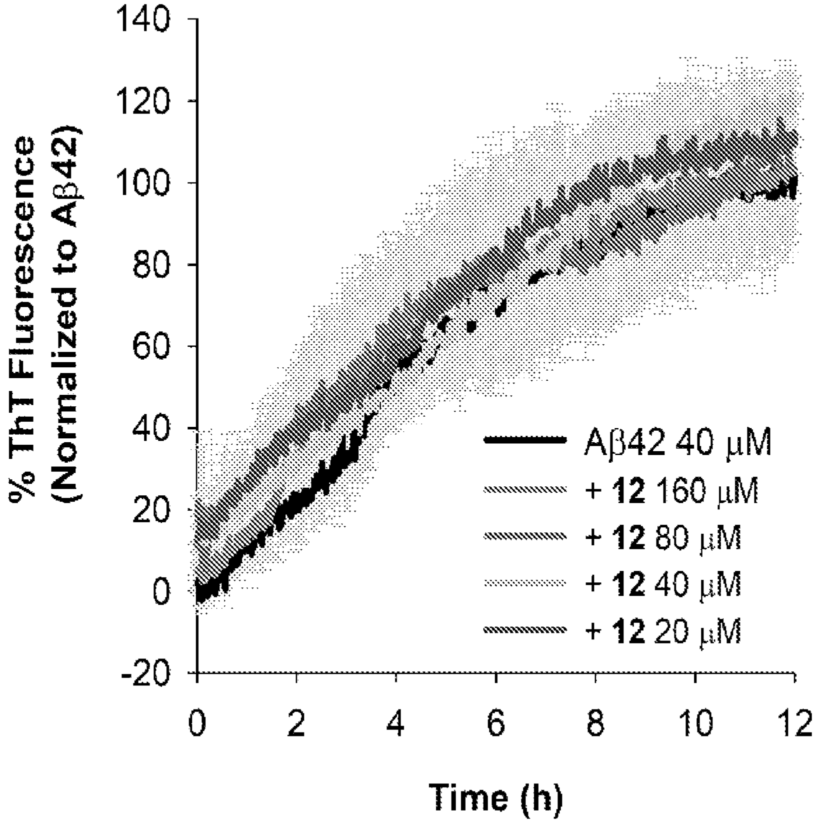
FIG. 11 shows ThT fluorescence assay with $A\beta_{42}$ in the presence or absence of compound 12 (EG09; SEQ ID NO: 18) showed no inhibitory effect on $A\beta_{42}$ aggregation.

Many small molecule protein aggregation inhibitors exhibit undesired promiscuity. A peptidomimetic approach to tau inhibition offers prospects for achieving selectivity over other amyloids rich in β structure. As a preliminary test, the best-performing tau mimic, compound 12 (EG09; SEQ ID NO: 18), was selected and its effect on $A\beta_{42}$ aggregation in vitro was determined (FIG. 11). Incubation of synthetic, full-length $A\beta_{42}$ (40 μM) in the presence of ThT and various concentrations of compound 12 (EG09; SEQ ID NO: 18) resulted in strong fluorescence indicative of aggregation. Di-NAP compound 12 (EG09; SEQ ID NO: 18) exhibited no inhibitory effect on Aβ42 aggregation up to a 4-fold molar excess (160 μM). Similarly, no effect on lag-time was observed at any of the concentrations tested. Compound 12 (EG09; SEQ ID NO: 18) thus exhibits in vitro selectivity for tau over $A\beta_{42}$, which also undergoes parallel β-sheet assembly driven by a hydrophobic hexapeptide core motif.

Described herein is the design, synthesis, and biological evaluation of a novel class of β-strand mimics that block tau aggregation and propagation. Using an amide-to-hydrazide replacement strategy, a positional scan of aggregation-prone peptide sequences derived from the R2 and R3 domain of tau was carried out. Several NAP analogues inhibited the fibrillization of recombinant full-length tau as well as its seeding capacity in an in-cell aggregation assay. Key features of the described NAP inhibitors include increased conformational rigidity, resistance toward self-aggregation, and remarkable stability toward serum proteases. The most effective inhibitor of tau fibrillization and seeding showed no effect on the in vitro aggregation of $A\beta_{42}$. Discrimination between structurally related β-rich assemblies is potentially enabled by NAPs, which exhibit a full complement of side chains in a minimalist single-strand design. In using the structure of tau to guide the design of its own inhibitors, this work sets the stage for the development of selective ligands of other pathogenic amyloids. Given that disease-associated conformational strains of tau are known to propagate in vivo with high fidelity, it is also expected that a NAP-based strategy can be used to target unique structural motifs within such polymorphs. The current study thus provides a rational basis for the design of soluble β-strand mimics with high levels of specificity.

What is claimed:

1. A compound of formula (I), or a pharmaceutically acceptable salt thereof, (I)

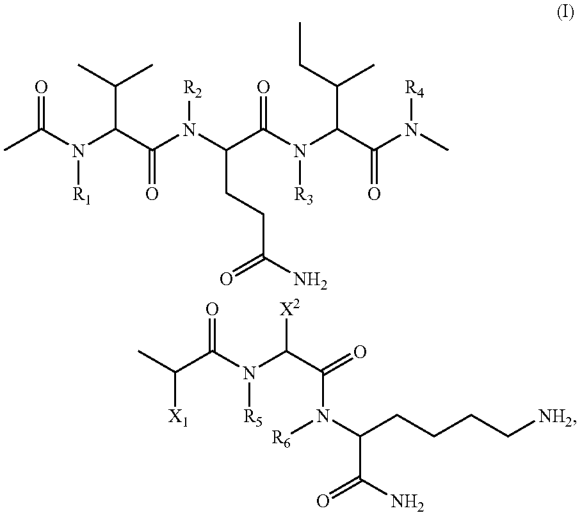

wherein:

$X^1$ is

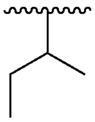 [SMILES: *C(C)CC] or 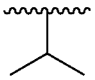 ;

$X^2$ is

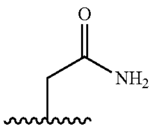 or 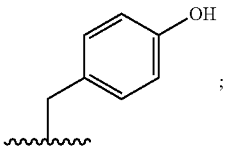 ;

$R^1$, $R^2$, $R^3$, $R^4$, $R^5$, and $R^6$, at each occurrence, are each independently hydrogen or —$NHR^7$, with the proviso that at least one of $R^1$, $R^2$, $R^3$, $R^4$, $R^5$, and $R^6$ is not hydrogen;

$R^7$, at each occurrence, is independently hydrogen, $C_{1-6}$alkyl, $C_{1-6}$haloalkyl, $C_{1-6}$hydroxyalkyl, —$C_{1-3}$alkylene-$OR^{1a}$, —$C(O)R^{1a}$, —$CO_2R^{1a}$, —C(O) $NR^{1b}R^{1c}$, —$SO_2R^{1a}$, $G^1$, —C(O) $G^1$, —$CO_2G^1$, —$C(O)NR^{1b}G^1$, —$SO_2G^1$, —$C_{1-3}$alkylene-$G^1$, —C(O)—$C_{1-3}$alkylene-$G^1$, —$CO_2$-$C_{1-3}$alkylene-$G^1$, —$C(O)NR^{1b}$—$C_{1-3}$alkylene-$G^1$, or —$SO_2$-$C_{1-3}$alkylene-$G^1$;

$R^{1a}$, $R^{1b}$, and $R^{1c}$, at each occurrence, are each independently hydrogen, $C_{1-6}$alkyl, $C_{1-6}$haloalkyl, $C_{1-6}$hydroxyalkyl, —$C_{1-3}$alkylene-$OC_{1-6}$alkyl, $C_{3-8}$cycloalkyl, or —$C_{1-3}$alkylene-$C_{3-8}$cycloalkyl, wherein the $C_{3-8}$cycloalkyl in $R^{1a}$, $R^{1b}$, and $R^{1c}$ is optionally substituted with 1-4 substituents independently selected from halogen, $C_{1-4}$alkyl, and $C_{1-4}$haloalkyl;

$G^1$ is a 6- to 12-membered aryl, a 5- to 12-membered heteroaryl containing 1-2 heteroatoms, or a 3- to 12-membered carbocyclyl, wherein $G^1$ is optionally substituted with 1-5 substituents, each independently halogen, cyano, $R^x$, —$OR^x$, —$C_{1-3}$alkylene-$OR^x$, —$N(R^x)_2$, —$C(O)R^x$, —$CO_2R^x$, —$C(O)N(R^x)_2$, or —$SO_2R^x$; and $R^x$ at each occurrence, is independently $C_{1-4}$alkyl, $C_{1-4}$haloalkyl, $C_{1-6}$hydroxyalkyl, $C_{3-8}$cycloalkyl, or —$C_{1-3}$alkylene-$C_{3-8}$cycloalkyl, wherein the $C_{3-8}$cycloalkyl in $R^x$ is optionally substituted with 1-4 substituents, each independently selected from halogen, $C_{1-4}$alkyl, and $C_{1-4}$haloalkyl.

2. The compound of claim 1, or a pharmaceutically acceptable salt thereof, wherein $R^7$ is hydrogen, $C_{1-6}$alkyl, —$C(O)R^{1a}$, —$CO_2R^{1a}$, —$SO_2G^1$, —$C_{1-3}$alkylene-$G^1$, or —$CO_2$—$C_{1-3}$alkylene-$G^1$.

3. The compound of claim 2, or a pharmaceutically acceptable salt thereof, wherein $G^1$ is the optionally substituted 6- to 12-membered aryl.

4. The compound of claim 3, or a pharmaceutically acceptable salt thereof, wherein the ring system of the optionally substituted 6- to 12-membered aryl is a phenyl.

5. The compound of claim 2, or a pharmaceutically acceptable salt thereof, wherein $R^7$ is hydrogen or —$CO_2C_{1-6}$alkyl.

6. The compound of claim 1, or a pharmaceutically acceptable salt thereof, wherein $X^1$ is

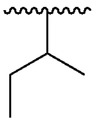

and $X^2$ is

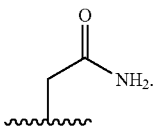 [SMILES: *CC(N)=O]

7. The compound of claim 1, or a pharmaceutically acceptable salt thereof, wherein $X^1$ is

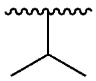

and $X^2$ is

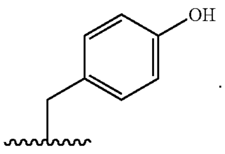 [SMILES: *Cc1ccc(O)cc1]

8. The compound of claim 1, or a pharmaceutically acceptable salt thereof, wherein $R^1$ is —$NHR^7$ and $R^2$, $R^3$, $R^4$, $R^5$, and $R^6$ are each hydrogen.

9. The compound of claim 1, or a pharmaceutically acceptable salt thereof, wherein $R^3$ is —$NHR^7$ and $R^1$, $R^2$, $R^4$, $R^5$, and $R^6$ are each hydrogen.

10. The compound of claim 1, or a pharmaceutically acceptable salt thereof, wherein $R^4$ is —$NHR^7$, and $R^1$, $R^2$, $R^3$, $R^5$, and $R^6$ are each hydrogen.

11. The compound of claim 1, or a pharmaceutically acceptable salt thereof, wherein $R^5$ is —$NHR^7$, and $R^1$, $R^2$, $R^3$, $R^4$, and $R^6$ are each hydrogen.

12. The compound of claim 1, or a pharmaceutically acceptable salt thereof, wherein $R^6$ is —$NHR^7$, and $R^1$, $R^2$, $R^3$, $R^4$, and $R^5$ are each hydrogen.

13. The compound of claim 1, or a pharmaceutically acceptable salt thereof, wherein $R^1$ and $R^3$ are each —$NHR^7$, and $R^2$, $R^4$, $R^5$, and $R^6$ are each hydrogen.

14. The compound of claim 1, or a pharmaceutically acceptable salt thereof, wherein $R^1$ and $R^5$ are each —$NHR^7$, and $R^2$, $R^3$, $R^4$, and $R^6$ are each hydrogen.

15. The compound of claim 1, or a pharmaceutically acceptable salt thereof, wherein $R^3$ and $R^5$ are each —$NHR^7$, and $R^1$, $R^2$, $R^4$, and $R^6$ are each hydrogen.

16. The compound of claim 1, or a pharmaceutically acceptable salt thereof, wherein $R^4$ and $R^6$ are each —$NHR^7$, and $R^1$, $R^2$, $R^3$, and $R^5$ are each hydrogen.

17. The compound of claim 1, or a pharmaceutically acceptable salt thereof, wherein $R^1$, $R^3$, and $R^5$ are each —$NHR^7$, and $R^2$, $R^4$, and $R^6$ are each hydrogen.

18. The compound of claim 1, wherein the compound is a compound of formula (I-a), (I-a)

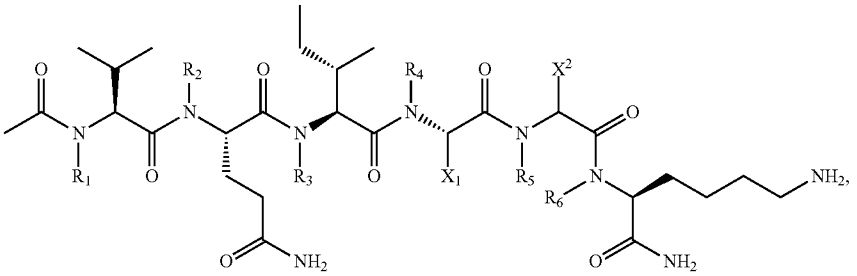

or a pharmaceutically acceptable salt thereof, wherein:

$X^1$ is

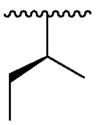

or

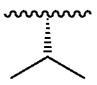

and $X^2$ is

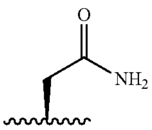

or

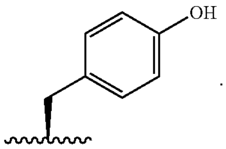

.

19. The compound of claim 1, wherein the compound is selected from:
(SEQ ID NO: 7)
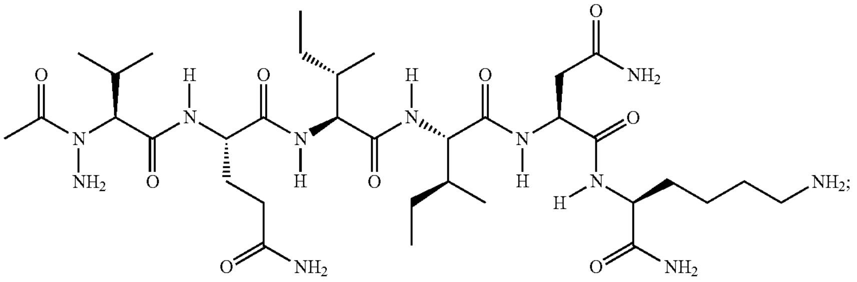
(1, EG02)
Ac-aVal-Gln-Ile-Ile-Asn-Lys-$NH_2$
(SEQ ID NO: 8)
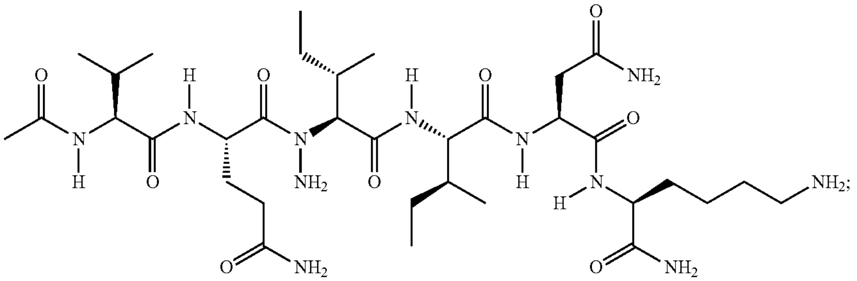
(2, EG01)
Ac-Val-Gln-aIle-Ile-Asn-Lys-$NH_2$
(SEQ ID NO: 9)
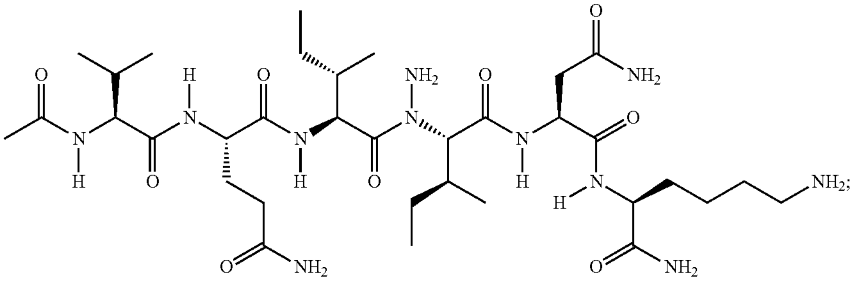
(3, EG09)
Ac-Val-Gln-Ile-aIle-Asn-Lys-$NH_2$
(SEQ ID NO: 10)
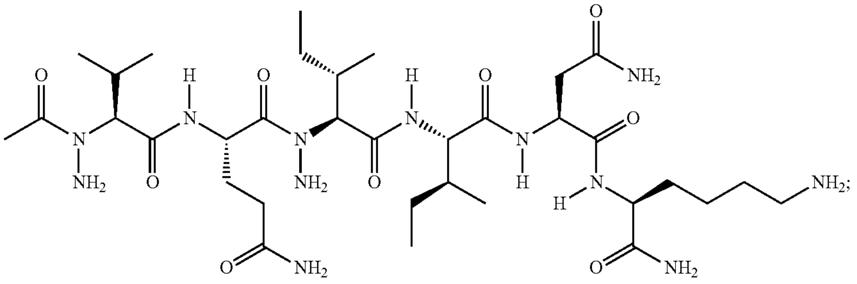
(4, EG05)
Ac-aVal-Gln-aIle-Ile-Asn-Lys-$NH_2$ -continued
(SEQ ID NO: 11)
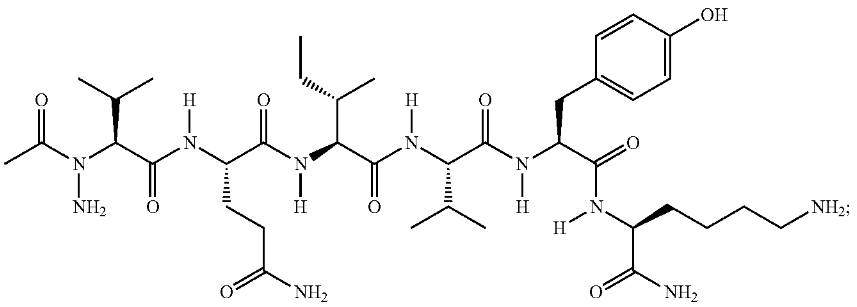
(5, EF05)
Ac-aVal-Gln-Ile-
Val-Tyr-Lys-$NH_2$
(SEQ ID NO: 12)
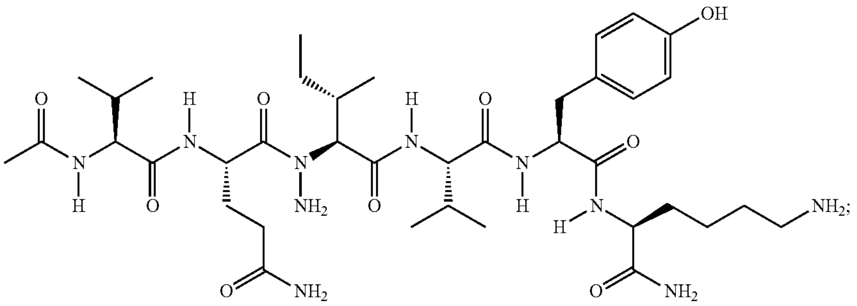
(6, EF04)
Ac-Val-Gln-aIle-
Val-Tyr-Lys-$NH_2$
(SEQ ID NO: 13)
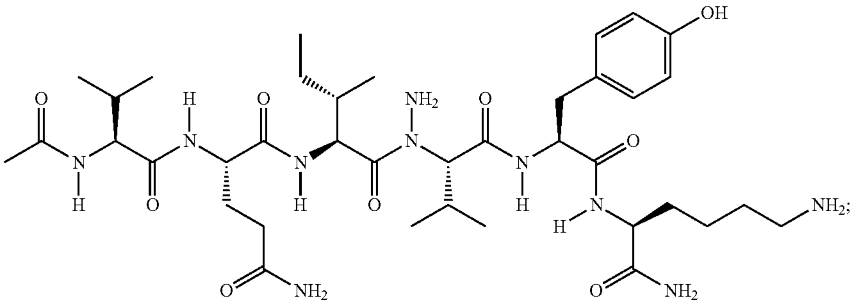
(7, EE04)
Ac-Val-Gln-Ile-
aVal-Tyr-Lys-$NH_2$
(SEQ ID NO: 14)
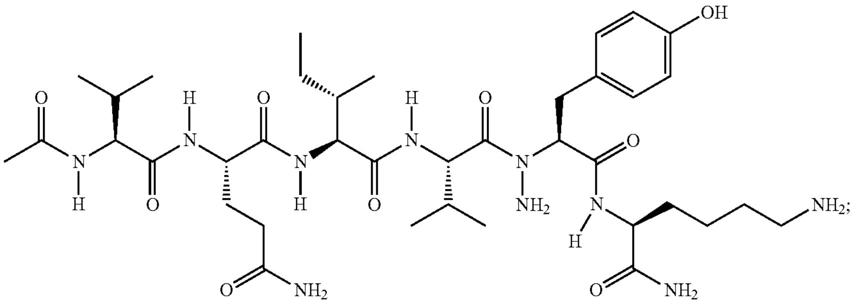
(8, EE03)
Ac-Val-Gln-Ile-Val-
aTyr-Lys-$NH_2$ -continued
(SEQ ID NO: 15)
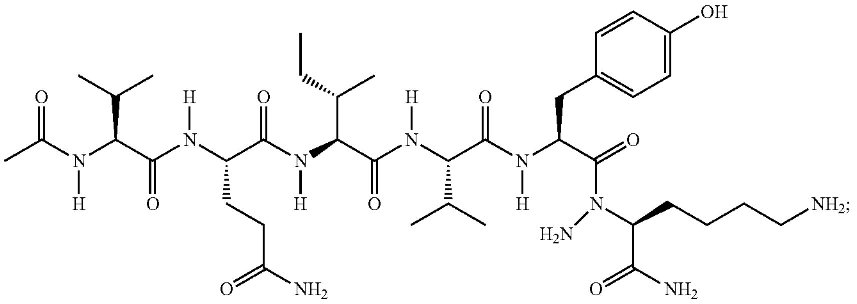
(9, EE06)
Ac-Val-Gln-Ile-Val-
Tyr-aLys-$NH_2$
(SEQ ID NO: 16)
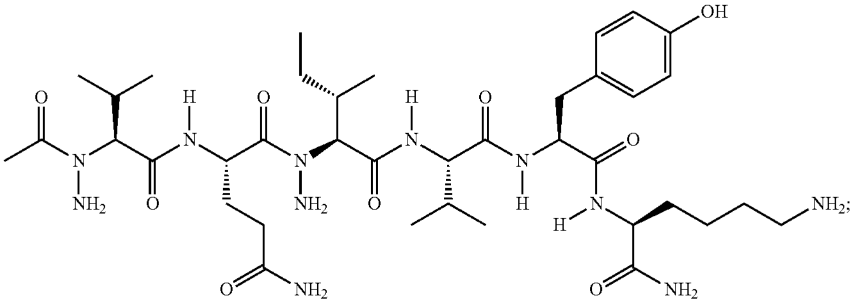
(10, EG07)
Ac-aVal-Gln-aIle-
Val-Tyr-Lys-$NH_2$
(SEQ ID NO: 17)
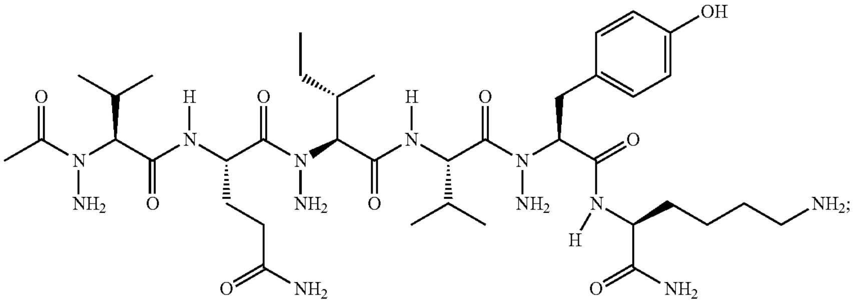
(11, EG06)
Ac-aVal-Gln-Ile-
Val-aTyr-Lys-$NH_2$
(SEQ ID NO: 18)
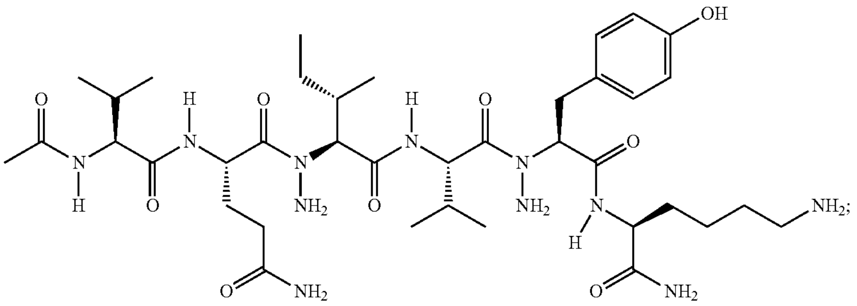
(12, EG09)
Ac-Val-Gln-aIle-
Val-aTyr-Lys-$NH_2$ -continued (SEQ ID NO: 19)

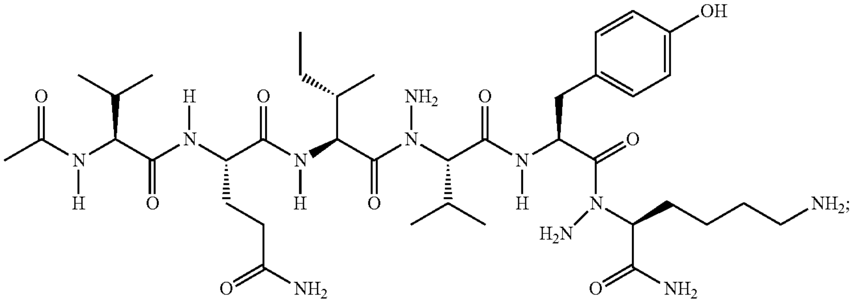

or (13, EG08)
Ac-Val-Gln-aIle-
aVal-Tyr-aLys-$NH_2$ (SEQ ID NO: 20)

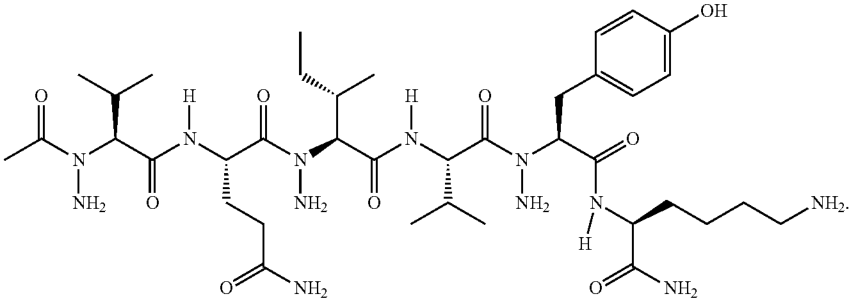

(14, EH02)
Ac-aVal-Gln-aIle-
Val-aTyr-Lys-$NH_2$

20. The compound of claim 1, wherein the compound is stable in human blood, serum, plasma, or cerebrospinal fluid.

21. The compound of claim 1, wherein the compound is non-toxic to human neuronal cells.

22. A method for inhibiting tau protein fibrilization or aggregation, the method comprising contacting tau protein with one or more compounds of claim 1.

23. The method of claim 22, wherein the compounds comprise one or more of compounds 1-14 (SEQ ID NO: 7-20).

24. The method of claim 22, wherein the compounds comprise one or more of compounds 12 or 13 (SEQ ID NO: 18 or 19).

25. The method of claim 22, wherein the compounds have a concentration of at least 2-fold molar excess relative to the concentration of tau protein present during the contacting step.

26. A method for preventing cellular transmission of neurofibrillary tangles (NFTs), the method comprising contacting cells containing NFTs with one or more compounds of claim 1.

27. The method of claim 26, wherein the compounds comprise one or more of Compounds 1-14 (SEQ ID NO: 7-20).

28. The method of claim 26, wherein the compounds comprise one or more of Compounds 12 or 13 (SEQ ID NO: 18 or 19).

* * * * *

SEQUENCE LISTING

<160> NUMBER OF SEQ ID NOS: 22

<210> SEQ ID NO 1
<211> LENGTH: 1326
<212> TYPE: DNA
<213> ORGANISM: Homo sapiens
<220> FEATURE:
<221> NAME/KEY: CDS
<222> LOCATION: (1)..(1326)

<400> SEQUENCE: 1 atg gct gag ccc cgc cag gag ttc gaa gtg atg gaa gat cac gct ggg 48
Met Ala Glu Pro Arg Gln Glu Phe Glu Val Met Glu Asp His Ala Gly
1 5 10 15 acg tac ggg ttg ggg gac agg aaa gat cag ggg ggc tac acc atg cac 96
Thr Tyr Gly Leu Gly Asp Arg Lys Asp Gln Gly Gly Tyr Thr Met His
20 25 30 caa gac caa gag ggt gac acg gac gct ggc ctg aaa gaa tct ccc ctg 144
Gln Asp Gln Glu Gly Asp Thr Asp Ala Gly Leu Lys Glu Ser Pro Leu
35 40 45 cag acc ccc act gag gac gga tct gag gaa ccg ggc tct gaa acc tct 192
Gln Thr Pro Thr Glu Asp Gly Ser Glu Glu Pro Gly Ser Glu Thr Ser
50 55 60 gat gct aag agc act cca aca gcg gaa gat gtg aca gca ccc tta gtg 240
Asp Ala Lys Ser Thr Pro Thr Ala Glu Asp Val Thr Ala Pro Leu Val
65 70 75 80 gat gag gga gct ccc ggc aag cag gct gcc gcg cag ccc cac acg gag 288
Asp Glu Gly Ala Pro Gly Lys Gln Ala Ala Ala Gln Pro His Thr Glu
85 90 95 atc cca gaa gga acc aca gct gaa gaa gca ggc att gga gac acc ccc 336
Ile Pro Glu Gly Thr Thr Ala Glu Glu Ala Gly Ile Gly Asp Thr Pro
100 105 110 agc ctg gaa gac gaa gct gct ggt cac gtg acc caa gct cgc atg gtc 384
Ser Leu Glu Asp Glu Ala Ala Gly His Val Thr Gln Ala Arg Met Val
115 120 125 agt aaa agc aaa gac ggg act gga agc gat gac aaa aaa gcc aag ggg 432
Ser Lys Ser Lys Asp Gly Thr Gly Ser Asp Asp Lys Lys Ala Lys Gly
130 135 140 gct gat ggt aaa acg aag atc gcc aca ccg cgg gga gca gcc cct cca 480
Ala Asp Gly Lys Thr Lys Ile Ala Thr Pro Arg Gly Ala Ala Pro Pro
145 150 155 160 ggc cag aag ggc cag gcc aac gcc acc agg att cca gca aaa acc ccg 528
Gly Gln Lys Gly Gln Ala Asn Ala Thr Arg Ile Pro Ala Lys Thr Pro
165 170 175 ccc gct cca aag aca cca ccc agc tct ggt gaa cct cca aaa tca ggg 576
Pro Ala Pro Lys Thr Pro Pro Ser Ser Gly Glu Pro Pro Lys Ser Gly
180 185 190 gat cgc agc ggc tac agc agc ccc ggc tcc cca ggc act ccc ggc agc 624
Asp Arg Ser Gly Tyr Ser Ser Pro Gly Ser Pro Gly Thr Pro Gly Ser
195 200 205 cgc tcc cgc acc ccg tcc ctt cca acc cca ccc acc cgg gag ccc aag 672
Arg Ser Arg Thr Pro Ser Leu Pro Thr Pro Pro Thr Arg Glu Pro Lys
210 215 220 aag gtg gca gtg gtc cgt act cca ccc aag tcg ccg tct tcc gcc aag 720
Lys Val Ala Val Val Arg Thr Pro Pro Lys Ser Pro Ser Ser Ala Lys
225 230 235 240 agc cgc ctg cag aca gcc ccc gtg ccc atg cca gac ctg aag aat gtc 768
Ser Arg Leu Gln Thr Ala Pro Val Pro Met Pro Asp Leu Lys Asn Val
245 250 255

-continued

```
aag tcc aag atc ggc tcc act gag aac ctg aag cac cag ccg gga ggc      816
Lys Ser Lys Ile Gly Ser Thr Glu Asn Leu Lys His Gln Pro Gly Gly
            260                 265                 270

ggg aag gtg cag ata att aat aag aag ctg gat ctt agc aac gtc cag      864
Gly Lys Val Gln Ile Ile Asn Lys Lys Leu Asp Leu Ser Asn Val Gln
        275                 280                 285

tcc aag tgt ggc tca aag gat aat atc aaa cac gtc ccg gga ggc ggc      912
Ser Lys Cys Gly Ser Lys Asp Asn Ile Lys His Val Pro Gly Gly Gly
    290                 295                 300

agt gtg caa ata gtc tac aaa cca gtt gac ctg agc aag gtg acc tcc      960
Ser Val Gln Ile Val Tyr Lys Pro Val Asp Leu Ser Lys Val Thr Ser
305                 310                 315                 320

aag tgt ggc tca tta ggc aac atc cat cat aaa cca gga ggt ggc cag     1008
Lys Cys Gly Ser Leu Gly Asn Ile His His Lys Pro Gly Gly Gly Gln
                325                 330                 335

gtg gaa gta aaa tct gag aag ctt gac ttc aag gac aga gtc cag tcg     1056
Val Glu Val Lys Ser Glu Lys Leu Asp Phe Lys Asp Arg Val Gln Ser
            340                 345                 350

aag att ggg tcc ctg gac aat atc acc cac gtc cct ggc gga gga aat     1104
Lys Ile Gly Ser Leu Asp Asn Ile Thr His Val Pro Gly Gly Gly Asn
        355                 360                 365

aaa aag att gaa acc cac aag ctg acc ttc cgc gag aac gcc aaa gcc     1152
Lys Lys Ile Glu Thr His Lys Leu Thr Phe Arg Glu Asn Ala Lys Ala
    370                 375                 380

aag aca gac cac ggg gcg gag atc gtg tac aag tcg cca gtg gtg tct     1200
Lys Thr Asp His Gly Ala Glu Ile Val Tyr Lys Ser Pro Val Val Ser
385                 390                 395                 400

ggg gac acg tct cca cgg cat ctc agc aat gtc tcc tcc acc ggc agc     1248
Gly Asp Thr Ser Pro Arg His Leu Ser Asn Val Ser Ser Thr Gly Ser
                405                 410                 415

atc gac atg gta gac tcg ccc cag ctc gcc acg cta gct gac gag gtg     1296
Ile Asp Met Val Asp Ser Pro Gln Leu Ala Thr Leu Ala Asp Glu Val
            420                 425                 430

tct gcc tcc ctg gcc aag cag ggt ttg tga                             1326
Ser Ala Ser Leu Ala Lys Gln Gly Leu
        435                 440


<210> SEQ ID NO 2
<211> LENGTH: 441
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110
```

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 3
<211> LENGTH: 1326
<212> TYPE: DNA
<213> ORGANISM: Homo sapiens
<220> FEATURE:
<221> NAME/KEY: CDS
<222> LOCATION: (1)..(1326)

<400> SEQUENCE: 3 atg gct gag ccc cgc cag gag ttc gaa gtg atg gaa gat cac gct ggg    48
Met Ala Glu Pro Arg Gln Glu Phe Glu Val Met Glu Asp His Ala Gly
1               5                   10                  15

-continued

```
acg tac ggg ttg ggg gac agg aaa gat cag ggg ggc tac acc atg cac        96
Thr Tyr Gly Leu Gly Asp Arg Lys Asp Gln Gly Gly Tyr Thr Met His
            20                  25                  30

caa gac caa gag ggt gac acg gac gct ggc ctg aaa gaa tct ccc ctg       144
Gln Asp Gln Glu Gly Asp Thr Asp Ala Gly Leu Lys Glu Ser Pro Leu
        35                  40                  45

cag acc ccc act gag gac gga tct gag gaa ccg ggc tct gaa acc tct       192
Gln Thr Pro Thr Glu Asp Gly Ser Glu Glu Pro Gly Ser Glu Thr Ser
    50                  55                  60

gat gct aag agc act cca aca gcg gaa gat gtg aca gca ccc tta gtg       240
Asp Ala Lys Ser Thr Pro Thr Ala Glu Asp Val Thr Ala Pro Leu Val
65                  70                  75                  80

gat gag gga gct ccc ggc aag cag gct gcc gcg cag ccc cac acg gag       288
Asp Glu Gly Ala Pro Gly Lys Gln Ala Ala Ala Gln Pro His Thr Glu
                85                  90                  95

atc cca gaa gga acc aca gct gaa gaa gca ggc att gga gac acc ccc       336
Ile Pro Glu Gly Thr Thr Ala Glu Glu Ala Gly Ile Gly Asp Thr Pro
            100                 105                 110

agc ctg gaa gac gaa gct gct ggt cac gtg acc caa gct cgc atg gtc       384
Ser Leu Glu Asp Glu Ala Ala Gly His Val Thr Gln Ala Arg Met Val
        115                 120                 125

agt aaa agc aaa gac ggg act gga agc gat gac aaa aaa gcc aag ggg       432
Ser Lys Ser Lys Asp Gly Thr Gly Ser Asp Asp Lys Lys Ala Lys Gly
    130                 135                 140

gct gat ggt aaa acg aag atc gcc aca ccg cgg gga gca gcc cct cca       480
Ala Asp Gly Lys Thr Lys Ile Ala Thr Pro Arg Gly Ala Ala Pro Pro
145                 150                 155                 160

ggc cag aag ggc cag gcc aac gcc acc agg att cca gca aaa acc ccg       528
Gly Gln Lys Gly Gln Ala Asn Ala Thr Arg Ile Pro Ala Lys Thr Pro
                165                 170                 175

ccc gct cca aag aca cca ccc agc tct ggt gaa cct cca aaa tca ggg       576
Pro Ala Pro Lys Thr Pro Pro Ser Ser Gly Glu Pro Pro Lys Ser Gly
            180                 185                 190

gat cgc agc ggc tac agc agc ccc ggc tcc cca ggc act ccc ggc agc       624
Asp Arg Ser Gly Tyr Ser Ser Pro Gly Ser Pro Gly Thr Pro Gly Ser
        195                 200                 205

cgc tcc cgc acc ccg tcc ctt cca acc cca ccc acc cgg gag ccc aag       672
Arg Ser Arg Thr Pro Ser Leu Pro Thr Pro Pro Thr Arg Glu Pro Lys
    210                 215                 220

aag gtg gca gtg gtc cgt act cca ccc aag tcg ccg tct tcc gcc aag       720
Lys Val Ala Val Val Arg Thr Pro Pro Lys Ser Pro Ser Ser Ala Lys
225                 230                 235                 240

agc cgc ctg cag aca gcc ccc gtg ccc atg cca gac ctg aag aat gtc       768
Ser Arg Leu Gln Thr Ala Pro Val Pro Met Pro Asp Leu Lys Asn Val
                245                 250                 255

aag tcc aag atc ggc tcc act gag aac ctg aag cac cag ccg gga ggc       816
Lys Ser Lys Ile Gly Ser Thr Glu Asn Leu Lys His Gln Pro Gly Gly
            260                 265                 270

ggg aag gtg cag ata att aat aag aag ctg gat ctt agc aac gtc cag       864
Gly Lys Val Gln Ile Ile Asn Lys Lys Leu Asp Leu Ser Asn Val Gln
        275                 280                 285

tcc aag tgt ggc tca aag gat aat atc aaa cac gtc ctg gga ggc ggc       912
Ser Lys Cys Gly Ser Lys Asp Asn Ile Lys His Val Leu Gly Gly Gly
    290                 295                 300

agt gtg caa ata gtc tac aaa cca gtt gac ctg agc aag gtg acc tcc       960
Ser Val Gln Ile Val Tyr Lys Pro Val Asp Leu Ser Lys Val Thr Ser
305                 310                 315                 320

aag tgt ggc tca tta ggc aac atc cat cat aaa cca gga ggt ggc cag      1008
Lys Cys Gly Ser Leu Gly Asn Ile His His Lys Pro Gly Gly Gly Gln
                325                 330                 335
```

-continued

```
gtg gaa gta aaa tct gag aag ctt gac ttc aag gac aga gtc cag tcg      1056
Val Glu Val Lys Ser Glu Lys Leu Asp Phe Lys Asp Arg Val Gln Ser
            340                 345                 350

aag att ggg tcc ctg gac aat atc acc cac gtc cct ggc gga gga aat      1104
Lys Ile Gly Ser Leu Asp Asn Ile Thr His Val Pro Gly Gly Gly Asn
        355                 360                 365

aaa aag att gaa acc cac aag ctg acc ttc cgc gag aac gcc aaa gcc      1152
Lys Lys Ile Glu Thr His Lys Leu Thr Phe Arg Glu Asn Ala Lys Ala
    370                 375                 380

aag aca gac cac ggg gcg gag atc gtg tac aag tcg cca gtg gtg tct      1200
Lys Thr Asp His Gly Ala Glu Ile Val Tyr Lys Ser Pro Val Val Ser
385                 390                 395                 400

ggg gac acg tct cca cgg cat ctc agc aat gtc tcc tcc acc ggc agc      1248
Gly Asp Thr Ser Pro Arg His Leu Ser Asn Val Ser Ser Thr Gly Ser
                405                 410                 415

atc gac atg gta gac tcg ccc cag ctc gcc acg cta gct gac gag gtg      1296
Ile Asp Met Val Asp Ser Pro Gln Leu Ala Thr Leu Ala Asp Glu Val
            420                 425                 430

tct gcc tcc ctg gcc aag cag ggt ttg tga                              1326
Ser Ala Ser Leu Ala Lys Gln Gly Leu
        435                 440


<210> SEQ ID NO 4
<211> LENGTH: 441
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220
```

```
Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Leu Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440
```

<210> SEQ ID NO 5
<211> LENGTH: 6
<212> TYPE: PRT
<213> ORGANISM: Homo sapiens

<400> SEQUENCE: 5

```
Val Gln Ile Ile Asn Lys
1               5
```

<210> SEQ ID NO 6
<211> LENGTH: 6
<212> TYPE: PRT
<213> ORGANISM: Homo sapiens

<400> SEQUENCE: 6

```
Val Gln Ile Val Tyr Lys
1               5
```

<210> SEQ ID NO 7
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (1)..(1)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 7

Val Gln Ile Ile Asn Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (3)..(3)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 8

Val Gln Ile Ile Asn Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (4)..(4)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 9

Val Gln Ile Ile Asn Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (1)..(1)
<223> OTHER INFORMATION: N-amination of the amino acid amide moiety
<220> FEATURE:
<221> NAME/KEY: MOD_RES
<222> LOCATION: (3)..(3)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 10

Val Gln Ile Ile Asn Lys
1 5

<210> SEQ ID NO 11
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (1)..(1)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 11

Val Gln Ile Val Tyr Lys
1 5

<210> SEQ ID NO 12
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (3)..(3)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 12

Val Gln Ile Val Tyr Lys
1 5

<210> SEQ ID NO 13
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (4)..(4)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 13

Val Gln Ile Val Tyr Lys
1 5

<210> SEQ ID NO 14
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (5)..(5)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 14

Val Gln Ile Val Tyr Lys
1 5

<210> SEQ ID NO 15
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (6)..(6)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 15

Val Gln Ile Val Tyr Lys
1 5

<210> SEQ ID NO 16
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (1)..(1)
<223> OTHER INFORMATION: N-amination of the amino acid amide moiety
<220> FEATURE:
<221> NAME/KEY: MOD_RES
<222> LOCATION: (3)..(3)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 16

Val Gln Ile Val Tyr Lys
1 5

<210> SEQ ID NO 17
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (1)..(1)
<223> OTHER INFORMATION: N-amination of the amino acid amide moiety
<220> FEATURE:
<221> NAME/KEY: MOD_RES
<222> LOCATION: (5)..(5)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 17

Val Gln Ile Val Tyr Lys
1 5

<210> SEQ ID NO 18
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (3)..(3)
<223> OTHER INFORMATION: N-amination of the amino acid amide moiety
<220> FEATURE:
<221> NAME/KEY: MOD_RES
<222> LOCATION: (5)..(5)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 18

Val Gln Ile Val Tyr Lys
1 5

<210> SEQ ID NO 19
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (4)..(4)
<223> OTHER INFORMATION: N-amination of the amino acid amide moiety -continued
<220> FEATURE:
<221> NAME/KEY: MOD_RES
<222> LOCATION: (6)..(6)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 19

Val Gln Ile Val Tyr Lys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation
<220> FEATURE:
<221> NAME/KEY: MOD_RES
<222> LOCATION: (1)..(1)
<223> OTHER INFORMATION: N-amination of the amino acid amide moiety
<220> FEATURE:
<221> NAME/KEY: MOD_RES
<222> LOCATION: (3)..(3)
<223> OTHER INFORMATION: N-amination of the amino acid amide moiety
<220> FEATURE:
<221> NAME/KEY: MOD_RES
<222> LOCATION: (5)..(5)
<223> OTHER INFORMATION: N-amination of the amino acid amide moiety
<220> FEATURE:
<221> NAME/KEY: MOD_RES
<222> LOCATION: (6)..(6)
<223> OTHER INFORMATION: C-term amidation

<400> SEQUENCE: 20

Val Gln Ile Val Tyr Gln
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: N-term acetylation

<400> SEQUENCE: 21

Val Gly Ile Ile Asn Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-term acetylation -continued

```
<220> FEATURE:
<221> NAME/KEY: MOD_RES
<222> LOCATION: (6)..(6)
<223> OTHER INFORMATION: C-term amidation

<400> SEQUENCE: 22

Val Gln Ile Val Tyr Lys
1               5
```